United States Patent
Dickerson et al.

(10) Patent No.: US 10,456,157 B2
(45) Date of Patent: Oct. 29, 2019

(54) ULTRASONIC SURGICAL INSTRUMENT CLAMP ARM WITH SNAP-ON CLAMP PAD

(71) Applicant: Ethicon Endo-Surgery, LLC, Guaynabo, PR (US)

(72) Inventors: Benjamin D. Dickerson, Cincinnati, OH (US); Kristen G. Denzinger, Cincinnati, OH (US); Ryan M. Asher, Cincinnati, OH (US); Collin J. Loch, Cincinnati, OH (US); Nathan D. Grubbs, West Chester, OH (US); Daniel J. Prenger, Loveland, OH (US); Laura A. Boehm, Hamilton, OH (US)

(73) Assignee: Ethicon LLC, Guaynabo, PR (US)

( * ) Notice: Subject to any disclaimer, the term of this patent is extended or adjusted under 35 U.S.C. 154(b) by 496 days.

(21) Appl. No.: 14/836,437

(22) Filed: Aug. 26, 2015

(65) Prior Publication Data

US 2017/0056060 A1    Mar. 2, 2017

(51) Int. Cl.
*A61B 17/32* (2006.01)
*A61N 7/00* (2006.01)
(Continued)

(52) U.S. Cl.
CPC ........ *A61B 17/320092* (2013.01); *A61N 7/00* (2013.01); *A61B 2017/00473* (2013.01);
(Continued)

(58) Field of Classification Search
CPC ........... A61B 17/320092; A61B 2017/320094; A61B 2017/320095; A61B 2017/320093
See application file for complete search history.

(56) References Cited

U.S. PATENT DOCUMENTS 5,322,055 A    6/1994  Davison et al.
5,324,299 A    6/1994  Davison et al.
(Continued)

FOREIGN PATENT DOCUMENTS

EP    2 074 959 A1    7/2009
EP    2 641 552 A2    9/2013
(Continued)

OTHER PUBLICATIONS

U.S. Appl. No. 61/410,603, filed Nov. 5, 2010.
International Search Report and Written Opinion dated Jan. 9, 2017 for Application No. PCT/US2016/047357, 18 pgs.

*Primary Examiner* — Thomas M McEvoy
(74) *Attorney, Agent, or Firm* — Frost Brown Todd LLC

(57) ABSTRACT

An apparatus for operating on tissue includes a body, a shaft assembly, and an end effector. The shaft assembly extends distally from the body and includes an acoustic waveguide. The waveguide is configured to acoustically couple with an ultrasonic transducer. The end effector includes an ultrasonic blade, a clamp arm, and a clamp pad. The blade is in acoustic communication with the waveguide. The clamp arm is configured to pivot about a first pivot point toward and away from the ultrasonic blade and includes a coupling feature. The clamp pad is selectively attachable to the blade to acoustically isolate the clamp arm from the ultrasonic blade. The coupling feature of the clamp arm is configured to provide a snap fit between the clamp pad and the clamp arm and thereby permit manipulation of the clamp pad for removal of the clamp pad from the clamp arm.

6 Claims, 68 Drawing Sheets

(51) Int. Cl.
    *A61B 18/00*     (2006.01)
    *A61B 17/00*     (2006.01)
    *A61B 17/28*     (2006.01)
    *A61B 17/29*     (2006.01)

(52) U.S. Cl.
    CPC ............. *A61B 2017/00477* (2013.01); *A61B 2017/2825* (2013.01); *A61B 2017/2931* (2013.01); *A61B 2017/320078* (2017.08); *A61B 2018/0063* (2013.01); *A61B 2018/00589* (2013.01); *A61B 2018/00595* (2013.01); *A61B 2018/00601* (2013.01); *A61B 2018/00607* (2013.01); *A61B 2018/00619* (2013.01)

(56) References Cited

U.S. PATENT DOCUMENTS

| | | |
|---|---|---|
| 5,873,873 A | 2/1999 | Smith et al. |
| 5,980,510 A | 11/1999 | Tsonton et al. |
| 6,139,561 A | 10/2000 | Shibata et al. |
| 6,283,981 B1 | 9/2001 | Beaupre |
| 6,309,400 B2 | 10/2001 | Beaupre |
| 6,325,811 B1 | 12/2001 | Messerly |
| 6,423,082 B1 | 7/2002 | Houser et al. |
| 6,773,444 B2 | 8/2004 | Messerly |
| 6,783,524 B2 | 8/2004 | Anderson et al. |
| 7,544,200 B2 | 6/2009 | Houser |
| 8,057,498 B2 | 11/2011 | Robertson |
| 8,142,461 B2 | 3/2012 | Houser et al. |
| 8,461,744 B2 | 6/2013 | Wiener et al. |
| 8,591,536 B2 | 11/2013 | Robertson |
| 8,623,027 B2 | 1/2014 | Price et al. |
| 8,911,460 B2 | 12/2014 | Neurohr et al. |
| 8,986,302 B2 | 3/2015 | Aldridge et al. |
| 9,023,071 B2 | 5/2015 | Miller et al. |
| 9,095,367 B2 | 8/2015 | Olson et al. |
| 9,381,058 B2 | 7/2016 | Houser et al. |
| 9,393,037 B2 | 7/2016 | Olson et al. |
| 9,724,120 B2 | 8/2017 | Faller et al. |
| 10,034,685 B2 | 7/2018 | Boudreaux et al. |
| 2004/0097911 A1 | 5/2004 | Murakami et al. |
| 2006/0079874 A1 | 4/2006 | Faller et al. |
| 2007/0191713 A1* | 8/2007 | Eichmann .......... A61B 17/1606 600/471 |
| 2007/0282333 A1 | 12/2007 | Fortson et al. |
| 2008/0200940 A1 | 8/2008 | Eichmann et al. |
| 2012/0116265 A1 | 5/2012 | Houser et al. |
| 2012/0116433 A1* | 5/2012 | Houser ............ A61B 17/00234 606/169 |
| 2015/0080924 A1 | 3/2015 | Stulen et al. |
| 2015/0148834 A1* | 5/2015 | Gee ................ A61B 17/320068 606/169 |
| 2015/0164532 A1* | 6/2015 | Faller ............. A61B 17/320092 606/169 |
| 2015/0245850 A1 | 9/2015 | Hibner et al. |
| 2016/0143659 A1 | 5/2016 | Glutz et al. |

FOREIGN PATENT DOCUMENTS

| | | |
|---|---|---|
| WO | WO 00/78237 A1 | 12/2000 |
| WO | WO 2007/047380 A2 | 4/2007 |

* cited by examiner

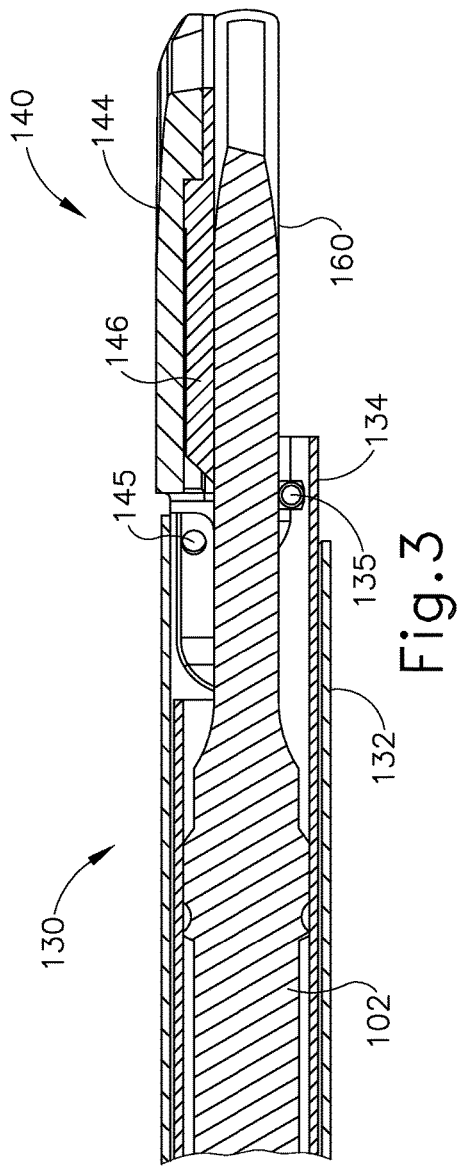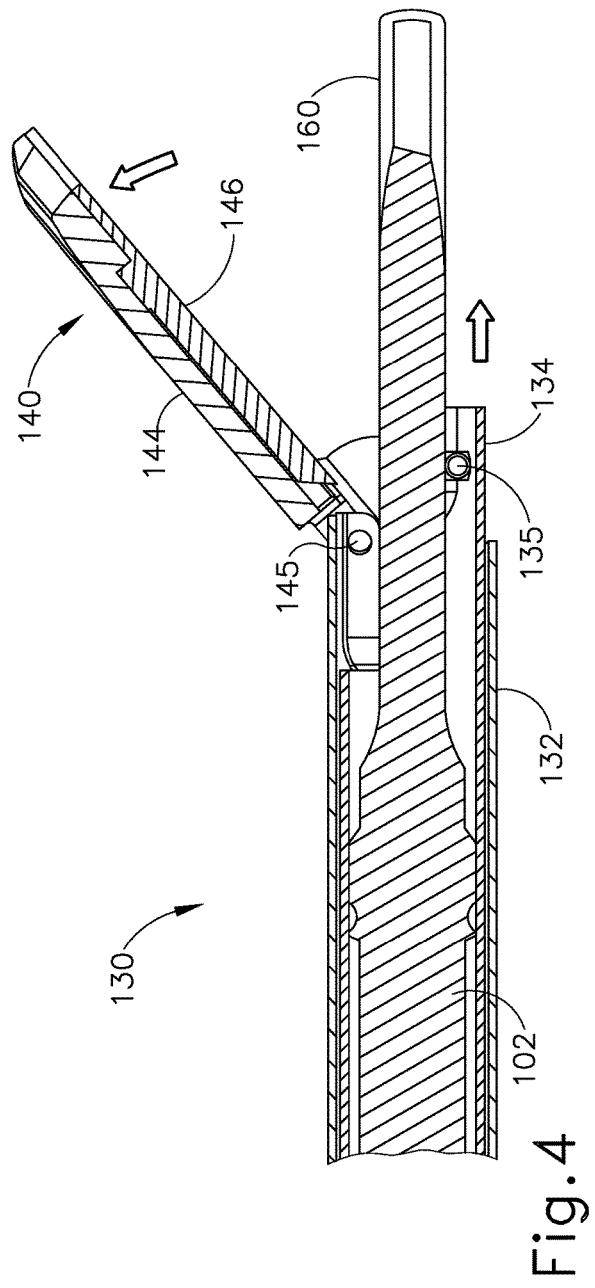

ULTRASONIC SURGICAL INSTRUMENT CLAMP ARM WITH SNAP-ON CLAMP PAD

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2008/0234710, entitled "Ultrasonic Surgical Instruments," published Sep. 25, 2008, issued as U.S. Pat. No. 8,911,460 on Dec. 16, 2014,the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, issued as U.S. Pat. No. 9,393,037 on Jul. 19, 2016, entitled "Surgical Instruments with Articulating Shafts," the disclosure of which is incorporated by reference herein; and U.S. Pub. No. 2014/0114334, published Apr. 24, 2014, issued as U.S. Pat. No. 9,095,367 on Aug. 4, 2015, entitled "Flexible Harmonic Waveguides/Blades for Surgical Instruments," the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 3 depicts a cross-sectional side view of an end effector of the instrument of FIG. 2 in a closed configuration;

FIG. 4 depicts a cross-sectional side view of the end effector of FIG. 3 in an open configuration;

Figure 1:
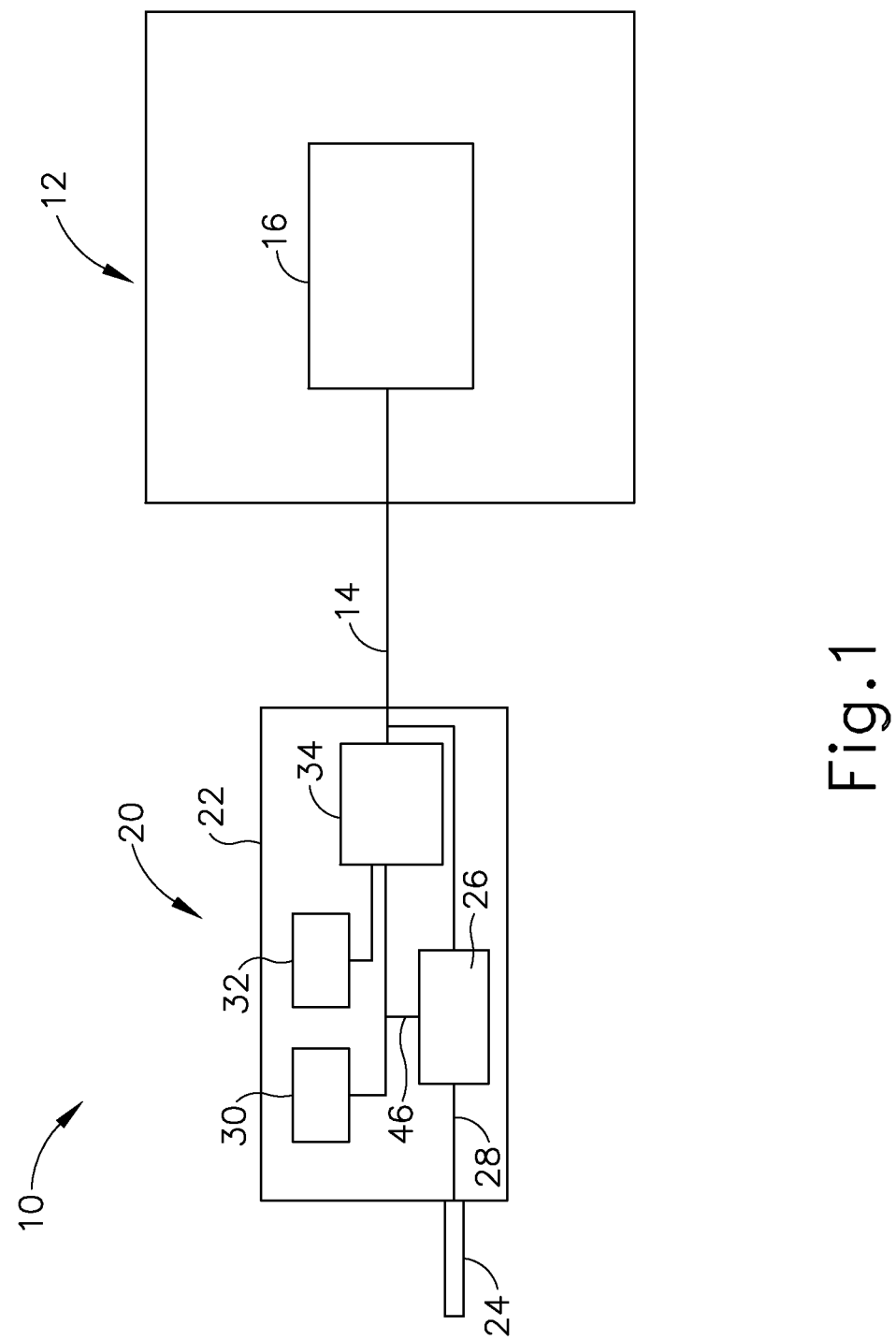
FIG. 1 depicts a block schematic view of an exemplary surgical system.
Figure 2:
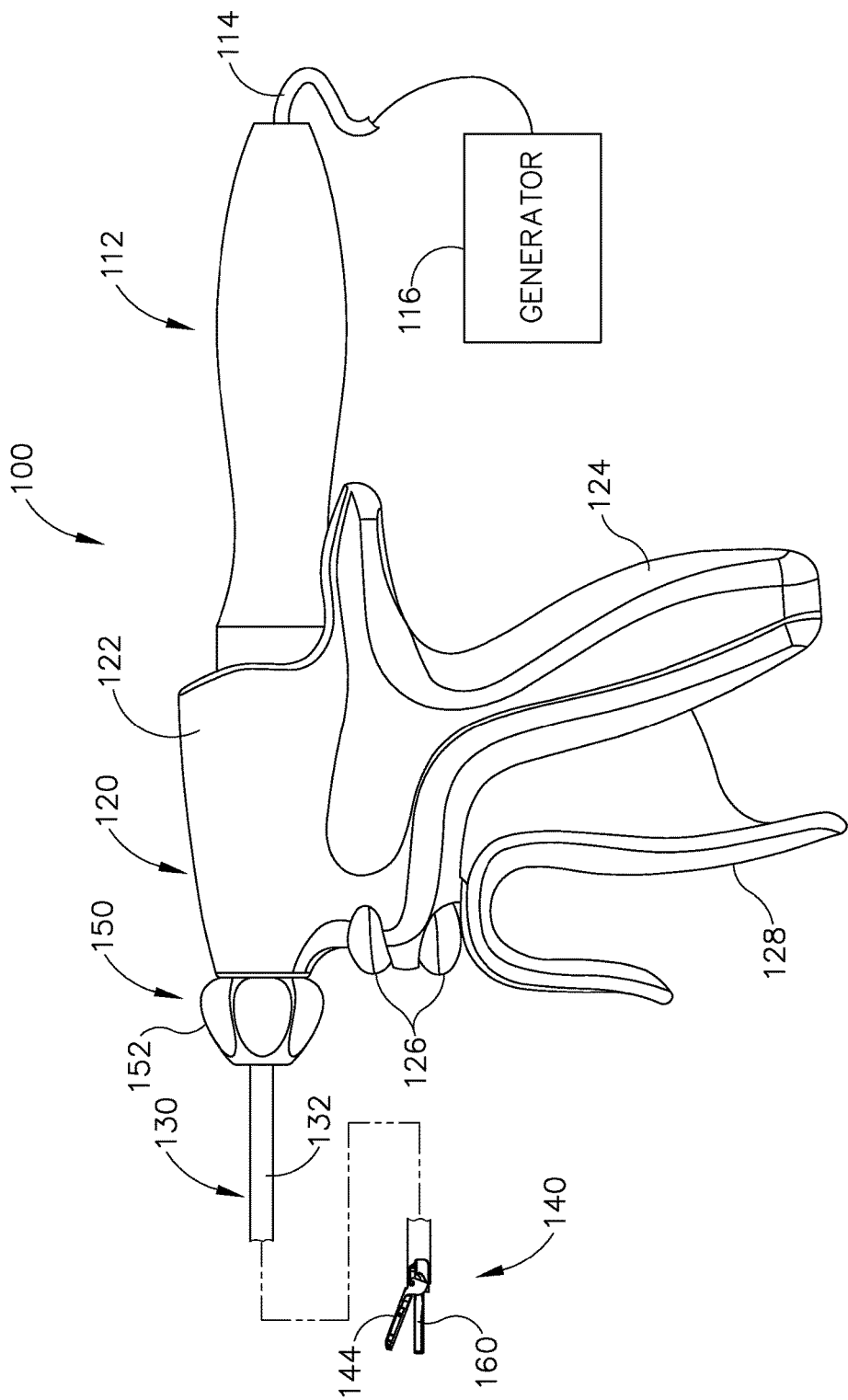
FIG. 2 depicts a side elevational view of an exemplary surgical instrument operable for use with the system of FIG. 1.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator.

I. Overview of Exemplary Ultrasonic Surgical System

FIG. 1 shows components of an exemplary surgical system (10) in diagrammatic block form. As shown, system (10) comprises an ultrasonic generator (12) and an ultrasonic surgical instrument (20). As will be described in greater detail below, instrument (20) is operable to cut tissue and seal or weld tissue (e.g., a blood vessel, etc.) substantially simultaneously, using ultrasonic vibrational energy. Generator (12) and instrument (20) are coupled together via cable (14). Cable (14) may comprise a plurality of wires; and may provide unidirectional electrical communication from generator (12) to instrument (20) and/or bidirectional electrical communication between generator (12) and instrument (20). By way of example only, cable (14) may comprise a "hot" wire for electrical power to surgical instrument (20), a ground wire, and a signal wire for transmitting signals from surgical instrument (20) to ultrasonic generator (12), with a shield surrounding the three wires. In some versions, separate "hot" wires are used for separate activation voltages (e.g., one "hot" wire for a first activation voltage and another "hot" wire for a second activation voltage, or a variable voltage between the wires proportional to the power requested, etc.). Of course, any other suitable number or configuration of wires may be used. It should also be understood that some versions of system (10) may incorporate generator (12) into instrument (20), such that cable (14) may simply be omitted.

By way of example only, generator (12) may comprise the GEN04, GEN11, or GEN 300 sold by Ethicon Endo-Surgery, Inc. of Cincinnati, Ohio. In addition or in the alternative, generator (12) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. Alternatively, any other suitable generator (12) may be used. As will be described in greater detail below, generator (12) is operable to provide power to instrument (20) to perform ultrasonic surgical procedures.

Instrument (20) comprises a handle assembly (22), which is configured to be grasped in one hand (or two hands) of an operator and manipulated by one hand (or two hands) of the operator during a surgical procedure. For instance, in some versions, handle assembly (22) may be grasped like a pencil by the operator. In some other versions, handle assembly (22) may include a scissor grip that may be grasped like scissors by the operator. In some other versions, handle assembly (22) may include a pistol grip that may be grasped like a pistol by the operator. Of course, handle assembly (22) may be configured to be gripped in any other suitable fashion. Furthermore, some versions of instrument (20) may substitute handle assembly (22) with a body that is coupled to a robotic surgical system that is configured to operate instrument (20) (e.g., via remote control, etc.). In the present example, a blade (24) extends distally from the handle assembly (22). Handle assembly (22) includes an ultrasonic transducer (26) and an ultrasonic waveguide (28), which couples ultrasonic transducer (26) with blade (24). Ultrasonic transducer (26) receives electrical power from generator (12) via cable (14). By virtue of its piezoelectric properties, ultrasonic transducer (26) is operable to convert such electrical power into ultrasonic vibrational energy.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. When blade (24) is in an activated state (i.e., vibrating ultrasonically), blade (24) is operable to effectively cut through tissue and seal tissue. Ultrasonic transducer (26), ultrasonic waveguide (28), and blade (24) together thus form an acoustic assembly providing ultrasonic energy for surgical procedures when powered by generator (12). Handle assembly (22) is configured to substantially isolate the operator from the vibrations of the acoustic assembly formed by transducer (26), ultrasonic waveguide (28), and blade (24).

In some versions, ultrasonic waveguide (28) may amplify the mechanical vibrations transmitted through ultrasonic waveguide (28) to blade (24). Ultrasonic waveguide (28) may further have features to control the gain of the longitudinal vibration along ultrasonic waveguide (28) and/or features to tune ultrasonic waveguide (28) to the resonant frequency of system (10). For instance, ultrasonic waveguide (28) may have any suitable cross-sectional dimensions/configurations, such as a substantially uniform cross-section, be tapered at various sections, be tapered along its entire length, or have any other suitable configuration. Ultrasonic waveguide (28) may, for example, have a length substantially equal to an integral number of one-half system wavelengths (nλ/2). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

In the present example, the distal end of blade (24) is located at a position corresponding to an anti-node associated with resonant ultrasonic vibrations communicated through waveguide (28) (i.e., at an acoustic anti-node), in order to tune the acoustic assembly to a preferred resonant frequency $f_o$ when the acoustic assembly is not loaded by tissue. When transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer (26) of the present example is activated, these mechanical oscillations are transmitted through waveguide (28) to reach blade (24), thereby providing oscillation of blade (24) at the resonant ultrasonic frequency. Thus, the ultrasonic oscillation of blade (24) may simultaneously sever the tissue and denature the proteins in adjacent tissue cells, thereby providing a coagulative effect with relatively little thermal spread. In some versions, an electrical current may also be provided through blade (24) to also cauterize the tissue.

By way of example only, ultrasonic waveguide (28) and blade (24) may comprise components sold under product codes SNGHK and SNGCB by Ethicon Endo-Surgery, Inc. of Cincinnati, Ohio. By way of further example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handle assembly (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). By way of example only, activation switch (32) may be constructed in accordance with any of the teachings of the various references cited herein. Other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the operator to select a desired level/amplitude of ultrasonic energy. By way of example only, control selector (30) may be constructed in accordance with any of the teachings of the various references cited herein. Other various forms that control selector (30) may take will be apparent to those of ordinary skill in the art in view of the teachings herein. In some versions, when an operator makes a selection through control selector (30), the operator's selection is communicated back to control circuitry (16) of generator (12) via cable (14), and control circuitry (16) adjusts the power communicated from generator (12) accordingly the next time the operator actuates activation switch (32).

It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power (via cable (14)) having characteristics associated with the ultrasonic energy level/amplitude or type selected through control selector (30). Generator (12) may thus be operable to communicate different types or degrees of electrical power to ultrasonic transducer (26), in accordance with selections made by the operator via control selector (30). In particular, and by way of example only, generator (12) may increase the voltage and/or current of the applied signal to increase the longitudinal amplitude of the acoustic assembly. As a merely illustrative example, generator (12) may provide selectability between a "level 1" and a "level 5," which may correspond with a blade (24) vibrational resonance amplitude of approximately 50 microns and approximately 90 microns, respectively. Various ways in which control circuitry (16) may be configured will be apparent to those of ordinary skill in the art in view of the teachings herein. It should also be understood that control selector (30) and activation switch (32) may be substituted with two or more activation switches (32). In some such versions, one activation switch (32) is operable to activate blade (24) at one power level/type while another activation switch (32) is operable to activate blade (24) at another power level/type, etc.

In some alternative versions, control circuitry (16) is located within handle assembly (22). For instance, in some such versions, generator (12) only communicates one type of electrical power (e.g., just one voltage and/or current available) to handle assembly (22), and control circuitry (16) within handle assembly (22) is operable to modify the electrical power (e.g., the voltage of the electrical power), in accordance with selections made by the operator via control selector (30), before the electrical power reaches ultrasonic transducer (26). Furthermore, generator (12) may be incorporated into handle assembly (22) along with all other components of surgical system (10). For instance, one or more batteries (not shown) or other portable sources of power may be provided in handle assembly (22). Still other suitable ways in which the components depicted in FIG. 1 may be rearranged or otherwise configured or modified will be apparent to those of ordinary skill in the art in view of the teachings herein.

II. Overview of Exemplary Ultrasonic Surgical Instrument

The following discussion relates to various exemplary components and configurations of instrument (20). It should be understood that the various examples of instrument (20) described below may be readily incorporated into surgical system (10) as described above. It should also be understood that the various components and operabilities of instrument (20) described above may be readily incorporated into the exemplary versions of instrument (20) described below. Various suitable ways in which the above and below teachings may be combined will be apparent to those of ordinary skill in the art in view of the teachings herein. It should also be understood that the below teachings may be readily combined with the various teachings of the references that are cited herein.

FIGS. 2-5 illustrate an exemplary ultrasonic surgical instrument (100). At least part of instrument (100) may be constructed and operable in accordance with at least some of the teachings of U.S. Pat. Nos. 5,322,055; 5,873,873; 5,980,510; 6,325,811; 6,773,444; 6,783,524; 8,461,744; 8,623,027; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 on May 5, 2015; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pub. No. 2014/0114334, issued as U.S. Pat. No. 9,095,367 on Aug. 4, 2015; U.S. patent application Ser. No. 61/410,603; and/or U.S. patent application Ser. No. 14/028,717, issued as U.S. Pat. No. 10,172,636 on Jan. 8, 2019. The disclosures of each of the foregoing patents, publications, and applications are incorporated by reference herein. As described therein and as will be described in greater detail below, instrument (100) is operable to cut tissue and seal or weld tissue (e.g., a blood vessel, etc.) substantially simultaneously. It should also be understood that instrument (100) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (100) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (100), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (100) of the present example comprises a handle assembly (120), a shaft assembly (130), and an end effector (140). Handle assembly (120) comprises a body (122) including a pistol grip (124) and a pair of buttons (126). Handle assembly (120) also includes a trigger (128) that is pivotable toward and away from pistol grip (124). It should be understood, however, that various other suitable configurations may be used, including but not limited to a pencil-grip configuration or a scissor-grip configuration. End effector (140) includes an ultrasonic blade (160) and a pivoting clamp arm (144). Clamp arm (144) is coupled with trigger (128) such that clamp arm (144) is pivotable toward ultrasonic blade (160) in response to pivoting of trigger (128) toward pistol grip (124); and such that clamp arm (144) is pivotable away from ultrasonic blade (160) in response to pivoting of trigger (128) away from pistol grip (124). Various suitable ways in which clamp arm (144) may be coupled with trigger (128) will be apparent to those of ordinary skill in the art in view of the teachings herein. In some versions, one or more resilient members are used to bias clamp arm (144) and/or trigger (128) to the open position shown in FIG. 4.

An ultrasonic transducer assembly (112) extends proximally from body (122) of handle assembly (120). Transducer assembly (112) is coupled with a generator (116) via a cable (114). Transducer assembly (112) receives electrical power from generator (116) and converts that power into ultrasonic vibrations through piezoelectric principles. Generator (116) may include a power source and control module that is configured to provide a power profile to transducer assembly (112) that is particularly suited for the generation of ultrasonic vibrations through transducer assembly (112). By way of example only, generator (116) may comprise a GEN 300 sold by Ethicon Endo-Surgery, Inc. of Cincinnati, Ohio. In addition or in the alternative, generator (116) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

Blade (160) of the present example is operable to vibrate at ultrasonic frequencies in order to effectively cut through and seal tissue, particularly when the tissue is being clamped between clamp arm (144) and blade (160). Blade (160) is positioned at the distal end of an acoustic drivetrain. This acoustic drivetrain includes transducer assembly (112) and an acoustic waveguide (102). Transducer assembly (112) includes a set of piezoelectric discs (not shown) located proximal to a horn (not shown) of rigid acoustic waveguide (102). The piezoelectric discs are operable to convert electrical power into ultrasonic vibrations, which are then transmitted along acoustic waveguide (102), which extends through shaft assembly (130), to blade (160) in accordance with known configurations and techniques. By way of example only, this portion of the acoustic drivetrain may be configured in accordance with various teachings of various references that are cited herein.

Waveguide (102) is secured within shaft assembly (130) via a pin (133), which passes through waveguide (102) and shaft assembly (130). Pin (133) is located at a position along the length of waveguide (102) corresponding to a node associated with resonant ultrasonic vibrations communicated through waveguide (102). When ultrasonic blade (160) is in an activated state (i.e., vibrating ultrasonically), ultrasonic blade (160) is operable to effectively cut through and seal tissue, particularly when the tissue is being clamped between clamp arm (144) and ultrasonic blade (160). It should be understood that waveguide (102) may be configured to amplify mechanical vibrations transmitted through waveguide (102). Furthermore, waveguide (102) may include features operable to control the gain of the longitudinal vibrations along waveguide (102) and/or features to tune waveguide (102) to the resonant frequency of the system.

In the present example, the distal end of blade (160) is located at a position corresponding to an anti-node associated with resonant ultrasonic vibrations communicated through waveguide (102), in order to tune the acoustic assembly to a preferred resonant frequency $f_o$ when the acoustic assembly is not loaded by tissue. When transducer assembly (112) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (112) of the present example is activated, these mechanical oscillations are transmitted through waveguide (102) to reach blade (160), thereby providing oscillation of blade (160) at the resonant ultrasonic frequency. Thus, when tissue is secured between blade (160) and clamp arm (144), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm (144) to also cauterize the tissue. While some configurations for an acoustic transmission assembly and transducer assembly (112) have been described, still other suitable configurations for an acoustic transmission assembly and transducer assembly (112) will be apparent to one or ordinary skill in the art in view of the teachings herein. Similarly, other suitable configurations for end effector (140) will be apparent to those of ordinary skill in the art in view of the teachings herein.

An operator may activate buttons (126) to selectively activate transducer assembly (112) to activate blade (160). In the present example, two buttons (126) are provided—one for activating blade (160) at a low power and another for activating blade (160) at a high power. However, it should be understood that any other suitable number of buttons and/or otherwise selectable power levels may be provided. For instance, a foot pedal may be provided to selectively activate transducer assembly (112). Buttons (126) of the present example are positioned such that an operator may readily fully operate instrument (100) with a single hand. For instance, the operator may position their thumb about pistol grip (124), position their middle, ring, and/or little finger about trigger (128), and manipulate buttons (126) using their index finger. Of course, any other suitable techniques may be used to grip and operate instrument (100); and buttons (126) may be located at any other suitable positions.

Shaft assembly (130) of the present example comprises an outer sheath (132), an inner tube (134) slidably disposed within outer sheath (132), and a waveguide (102) disposed within inner tube (134). As will be discussed in more detail below inner tube (134) is operable to translate longitudinally within outer sheath (132) relative to outer sheath (132) to selectively pivot clamp arm (144) toward and away from blade (160). Shaft assembly (130) of the present example further includes a rotation assembly (150). Rotation assembly (150) is operable to rotate the entire shaft assembly (130) and end effector (140) relative to handle assembly (120) about a longitudinal axis of shaft assembly (130). In some versions, rotation assembly (150) is operable to selectively lock the angular position of shaft assembly (130) and end effector (140) relative to handle assembly (120) about the longitudinal axis of shaft assembly (130). For instance, a rotation knob (152) of rotation assembly (150) may be translatable between a first longitudinal position, in which shaft assembly (130) and end effector (140) are rotatable relative to handle assembly (120) about the longitudinal axis of shaft assembly (130); and a second longitudinal position, in which shaft assembly (130) and end effector (140) are not rotatable relative to handle assembly (120) about the longitudinal axis of shaft assembly (130). Of course, shaft assembly (130) may have a variety of other components, features, and operabilities, in addition to or in lieu of any of those noted above. Other suitable configurations for shaft assembly (130) will be apparent to those of ordinary skill in the art in view of the teachings herein.

As shown in FIGS. 3 and 4, end effector (140) includes ultrasonic blade (160) and clamp arm (144). Clamp arm (144) includes a clamp pad (146) secured to an underside of clamp arm (144), facing blade (160). Clamp arm (144) is pivotably coupled with a distal end of outer sheath (132) of shaft assembly (130) above ultrasonic blade (160) via a pin (145). As best seen in FIG. 4, a distal end of inner tube (134) is rotatably coupled with a proximal end of clamp arm (144) below ultrasonic blade (160) via a pin (135) such that longitudinal translation of inner tube (134) causes rotation of clamp arm (144) about pin (145) toward and away from ultrasonic blade (160) to thereby clamp tissue between clamp arm (144) and ultrasonic blade (160) to cut and/or seal the tissue. In particular, proximal longitudinal translation of inner tube (134) relative to outer sheath (132) and handle assembly (120) causes clamp arm (144) to move toward ultrasonic blade (160); and distal longitudinal translation of inner tube (134) relative to outer sheath (132) and handle assembly (120) causes clamp arm (144) to move away from ultrasonic blade (160).

Figure 5:
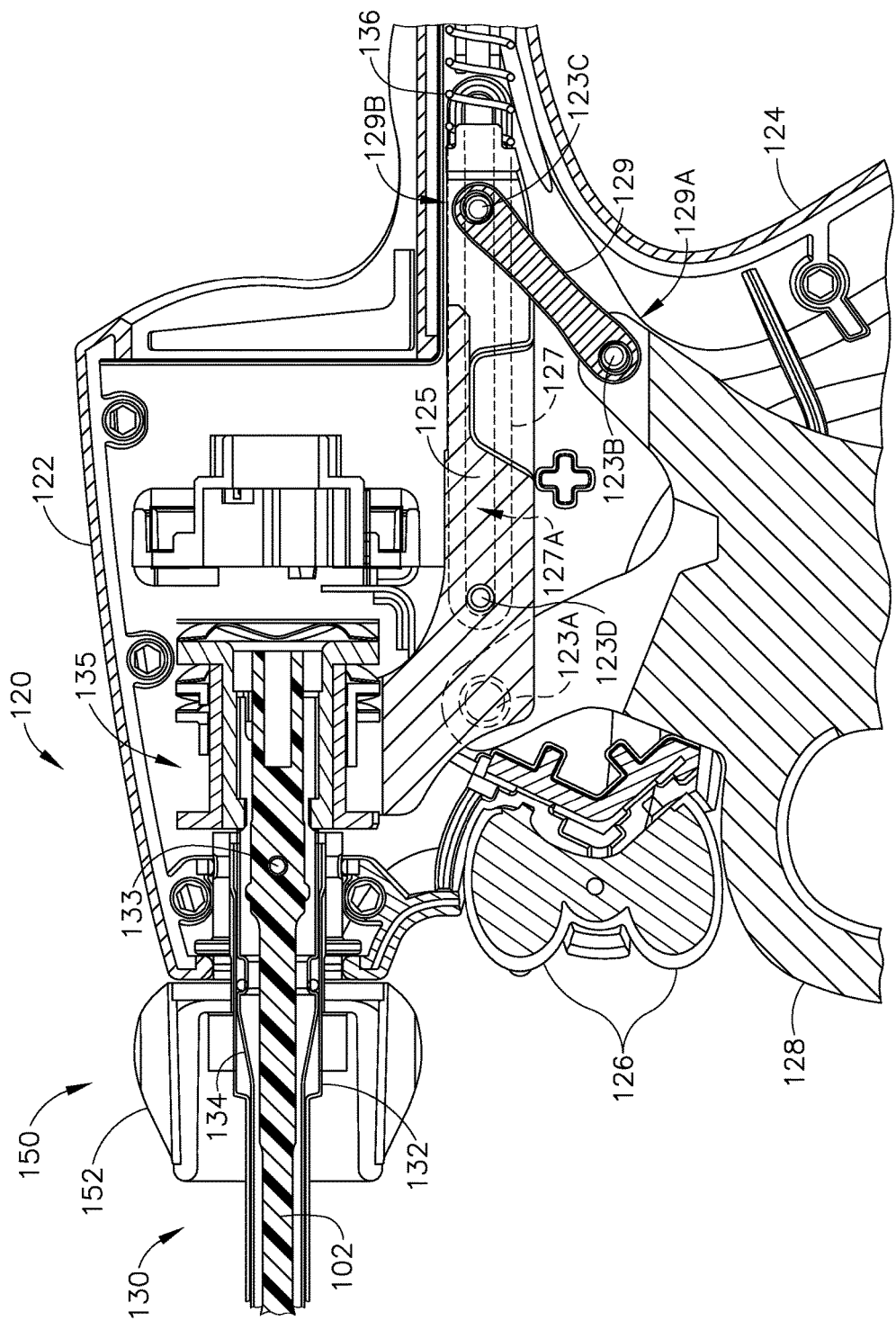
FIG. 5 depicts a cross-sectional side view of a handle assembly of the instrument of FIG. 2.

As shown in FIG. 5, and as discussed above, trigger (128) is pivotably coupled to handle assembly (120) via a pin (123A) such that trigger (128) is operable to rotate about pin (123A). As will be described in more detail below, trigger (128) is coupled with a yoke (125) via a linkage (129) such that rotation of trigger (128) about pin (123A) causes longitudinal translation of yoke (125). A first end (129A) of linkage (129) is rotatably coupled with a proximal portion of trigger (128) via a pin (123B). A second end (129B) of linkage (129) is rotatably coupled with a proximal portion of yoke (125) via a pin (123C). A pair of elongate oval-shaped projections (127) extend inwardly from interior surfaces of body (122). An interior surface of each oval-shaped projection (127) defines an elongate oval-shaped slot (127A). Pin (123C) passes completely through the proximal portion of yoke (125) and second end (129B) of linkage (129) such that ends of pin (123C) extend from opposite sides of yoke (125). These ends of pin (123C) are slidably and rotatably disposed within oval-shaped slots (127A). A pin (123D) passes completely through a distal portion of yoke (125) such that ends of pin (123D) extend from opposite sides of yoke (125). These ends of pin (123D) are slidably and rotatably disposed within oval-shaped slots (127A). It should therefore be understood that yoke (125) is longitudinally translatable within oval-shaped slots (127A) via pins (123C, 123D) between a proximal longitudinal position and a distal longitudinal position. Furthermore, because the proximal portion of trigger (128) is coupled with yoke (125) via linkage (129), pivoting of trigger (128) toward and away from pistol grip (124) will cause longitudinal translation of yoke (125) within oval-shaped slots (127A). In particular, pivoting of trigger (128) toward pistol grip (124) will cause proximal longitudinal translation of yoke (125) within oval-shaped slots (127A); and that pivoting of trigger (128) away from pistol grip (124) will cause distal longitudinal translation of yoke (125) within oval-shaped slots (127A).

A distal portion of yoke (125) is coupled with inner tube (134) of shaft assembly (130) via a coupling assembly (135). As discussed above, inner tube (134) is longitudinally translatable within outer sheath (132), such that inner tube (134) is configured to longitudinally translate concurrently with yoke (125). Furthermore, because pivoting of trigger (128) toward pistol grip (124) causes proximal longitudinal translation of yoke (125), it should be understood that pivoting of trigger (128) toward pistol grip (124) will cause proximal longitudinal translation of inner tube (134) relative to outer sheath (132) and handle assembly (120); and because pivoting of trigger (128) away from pistol grip (124) causes distal longitudinal translation of yoke (125), it should be understood that and that pivoting of trigger (128) away from pistol grip (124) will cause distal longitudinal translation of inner tube (134) relative to outer sheath (132) and handle assembly (120). Finally, because longitudinal translation of inner tube (134) causes rotation of clamp arm (144) toward and away from blade (160) as discussed above, it should be understood that pivoting of trigger (128) toward pistol grip (124) will cause clamp arm (144) to move toward ultrasonic blade (160); and that pivoting of trigger (128) away from pistol grip (124) will cause clamp arm (144) to move away from ultrasonic blade (160).

In some versions, one or more resilient members are used to bias clamp arm (144) and/or trigger (128) to the open position shown in FIG. 4. For instance, as shown in FIG. 5, a spring (136) is positioned within a proximal end of body (122) of handle assembly (120). Spring (136) bears against body (122) and a proximal end of yoke (125) to thereby bias yoke (125) toward the distal position. Biasing of yoke (125) toward the distal position causes inner tube (134) to be biased distally and further causes trigger (128) to be biased away from pistol grip (124).

Figure 6:
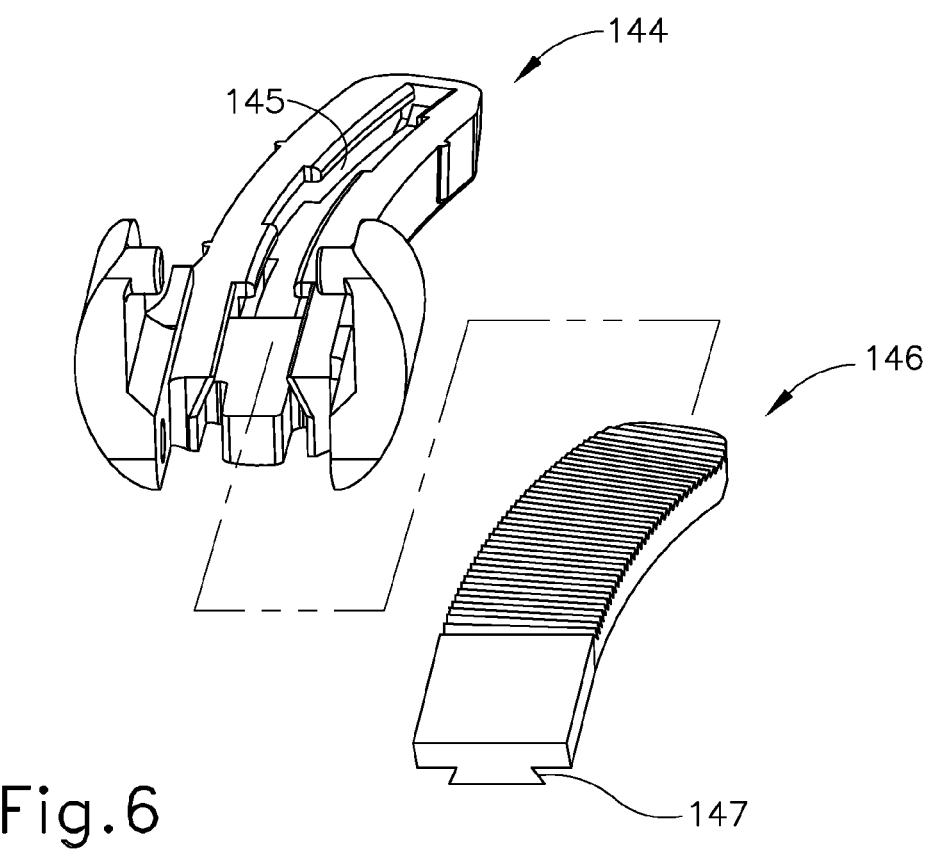
FIG. 6 depicts a perspective exploded view of a clamp arm and clamp pad of the end effector of FIG. 3.
Figure 7:
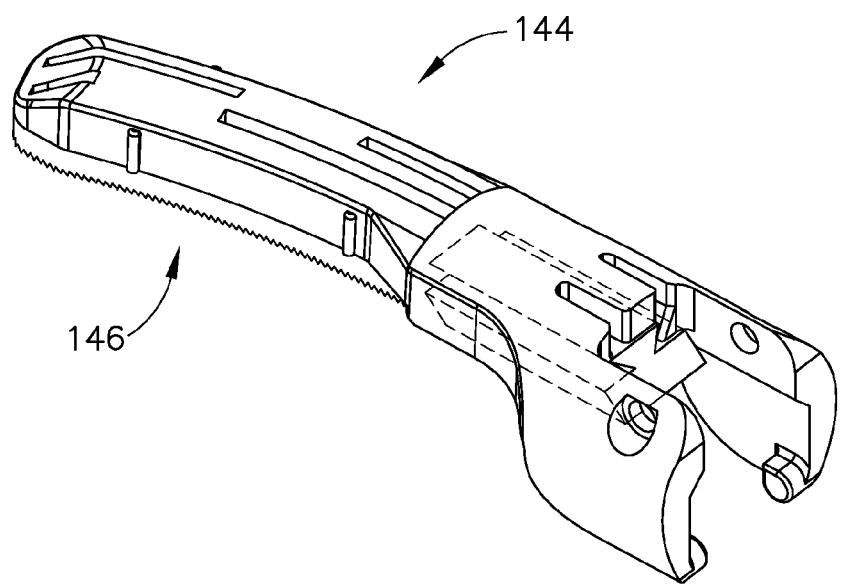
FIG. 7 depicts a perspective view of a clamp arm and clamp pad of FIG. 6.

FIGS. 6-7 show clamp arm (144) and clamp pad (146) in greater detail. As can be seen, clamp arm (144) and clamp pad (146) comprise two component parts that may be selectively separated by an operator. In particular, clamp pad (146) comprises a proximal portion that is smoother than a distal portion, such that the proximal portion may be devoid of saw-tooth-like teeth or other non-flat tissue engaging surface geometries contemplated. Utilizing a smooth proximal portion on clamp pad permits tissue in the proximal region to move distally, following the vibratory motion of blade (160), to the more active region of blade (160) to prevent tissue tagging. This concept takes advantage of the inherent motion profile of blade (160). Due to sinusoidal motion, the greatest displacement or amplitude of motion is located at the most distal portion of blade (160), while the proximal portion of the tissue treatment region is on the order of 50% of the distal tip amplitude. During operation, the tissue in the proximal region of end effector (140) will desiccate and thin, and the distal portion of end effector (140) will transect tissue in that distal region, thereby allowing the desiccated and thin tissue within the proximal region to slide distally into the more active region of end effector (140) to complete the tissue transaction.

To secure clamp pad (146) within clamp arm (144), clamp pad (146) includes an elongate key (147) extending the longitudinal length of clamp pad (146). Key (147) flares outwardly in a dovetail configuration as key extends downwardly from the body of clamp pad (146). As will be described in greater detail below, this dovetail flaring of key (147) is configured to secure clamp pad (146) to clamp arm (144). By way of example only, clamp pad (146) may be constructed and operable in accordance with the teachings of U.S. Pat. No. 7,544,200, entitled "Combination Tissue Pad for Use with an Ultrasonic Surgical Instrument," issued Jun. 9, 2009, the disclosure of which is incorporated by reference herein.

To receive clamp pad (146), clamp arm (144) includes a longitudinally extending channel (145) disposed therein. Channel (145) is configured to receive key (147) of clamp pad (146). Accordingly channel (145) is flared inwardly, thereby forming a dovetail shape corresponding to key (147). Channel (145) further includes a closed distal end and an open proximal end. Thus, to secure clamp pad (146) to clamp arm (144) an operator may insert key (147) of pad into the open proximal end of channel (145). Clamp pad (146) is then slid distally relative to clamp arm (144) to the position shown in FIG. 7 until further sliding is prohibited by the closed distal end of channel (145). It should be understood that clamp arm (144) would need to be disassembled from shaft assembly (130) in order for clamp pad (146) to be installed on clamp arm (144). Similarly, if an operator wished to remove clamp pad (146) from clamp arm (144) (e.g., in order to replace clamp pad (146) as described below), the operator would need to first remove clamp arm (144) from shaft assembly (130).

The foregoing components and operabilities of instrument (100) are merely illustrative. Instrument (100) may be configured in numerous other ways as will be apparent to those of ordinary skill in the art in view of the teachings herein. By way of example only, at least part of instrument (100) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 7,544,200; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 on May 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul 19, 2016; and/or U.S. Pub. No. 2014/0114334, issued as U.S. Pat. No. 9,095,367 on Aug. 4, 2015. Additional merely illustrative variations for instrument (100) will be described in greater detail below. It should be understood that the below described variations may be readily applied to instrument (100) described above and any of the instruments referred to in any of the references that are cited herein, among others.

III. Exemplary Detachable Clamp Arms

Those of ordinary skill in the art will recognize that clamp pad (146) may experience a substantial amount of wear and dear during use of end effector (140). For instance, clamp pad (146) may be formed of a polytetrafluoroethylene (PTFE) material. Clamp pad (146) may encounter heat, compression forces, and vibrations generated via blade (160), which may work together to eventually wear out the material forming clamp pad (146). It may therefore be desirable to provide a version of end effector (140) where clamp pad (146) is replaceable. In particular, it may be desirable to enable replacement of clamp pad (146) without necessarily also having to replace clamp arm (144) and/or other components of end effector (140).

It may therefore be desirable to provide clamp arms (144) with features configured to allow an operator to selectively remove or otherwise decouple clamp pad (146) from clamp arm (144). One merely exemplary way in which to provide such selective operation to clamp arm (144) is to provide clamp arm (144) with features operable to permit selective removal of clamp arm (144) itself. Such features may be desirable because such features may permit an operator to more easily manipulate clamp arm (144) for removal of clamp pad (146). Alternatively, it may be desirable to enable removal and replacement of a clamp pad (146) without requiring any removal of clamp arm (144) from shaft assembly (130). The examples described below provide various examples of features and techniques configured to allow an operator to selectively replace a clamp pad similar to clamp pad (146), with or without also including removal of a clamp arm similar to clamp arm (144) from a shaft assembly.

In any of the examples described below, instrument (100) may be further modified in accordance with at least some of the teachings of U.S. patent application Ser. No. 14/623,812, entitled "Ultrasonic Surgical Instrument with Removable Handle Assembly," filed Feb. 17, 2015, issued as U.S. Pat. No. 10,010,340 on Jul. 3, 2018, the disclosure of which is incorporated by reference herein. For instance, instrument (100) may be modified to enable clamp arm (144) to be hyperextended to pivot wider than the open position shown in FIG. 4, as disclosed in U.S. patent application Ser. No. 14/623,812, issued as U.S. Pat. No. 10,010,340 on Jul. 3, 2018, (see, e.g., FIGS. 36A-36B and associated text of U.S. patent application Ser. No. 14/623,812, issued as U.S. Pat. No. 10,010,340 on Jul. 3, 2018). Such hyperextension of clamp arm (144) may provide easier access to clamp pad (146) and thereby further facilitate replacement of clamp pad (146).

Figure 20:
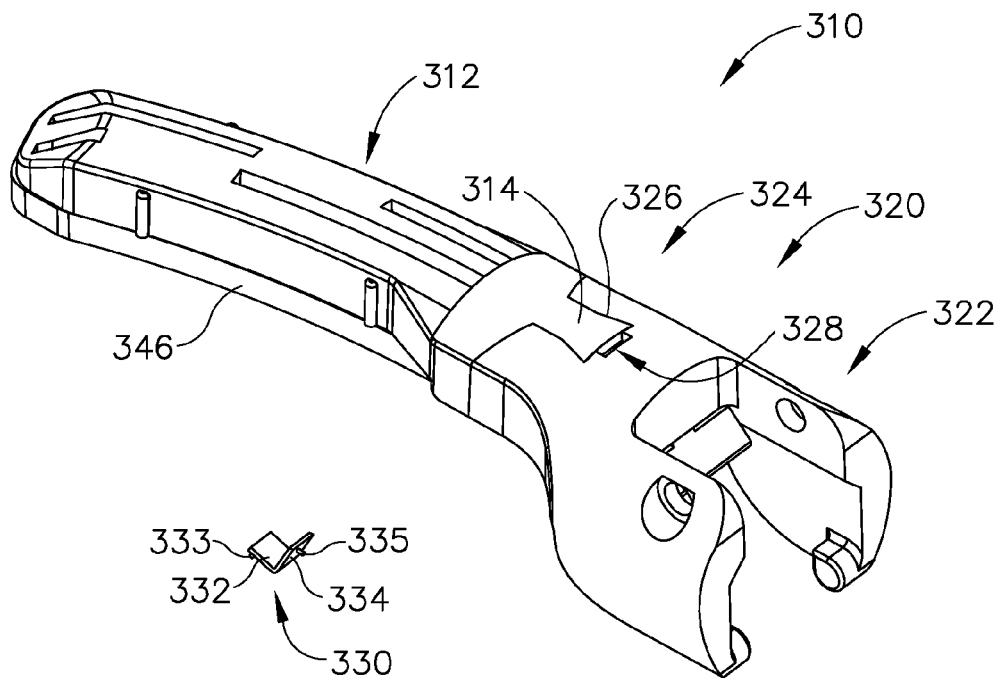
FIG. 20 depicts still another perspective view of the clamp portion of FIG. 17, with the clamp portion fully inserted into a body of the clamp arm of FIG. 15.

In addition or in the alternative, in any of the examples described below, instrument (100) may be further modified in accordance with at least some of the teachings of U.S. patent application Ser. No. 14/553,378, entitled "Ultrasonic Surgical Instrument with Blade Cooling through Retraction," filed Nov. 25, 2014, published as U.S. Pub. No. 2016/0143659 on May 26, 2016, the disclosure of which is incorporated by reference herein. For instance, instrument (100) may be modified to enable blade (160) to be retracted proximally from the position shown in FIG. 4, as disclosed in U.S. patent application Ser. No. 14/553,378, published as U.S. Pub. No. 2016/0143659 on May 26, 2016 (see, e.g., FIGS. 20A-20B and associated text of U.S. patent application Ser. No. 14/553,378, published as U.S. Pub. No. 2016/0143659 on May 26, 2016). Such retraction of blade (160) may also provide easier access to clamp pad (146) and thereby further facilitate replacement of clamp pad (146) in accordance with the teachings below.

As yet another merely illustrative example, the various teachings below may be combined with the various teachings of U.S. patent application Ser. No. 14/552,614, entitled "Ultrasonic Surgical Instrument with Staged Clamping," filed Nov. 25, 2014, issued as U.S. Pat. No. 10,004,527 on Jun. 26, 2018, the disclosure of which is incorporated by reference herein. While several examples are described in greater detail below, other examples will be apparent to those of ordinary skill in the art according to the teachings herein. Similarly, various suitable ways in which the below teachings may be combined with the teachings of the various references cited herein will be apparent to those of ordinary skill in the art.

A. Exemplary Rotatably Detachable Clamp Arm

Figure 8:
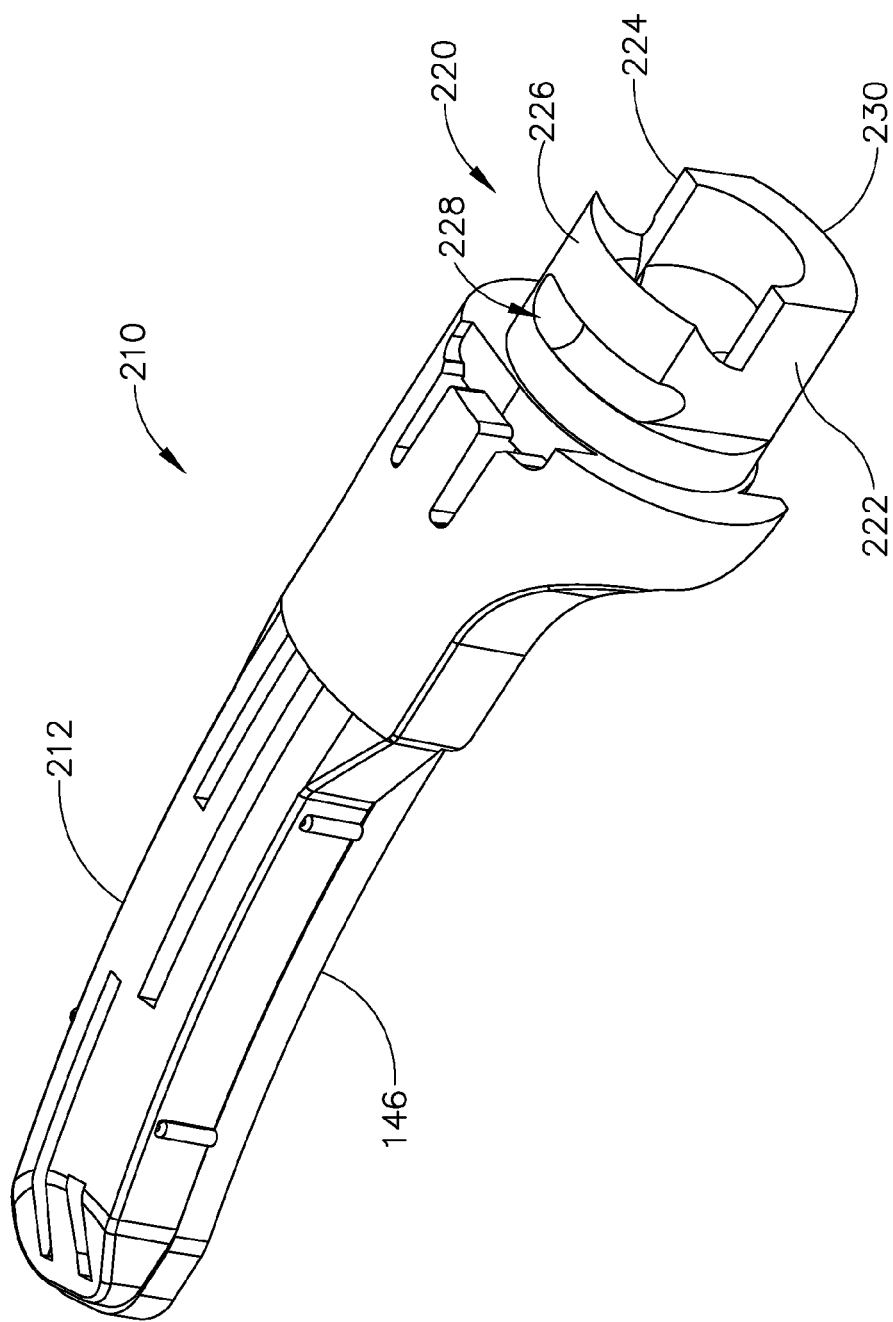
FIG. 8 depicts a perspective view of an exemplary alternative clamp arm for use with the instrument of FIG. 2.
Figure 9:
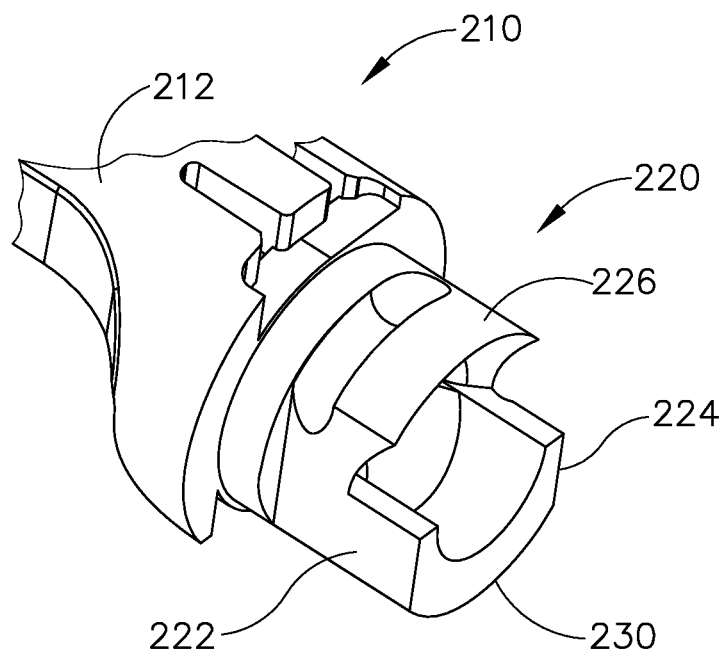
FIG. 9 depicts a detailed perspective view of the proximal end of the clamp arm of FIG. 8.
Figure 10:
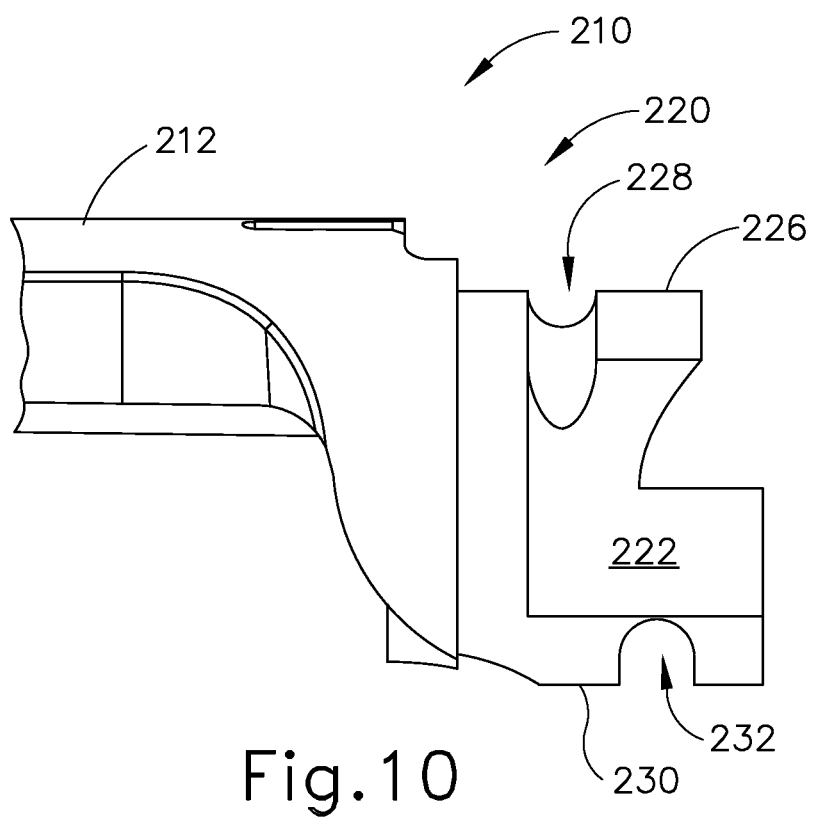
FIG. 10 depicts a detailed side elevational view of the proximal end of the clamp arm of FIG. 8.

FIGS. 8-10 show an exemplary alternative clamp arm (210) that may be readily incorporated into instrument (100) described above. Clamp arm (210) is substantially the same as clamp arm (144) described above unless otherwise described herein. Clamp arm (210) comprises an elongate body (212) extending distally from a proximal coupling member (220). Body (212) of the present example is shown coupled to clamp pad (146) described above, although it should be understood that any other suitable clamp pad may be used. Although not shown, it should be understood that body (212) includes similar features for coupling clamp pad (146) as clamp arm (144) described above. For instance, body (212) comprises channels or other features configured for receiving corresponding portions of clamp pad (146).

Unlike clamp arm (144), clamp arm (210) of the present example comprises coupling member (220). Coupling member (220) is generally configured to permit selective coupling of clamp arm (210) to instrument (100). As will be described in greater detail below, coupling member (220) generally facilities selective coupling between clamp arm (210) and instrument (100) by a user rotating clamp arm (210) relative to instrument (100) about the longitudinal axis of clamp arm (210).

As can best be seen in FIGS. 9 and 10, coupling member (220) comprises two flat faces (222, 224) circumscribing an upper and lower pair of annular faces (226, 230). As will be described in greater detail below, each flat face (222, 224) is configured to permit insertion of coupling member (220) into instrument (100) when coupling member (220) is oriented at a 90 degree angle relative to instrument (100).

Each annular face (226, 230) is generally rounded in shape at a radius corresponding to the inner diameter of shaft assembly (130) of instrument (100). Each annular face (226, 230) defines a rounded channel (228, 232) therein. As will be described in greater detail below, each channel (228, 232) is configured to receive a respective pin (145, 135) of instrument (100). Moreover, each channel (228, 232) is open to each flat face (222, 224). As will also be described in greater detail below, such a feature of channels (228, 232) permits each channel (228, 232) to receive a respective pin (145, 135) as clamp arm (210) is rotated relative to instrument (100).

Figure 11:
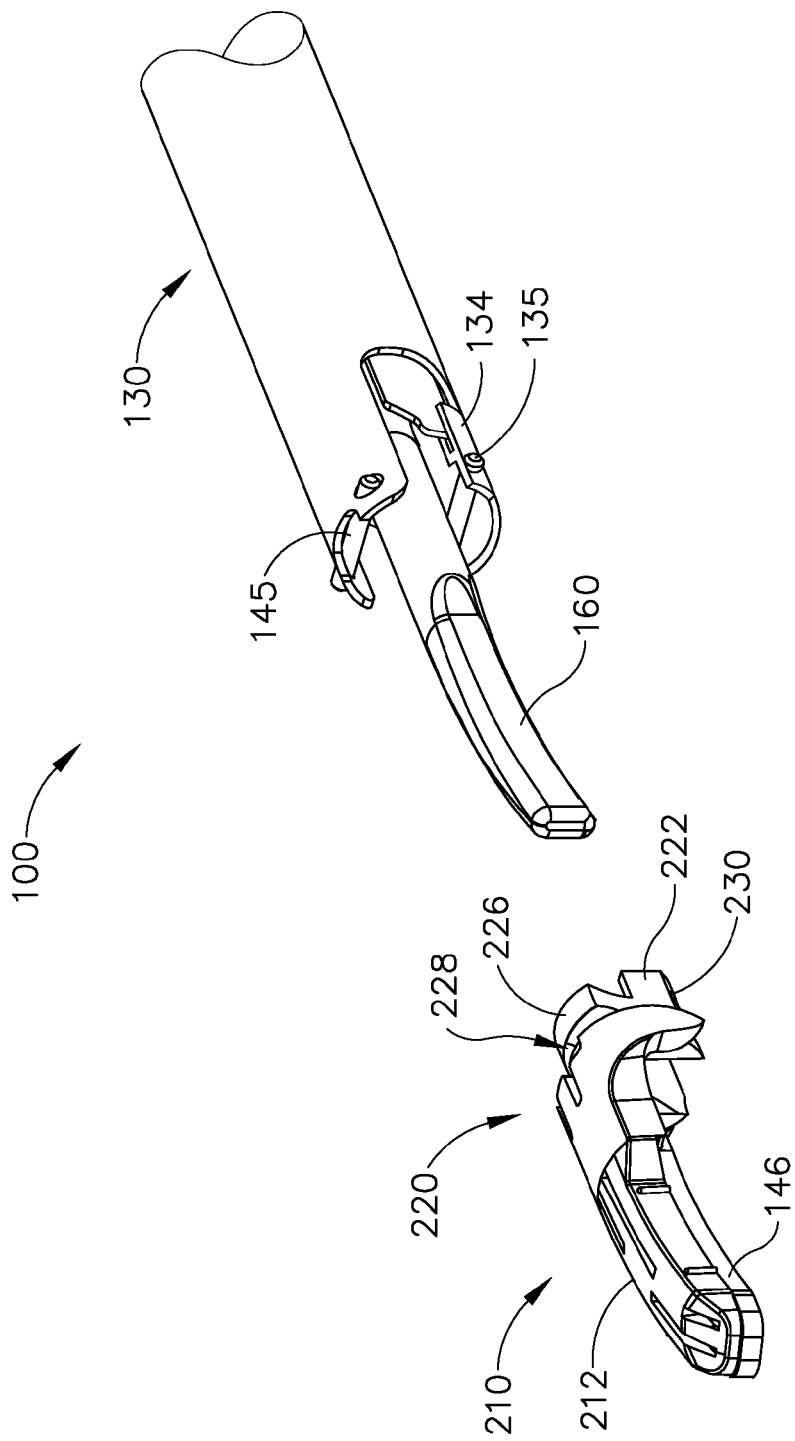
FIG. 11 depicts a perspective view of the clamp arm of FIG. 8 separated from the the instrument of FIG. 2.

FIGS. 11-14 show an exemplary operation for coupling clamp arm (210) to instrument (100). In particular, FIG. 11 shows clamp arm (210) removed from instrument (100) in a first orientation relative to instrument (100). It should be understood that the first orientation of clamp arm (210) shown in FIG. 11 corresponds to the general orientation that clamp arm (210) is in when instrument (100) is usable in a surgical procedure. However, in FIG. 11 clamp arm (210) is not attached to instrument (100), thereby rendering instrument (100) temporarily unsuitable for a surgical procedure. When clamp arm (210) is removed from instrument (100) as shown in FIG. 11, clamp arm (210) is readily manipulatable by an operator. As such, it may be relatively easy to remove and replace clamp pad (146) because clamp arm (210) may be positioned in any position that an operator deems desirable for clamp pad (146) removal.

Figure 12:
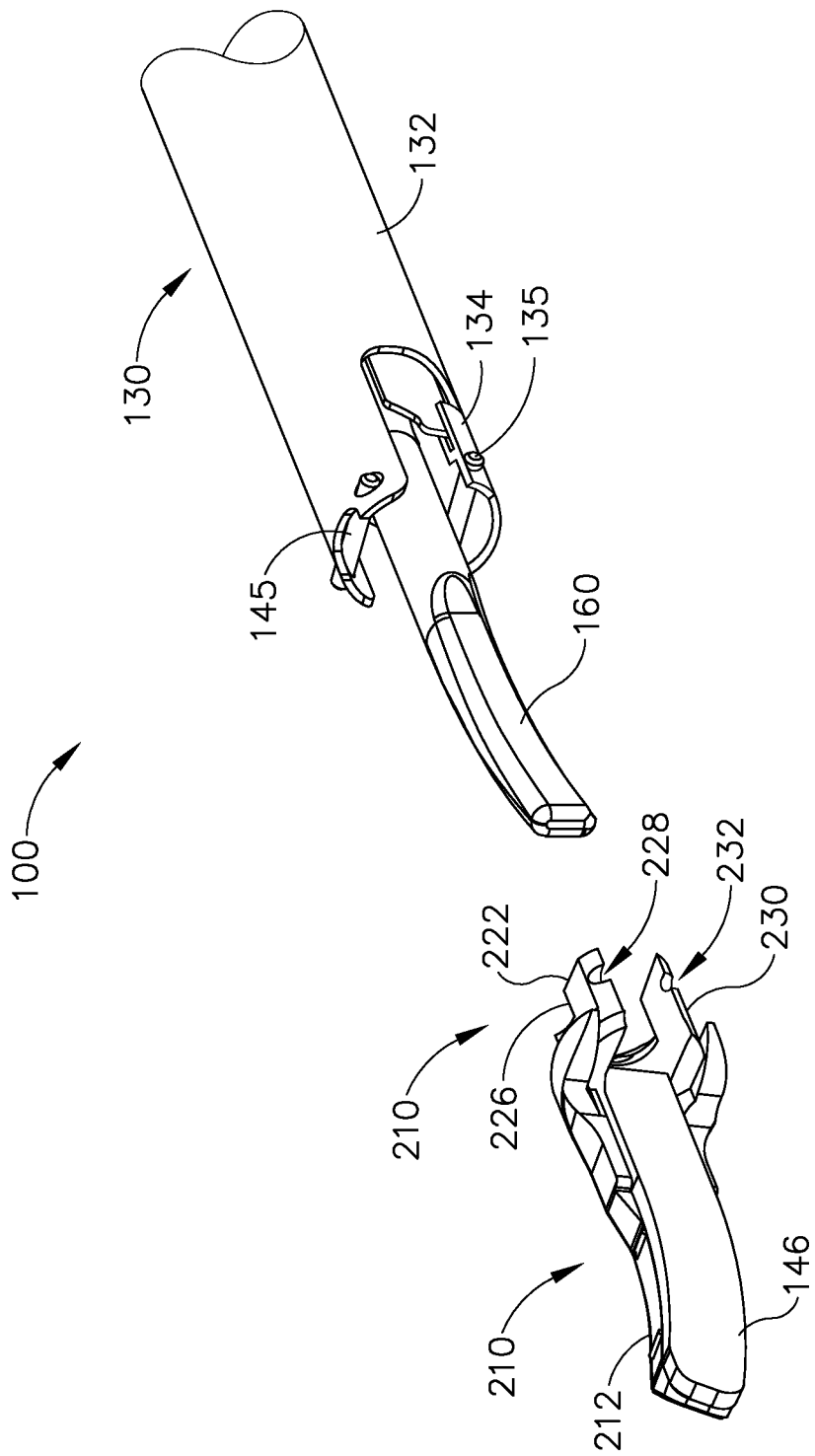
FIG. 12 depicts another perspective view of the clamp arm of FIG. 8, with the clamp arm rotated 90 degrees relative to the instrument of FIG. 2.

To attach clamp arm (210) to instrument (100), an operator may preliminarily rotate clamp arm (210) 90 degrees about the longitudinal axis of clamp arm (210) to a second orientation as shown in FIG. 12. When clamp arm (210) is rotated 90 degrees to the second orientation, each flat face (222, 224) is aligned with a respective pin (145, 135) of instrument (100). It should be understood that when each flat face (222, 224) is so aligned, each flat face (222, 224) is generally parallel with the longitudinal axis of each pin (145, 135). As will be described in greater detail below, such positioning permits coupling member (220) of clamp arm (210) to be inserted between each pin (145, 135).

Figure 13:
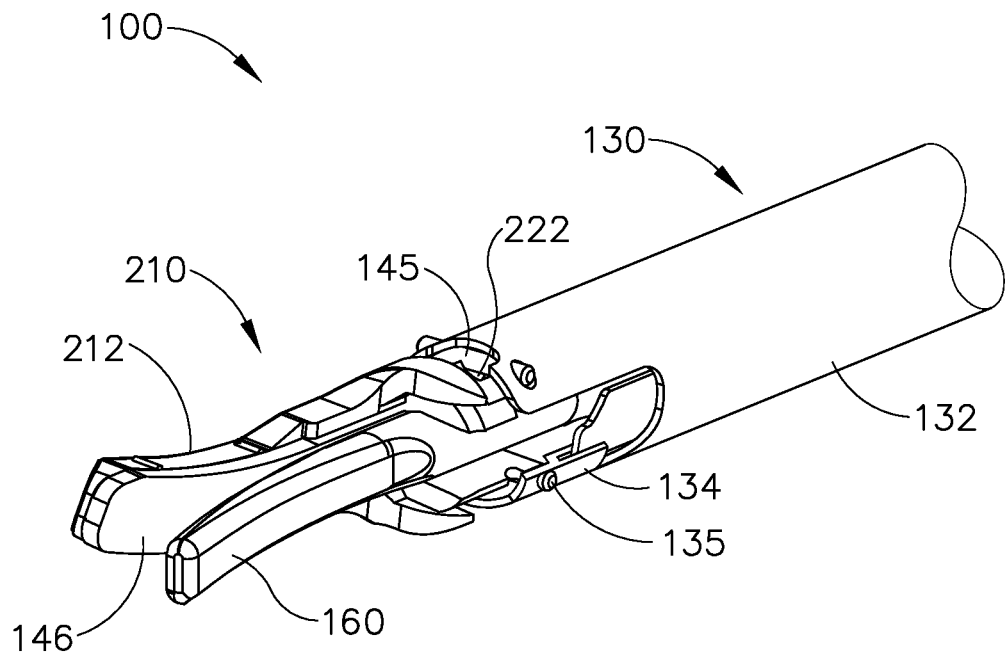
FIG. 13 depicts still another perspective view of the clamp arm of FIG. 8, with the clamp arm inserted onto the instrument of FIG. 2.

Once clamp arm (210) has been rotated about its longitudinal axis 90 degrees to the second orientation, an operator may position coupling member (220) into the position relative to instrument (100) shown in FIG. 13. In this position, coupling member (220) is inserted into the space between each pin (145, 135). As coupling member (220) is inserted into the space between each pin (145, 135), each channel (228, 232) of coupling member (220) is aligned with a respective pin (145, 135) of instrument (100). As will be described in greater detail below, this alignment positions each channel (228, 232) to receive a respective pin (145, 135).

Figure 14:
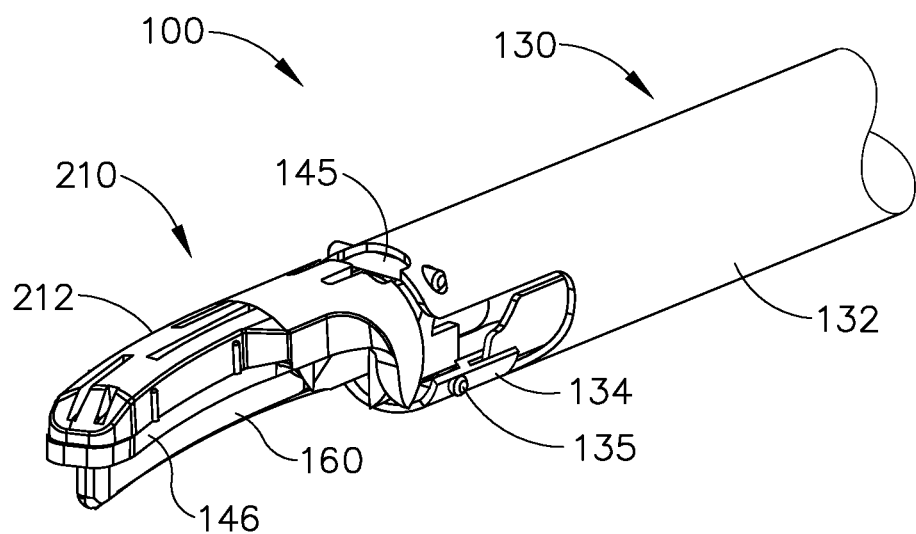
FIG. 14 depicts yet another perspective view of the clamp arm of FIG. 8, with the clamp arm secured to the instrument of FIG. 2.

Once coupling member (220) is inserted into instrument (100), an operator may couple clamp arm (210) to instrument (100) by rotating clamp arm (210). In particular, clamp arm (210) is rotated about its longitudinal axis 90 degrees back to the first orientation, as seen in FIG. 14. Once returned to the first position, coupling member (220) is held in position by engagement between each channel (228, 232) of coupling member (220) and each pin (145, 135) of instrument (100). In particular, because channels (228, 232) open to flat faces (222, 224), pins (145, 135) will be received in a respective channel (228, 232) as clamp arm (210) is rotated relative to instrument (100). Once clamp arm (210) is rotated the full 90 degrees, each pin (145, 135) is disposed in a respective channel (228, 232), thereby resisting any longitudinal movement of clamp arm (210).

Although not shown, it should be understood that outer sheath (132) and/or inner tube (134) of instrument may be modified in some examples to support repeated coupling and decoupling of clamp arm (210). For instance, in some examples inner tube (134) includes an adapter welded or otherwise secured to inner tube (134) to provide additional strength for inner tube (134). In other examples, inner tube (134) and/or outer sheath (132) are increased in thickness (locally or totally) to provide such support. Of course other suitable methods of increasing the strength of instrument (100) to accommodate clamp arm (210) will be apparent to those of ordinary skill in the art in view of the teachings herein.

B. Exemplary Split Clamp Arm

Figure 15:
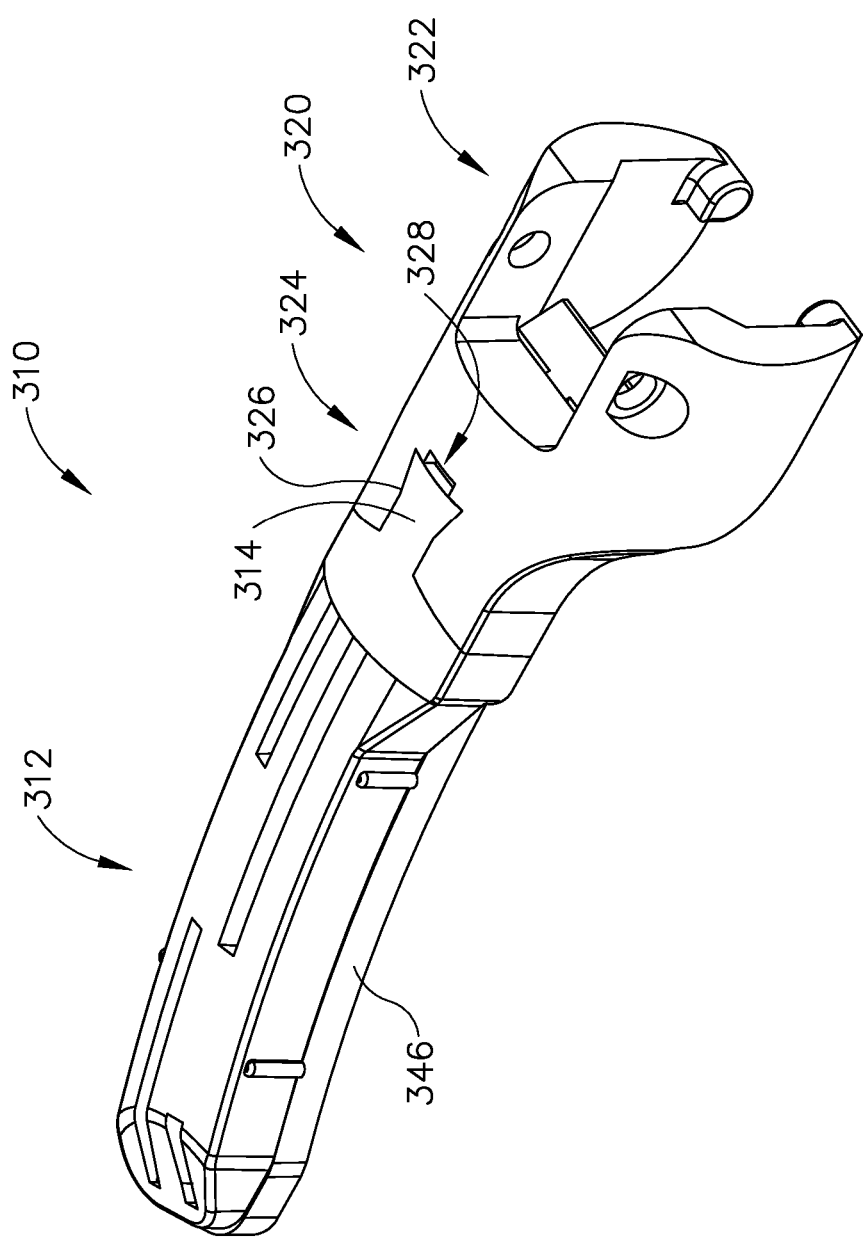
FIG. 15 depicts a perspective view of another exemplary alternative clamp arm for use with the instrument of FIG. 2.
Figure 16:
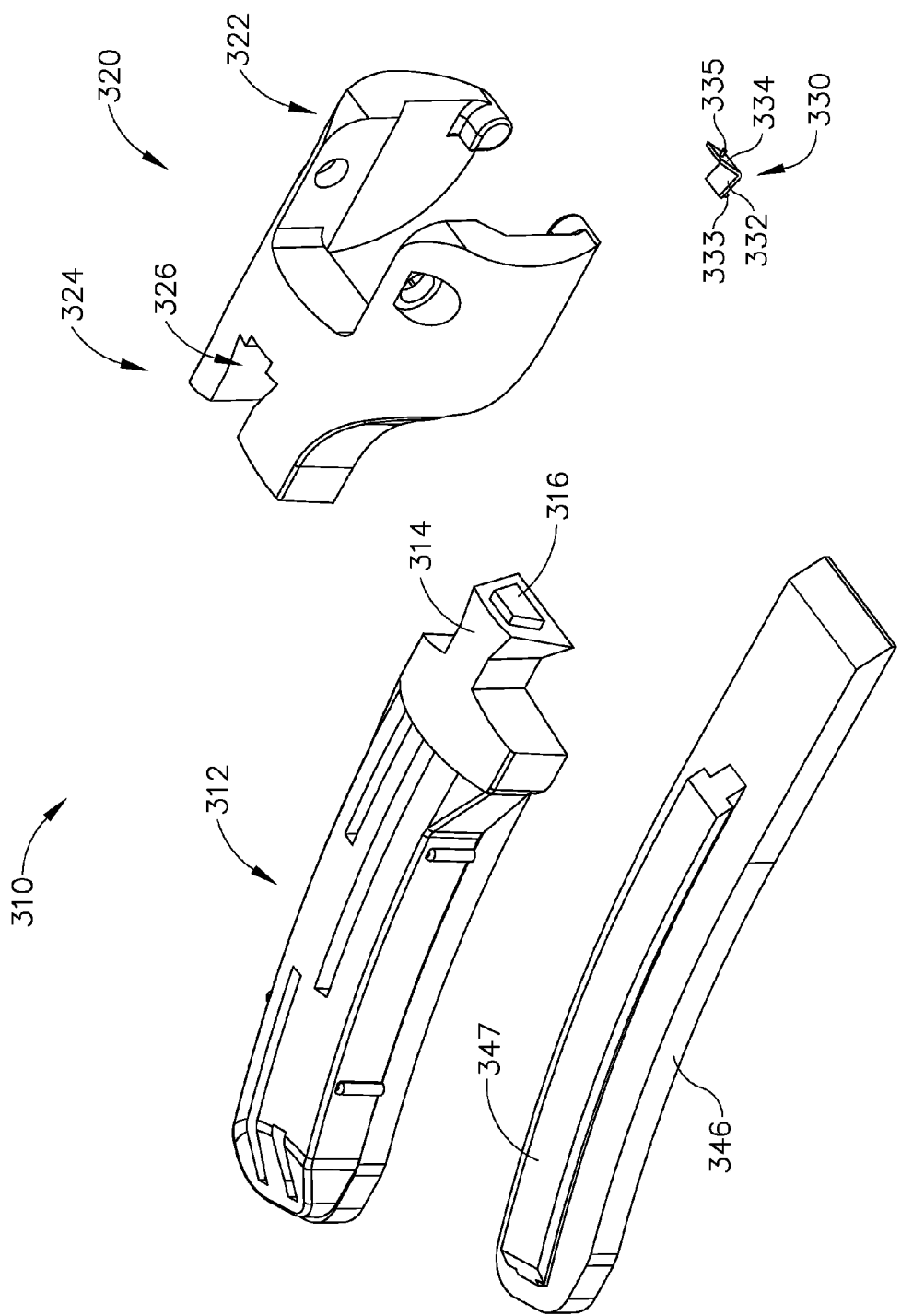
FIG. 16 depicts a perspective exploded view of the clamp arm of FIG. 15.

FIGS. 15 and 16 show another exemplary alternative clamp arm (310) that may be readily incorporated into instrument (100) described above. Clamp arm (310) is substantially the same as clamp arm (144) described above unless otherwise described herein. However, unlike clamp arm (144) described above, clamp arm (310) of the present example is generally selectively separable unto two separate component parts. In particular clamp arm (310) comprises a clamp portion (312), a coupling portion (320), and a fastening member (330).

Clamp portion (312) is generally selectively attachable to coupling portion (220) to form clamp arm (310). Clamp portion (312) of the present example receives a clamp pad (246) similar to clamp pad (146) described above. However, unlike clamp pad (146) described above, clamp pad (346) of the present example includes a t-shaped key (347) instead of a flared key (147). Accordingly, it should be understood that clamp portion (312) includes a channel (not shown) that is shaped to correspond to key (347) such that clamp pad (146) may be inserted into clamp portion (312).

As can best be seen in FIG. 16, clamp portion (312) further includes a proximal attachment member (314). Attachment member (314) extends proximally from clamp portion (312), increasing in width as attachment member (314) extends from clamp portion (312). Attachment member (314) further increases in width from top to bottom. As will be described in greater detail below, attachment member (314) is generally configured to engage with coupling portion (320) such that clamp portion (312) and coupling portion (320) are selectively attachable to each other. While attachment member (314) is shown as having a particular shape, it should be understood that no such limitation is intended and in other examples attachment member (314) has numerous alternative shapes. For instance, in one such example, attachment member (314) is T-shaped. In another example, attachment member (314) is rounded. Of course various other suitable shapes of attachment member (314) will be apparent to those of ordinary skill in the art in view of the teachings herein.

Extending from attachment member (314), clamp portion (312) further includes a lock member (316). Lock member (316) comprises a trapezoidal shape extending proximally from attachment member (314) and having a generally smaller size than attachment member (314). As will be described in greater detail below, lock member (316) is configured to engage with fastening member (330) to securely fasten clamp portion (312) to coupling portion (320).

Coupling portion (320) comprises a proximal coupling member (322) and a distal coupling member (324). Proximal coupling member (322) is configured to couple to shaft assembly (130) of instrument (100) as similarly described above with respect to clamp arm (144). While proximal coupling member (322) is shown and described herein as being configured similarly to the various coupling components of clamp arm (144), it should be understood that in other examples any suitable coupling mechanism may be used in addition to or in lieu of proximal coupling member (322).

Distal coupling member (324) is generally configured to receive attachment member (314) of clamp portion (312). In particular, distal coupling member (324) comprises a first channel (326) and a second channel (328). First channel (326) comprises a shape corresponding to attachment member (314) of clamp portion (312). Thus, first channel (326) is configured to receive attachment member (314) of clamp portion (312) for coupling of clamp portion (312) to coupling portion (320) as will be described in greater detail below.

Second channel (328) comprises a generally rectangular or trapezoidal channel in communication with first channel (326). Second channel (328) is generally configured to receive both lock member (316) of clamp portion (312) and fastening member (330). As will be described in greater detail below, when both lock member (316) and fastening member (330) are received within second channel (328) clamp portion (312) and coupling portion (320) will be securely fastened together. It should be understood that to accommodate both lock member (316) and fastening member (330), second channel (328) is sized generally larger than the combination of lock member (316) and fastening member (330).

Fastening member (330) comprises two resiliently biased leaves (332, 334). Each leaf (332, 334) is of unitary construction with the other and is resiliently biased to form a generally V-shape. At the outermost end of each leaf (332, 334), each leaf (322, 334) comprises a pin (333, 335). In some examples, each pin (333, 335) may comprise a spring loaded bearing or other device to provide at least some additional resilient bias to each leaf (332, 334). As will be described in greater detail below, the resilient bias of each leaf (332, 334) permits fastening member (330) to engage the walls defining second channel (328) and the outer edges of lock member (316) to hold lock member (316) in position relative to coupling portion (320), thereby locking or otherwise securing clamp portion (312) to coupling portion (320).

Figure 17:
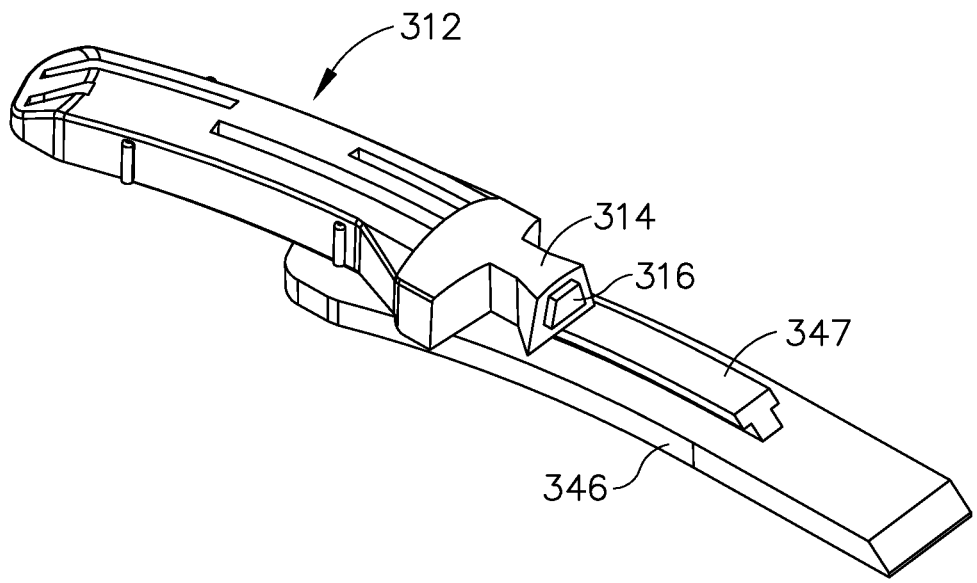
FIG. 17 depicts perspective view of a clamp portion of the clamp arm of FIG. 15, with a clamp pad partially inserted onto the clamp portion.
Figure 18:
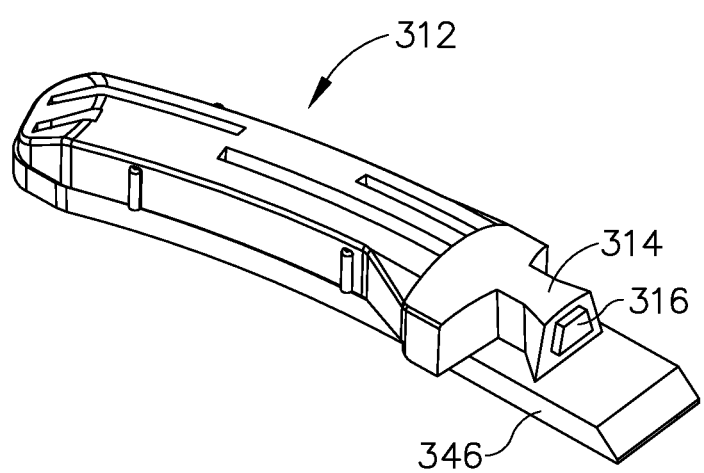
FIG. 18 depicts another perspective view of the clamp portion of FIG. 17, with the clamp pad of FIG. 17 fully inserted onto the clamp portion.

FIGS. 17-21 show an exemplary use of clamp arm (310). In particular, as can be seen in FIG. 17, clamp portion (312) may be initially separated from coupling portion (320). While not shown, it should be understood that at this stage coupling portion (320) may be coupled to instrument (100) via proximal coupling member (322). While clamp portion (312) is uncoupled from coupling portion (320), clamp portion (312) may be readily manipulated by an operator to detach, attach, and/or replace clamp pad (346).

Clamp pad (346) is shown in FIG. 17 as being partially attached to clamp portion (312). To fully attach clamp pad (346) to clamp portion (312) an operator may slide clamp pad (346) relative to clamp portion (312) to the position shown in FIG. 18. Alternatively, an operator may remove clamp pad (346) completely by pulling clamp pad (346) in the opposite direction. An operator may then attach a new clamp pad (346) by following the same progression shown in FIGS. 17 and 18.

Figure 19:
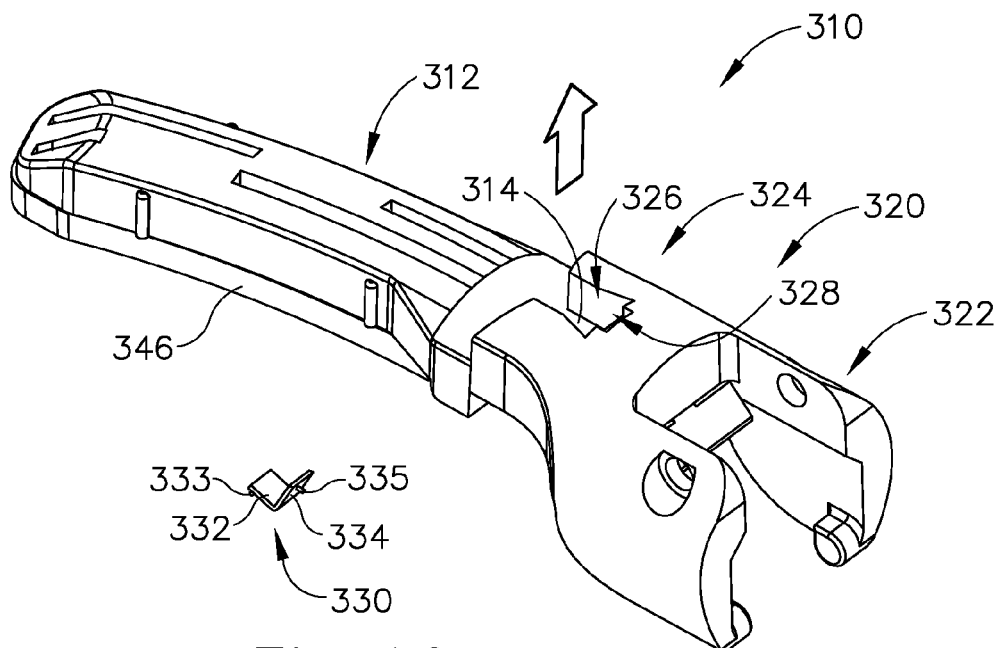
FIG. 19 depicts another perspective view of the clamp portion of FIG. 17, with the clamp portion partially inserted into a body of the clamp arm of FIG. 15.

Once clamp pad (346) is fully attached to clamp portion (312) an operator may begin to attach clamp portion (312) to coupling portion (320). As can be seen in FIG. 19, attachment is initiated by inserting attachment member (314) upwardly into first channel (326) of coupling portion (320). As attachment member (314) is inserted upwardly into first channel (326), engagement occurs between the corresponding shapes of attachment member (314) and first channel (326). Because attachment member (314) is smaller at the top than at the bottom, further upward movement will be prevented once attachment member (314) is fully inserted into first channel (326). Once attachment member (314) is fully inserted into first channel (326), lock member (316) will also correspondingly be inserted into second channel (328). However, it should be understood that at this stage a space will remain between lock member (316) and the walls defining second channel (328) to accommodate fastening member (330).

Figure 21:
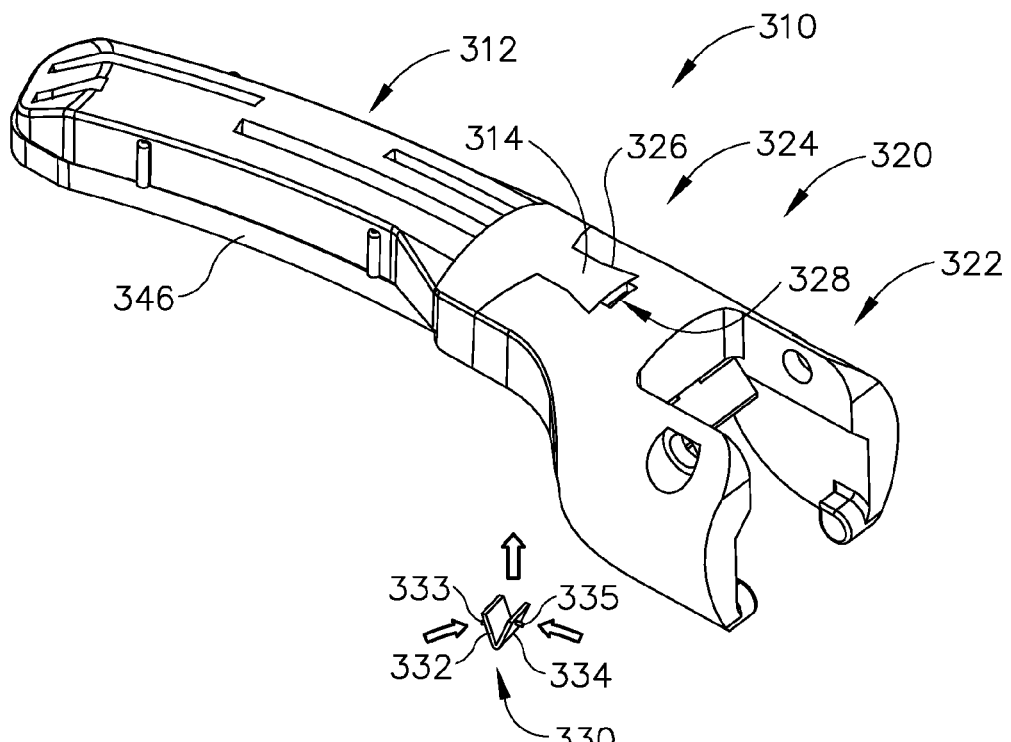
FIG. 21 depicts another perspective view of the clamp arm of FIG. 15, with a fastening member being inserted into the clamp arm.
Figure 22:
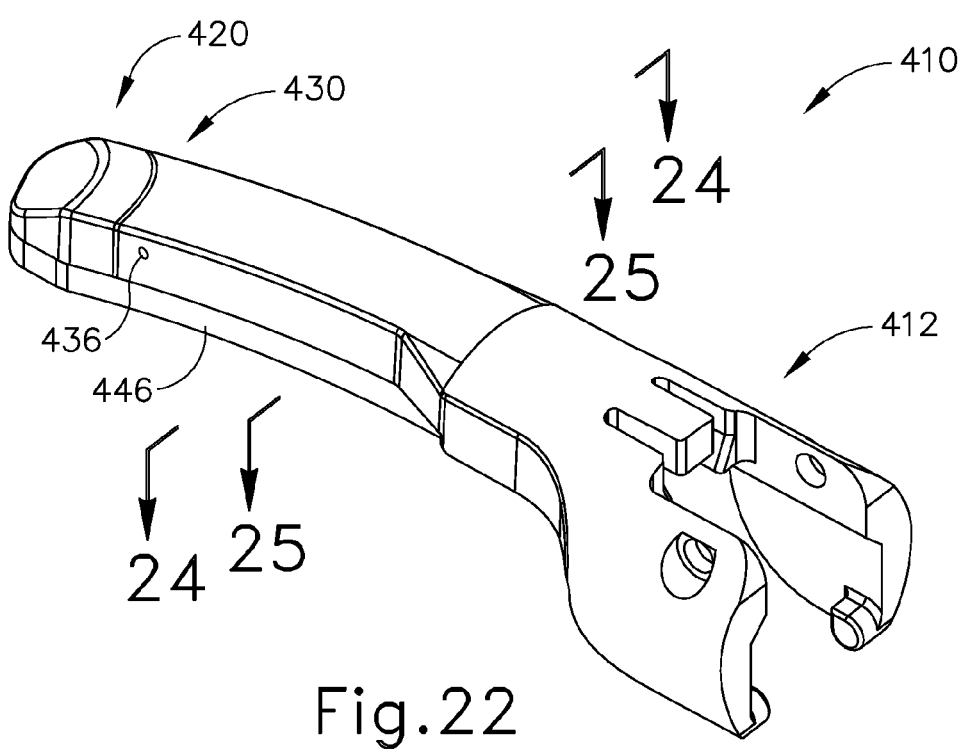
FIG. 22 depicts a perspective view of still another exemplary alternative clamp arm for use with the instrument of FIG. 2.

After attachment member (314) has been fully inserted into first channel (326), clamp portion (312) will still remain free to move downwardly out of first channel (326). Accordingly, an operator may desire to lock or otherwise secure attachment member (314) into position such that clamp portion (312) and coupling portion (320) may act in a unitary fashion. To secure clamp portion (312) to coupling portion (320), an operator may grip fastening member (330) and simultaneously force leaves (332, 334) together while inserting fastening member (330) upwardly and into second channel (228) as shown in FIG. 21. Once fastening member (330) is deployed within second channel (328), leaves (332, 334) will resiliently bear against the walls defining second channel (328) to provide a force that locks or otherwise secures relative motion between lock member (316) and second channel (328).

With clamp portion (312) locked in place relative to coupling portion (320), clamp arm (310) may be used by an operator in conjunction with instrument (100) as described above. At any point during the procedure (or after), should an operator desire to replace or remove clamp pad (346), an operator may remove fastening member (330) and repeat the steps described above in reverse order. If clamp pad (346) is replaced, an operator may continue with the procedure by reattaching clamp portion (312) using the steps described above.

IV. Exemplary Clamp Arms with Removable Tips

In some instances, it may be desirable to provide clamp arms (144) with features configured to allow an operator to selectively remove or otherwise decouple clamp pad (146) from clamp arm (114). One merely exemplary way in which to provide such selective operation to clamp arm (144) is to provide clamp arm (144) with features operable to permit selective removal of at least a portion of clamp arm (144) from itself. Such features may be desirable because such features may permit an operator to more easily remove of clamp pad (146). The examples described below provide various examples of features and techniques configured to allow an operator to selectively remove or otherwise decouple a portion of a clamp arm similar to clamp arm (144). While various examples of features operable to provide such selective operation in clamp arm (144) will be described in greater detail below, other examples will be apparent to those of ordinary skill in the art according to the teachings herein. Similarly, various suitable ways in which the below teachings may be combined with the teachings of the various references cited herein will be apparent to those of ordinary skill in the art.

A. Exemplary Clamp Arm with Removable Tip Having Inner Resilient Tabs

FIGS. 22-25 show still another exemplary alternative clamp arm (410) that may be readily incorporated into instrument (100) described above. Clamp arm (410) is substantially the same as clamp arm (144) described above unless otherwise described herein. However, unlike clamp arm (144) described above, at least a portion of clamp arm (410) is removable to permit removal of a clamp pad (446) from the distal end of clamp arm (410) rather than the proximal end. Clamp arm (410) comprises a body portion (412), a removable distal tip (420), and a distal attachment portion (430). Body portion (412) is configured to be pivotably coupled to instrument (100) and is generally the same as clamp arm (144) described above such that further details will not be described herein.

Figure 23:
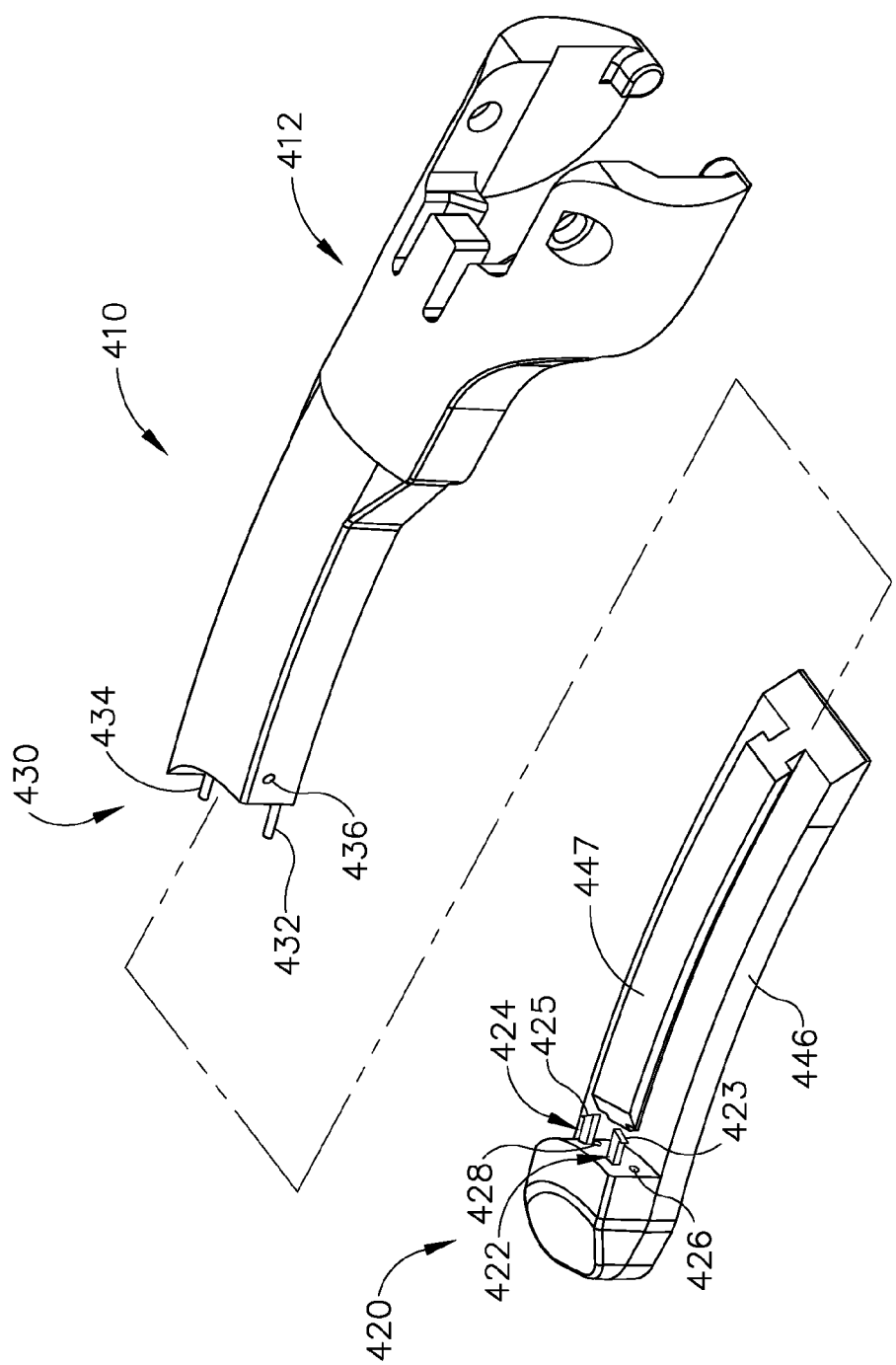
FIG. 23 depicts an exploded perspective view of the clamp arm of FIG. 22.

As can best be seen in FIG. 23, distal tip (420) comprises two resilient tabs (422, 424) and two bores (426, 428) disposed on the proximal face of distal tip (420). Each tab (422, 424) extends proximally from the proximal end of distal tip (420). Each resilient tab (422, 424) defines a tooth (423, 425) at the proximal end of each resilient tab (422, 424). Although each tooth (423, 425) is shown as being generally triangular in shape, it should be understood that any suitable shape may be used. For instance, in some examples teeth (423, 425) incorporate rounded protrusions or detent features. As will be described in greater detail below, each tooth (423, 425) is generally configured to engage at least a portion of distal attachment portion (430) to selectively secure distal tip (420) to distal attachment portion (430). While the present example is shown as including two resilient tabs (422, 424), it should be understood that in other examples any suitable number of resilient tabs (422, 424) may be used.

Bores (426, 428) of distal tip (420) extend through at least a portion of distal tip (420), although not through all of distal tip (420). Each bore (426, 428) is disposed below a corresponding resilient tab (422, 424). In other examples, bores (426, 428) are disposed in any other suitable location. In still other examples, any suitable number of bores (426, 428) may be used, with bores (426, 428) even being omitted entirely. As will be described in greater detail below, each bore (426, 428) is generally configured to receive a portion of distal attachment portion (430) to provide lateral stability to distal tip (420) when secured to distal attachment portion (430).

Distal tip (420) is secured to a clamp pad (446) such that clamp pad (446) and distal tip (420) form a unitary part. In the present example, distal tip (420) comprises a metal alloy, while clamp pad (446) comprises a polymer such as polytetrafluoroethylene (PTFE). Accordingly, it should be understood that in the present example distal tip (420) and clamp pad (446) are joined by a suitable method for joining dissimilar materials such as adhesive bonding. Of course, in examples where distal tip (420) and clamp pad (446) comprise similar materials, the particular method of joining may be varied accordingly.

Clamp pad (446) is substantially the same as clamp pad (146) described above. However, unlike clamp pad (146), clamp pad (446) comprises a T-shaped key (447) that extends for only a portion of clamp pad (446). In particular, key (447) stops short of distal tip (420) to accommodate resilient tabs (422, 424). It should be understood that resilient tabs (422, 424) of the present example are disposed at a height that is generally the same as the maximum height of key (447). Accordingly, key (447) extends generally to the point where resilient tabs (422, 424) end. In other examples, tabs (422, 424) may be alternatively positioned to permit key (447) to extend distally to distal tip (420).

Like with key (147) described above, key (447) is configured to engage with a channel (440) of a corresponding shape such that channel (440) secures clamp pad (446) to clamp arm (410). As will be described in greater detail below, channel (440) is integrated into body (412), extending the length of body (412) through distal attachment portion (430). Thus, channel (440) is exposed at distal attachment portion (430) such that key (447) may be inserted into distal attachment portion (430) from the distal end of clamp arm (410).

Figure 25:
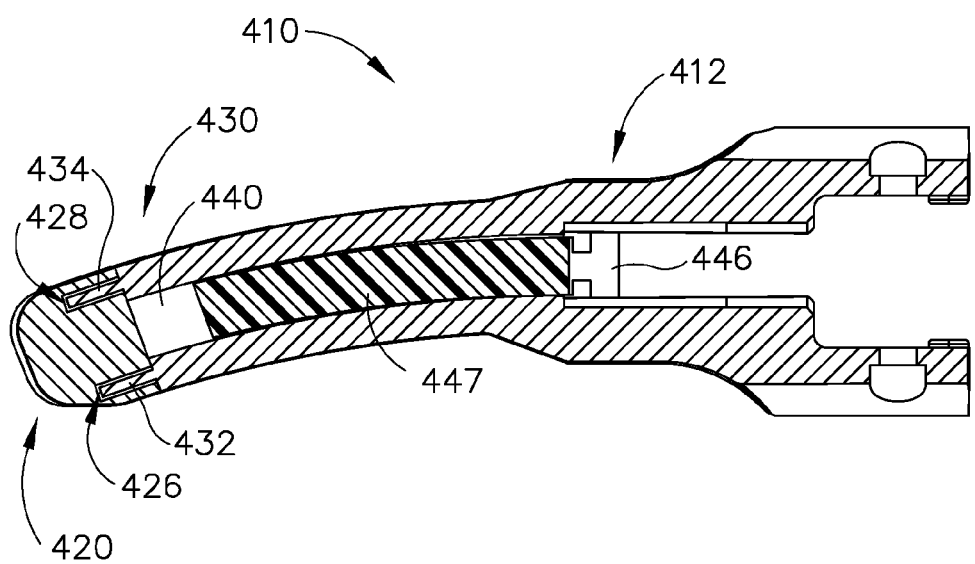
FIG. 25 depicts another top cross-sectional view of the clamp arm of FIG. 22, the cross-section taken along line 25-25 of FIG. 22.

Distal attachment portion (430) comprises two stabilizing members (432, 434), and a release bore (436) extending transversely through distal attachment portion (430). Each stabilizing member (432, 434) is configured and positioned to be received by bores (426, 428) of distal tip (420). When stabilizing members (432, 434) are received within bores (426, 428) (as shown in FIG. 25), stabilizing members (432, 434) are generally configured to enhance the lateral stability of distal tip (420).

Release bore (436) is positioned to extend through channel (440) that extends from body (412) through distal attachment portion (430). As will be described in greater detail below, release bore (436) is configured to receive at least a portion of a detachment tool (not shown) such as an elongate rod. When detachment tool (480) is received therein, release bore (436) is positioned such that at least a portion of detachment tool (480) can engage with resilient tabs (422, 424) of distal tip (420) for disengagement.

Figure 24:
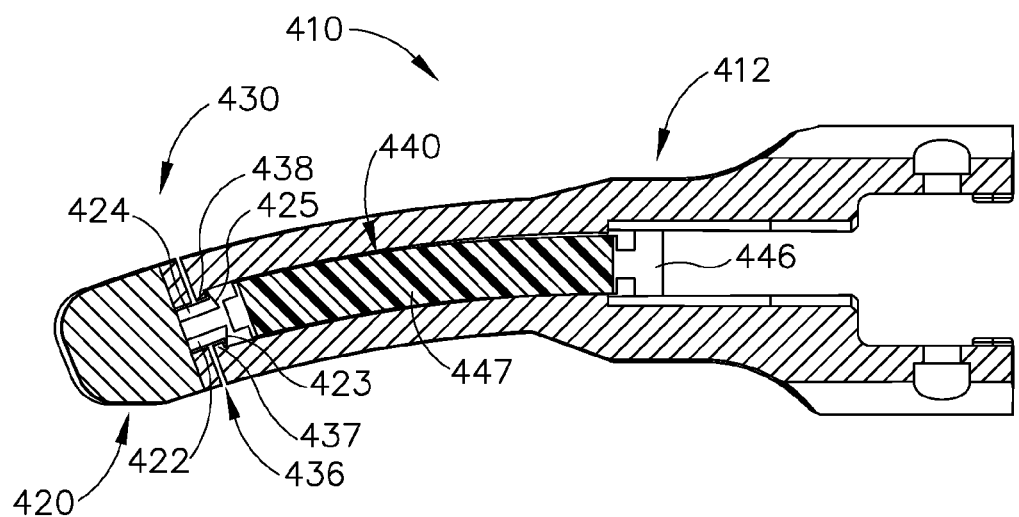
FIG. 24 depicts a top cross-sectional view of the clamp arm of FIG. 22, the cross-section taken along line 24-24 of FIG. 22.

As can be seen in FIG. 24, channel (440) extends through distal attachment portion (430). However, distal attachment portion (430) further includes two retaining features (437, 438) extending inwardly into channel (440). Retaining features (437, 438) of the present example are configured to engage with teeth (423, 425) of distal tip (420) to selectively couple distal tip (420) to distal attachment portion (430). Although retention features (437, 438) of the present example extend into channel (440) it should be understood that such extension is not significant enough to prevent insertion of key (447) of clamp pad (446). In other words, key (447) of clamp pad (446) is not substantially encumbered from being inserted into channel (440) through distal attachment feature (430).

Figure 26:
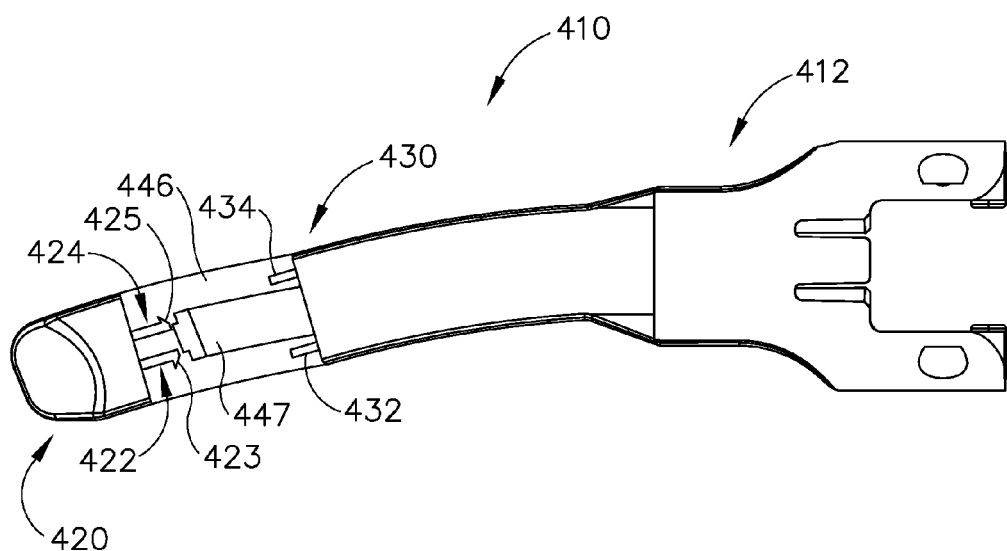
FIG. 26 depicts a top plan view of the clamp arm of FIG. 22, with a clamp pad partially inserted into the clamp arm.
Figure 27:
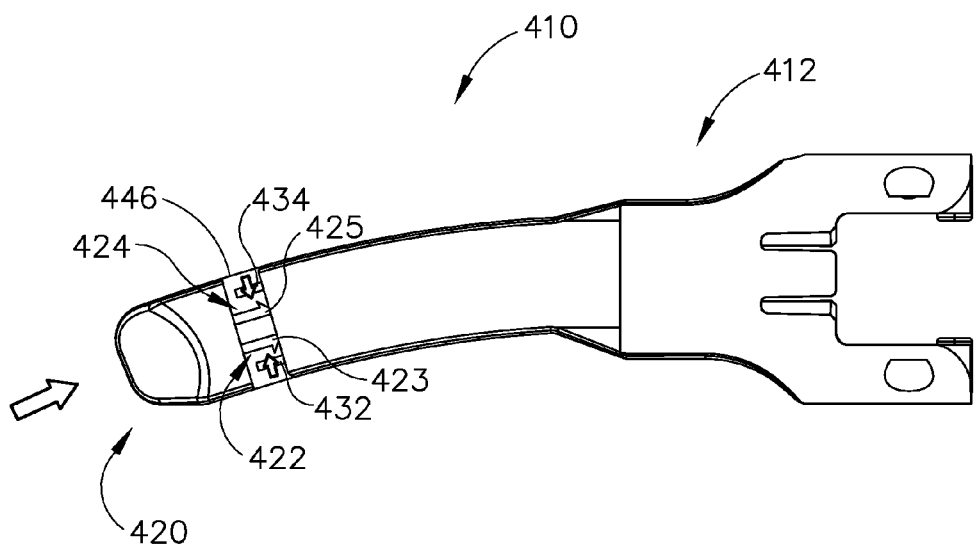
FIG. 27 depicts another top plan view of the clamp arm of FIG. 22, with a distal tip of the clamp arm engaging a distal attachment portion of the clamp arm.
Figure 28:
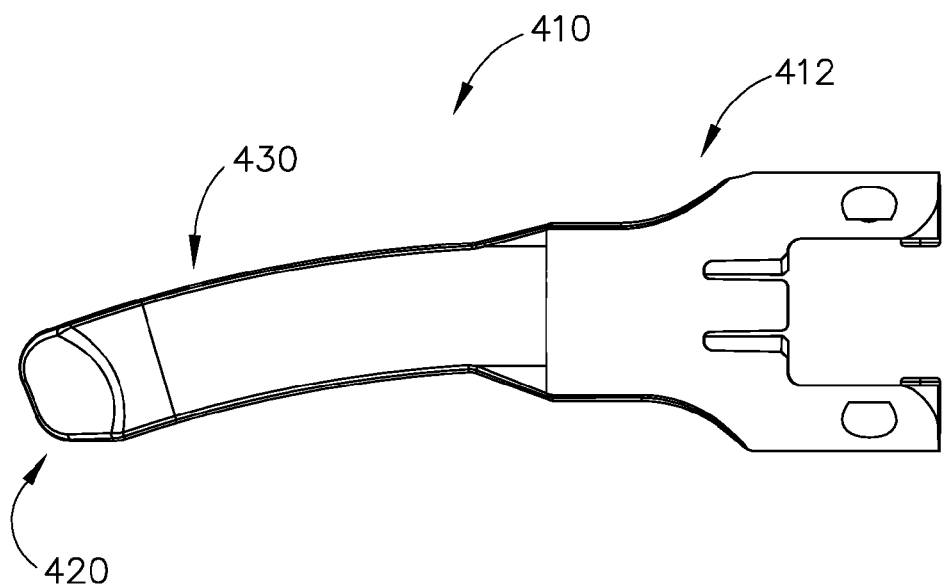
FIG. 28 depicts still another top plan view of the clamp arm of FIG. 22, with the distal tip of FIG. 27 fully engaged with the distal attachment portion of FIG. 27.
Figure 29:
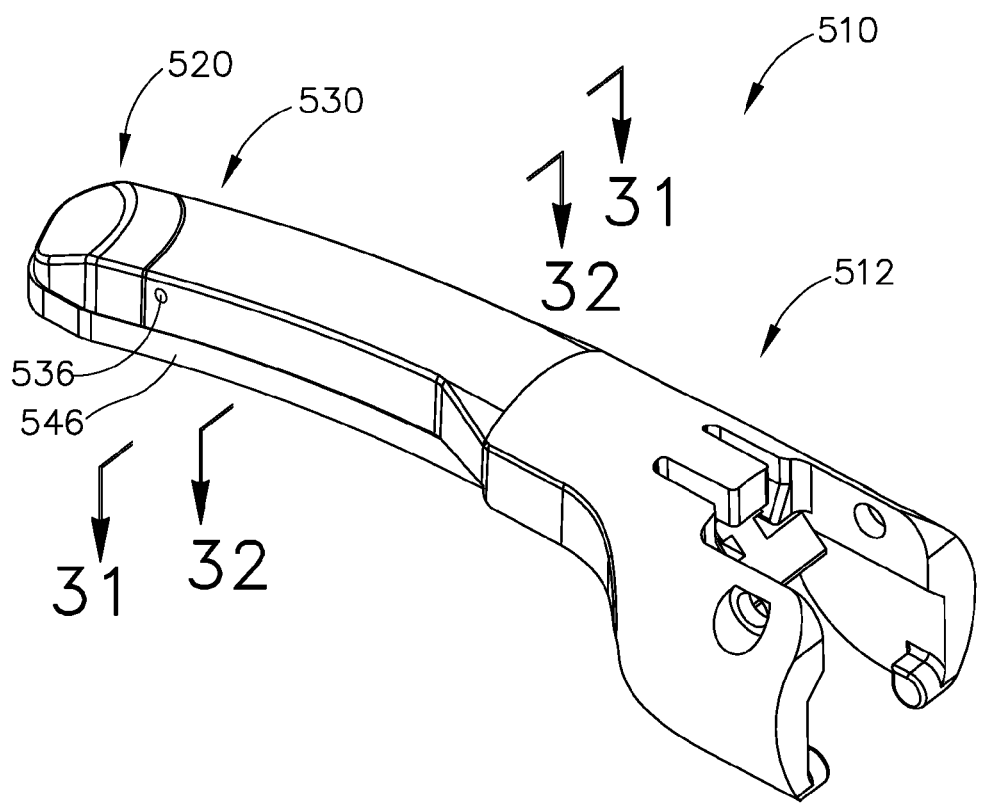
FIG. 29 depicts a perspective view of yet another exemplary alternative clamp arm for use with the instrument of FIG. 2.

FIGS. 26-28 show an exemplary use of clamp arm (410) to prepare clamp arm (410) for use in a surgical procedure. Initially, distal tip (420) and clamp pad (446) may be detached from body (412) of clamp arm (410). As can be seen in FIG. 26, key (447) of clamp pad (446) is initially inserted into channel (440). An operator may slide clamp pad (446) proximally relative to body (412) of clamp arm (410) until clamp pad (446) reaches the position in FIG. 27.

Once clamp pad (446) reaches the position shown in FIG. 27, distal tip (420) will begin to engage distal attachment portion (430). In particular, teeth (423, 425) of each resilient tab (422, 424) will begin to engage retaining features (437, 438) of distal attachment portion (430). As clamp pad (446) is advanced further proximally, the triangular shape of each tooth (423, 425) will slide against retaining features (437, 438) pushing each resilient tab (422, 424) laterally inwardly. Even further proximal advancement of clamp pad (446) will eventually lead to teeth (423, 425) snapping into position relative to retaining features (437, 438) as shown in FIG. 24. Such positioning of teeth (423, 425) corresponds to distal tip (420) and clamp pad (446) being positioned as shown in FIG. 28.

Once teeth (423, 425) are in the position shown in FIG. 24 and distal tip (420) and clamp pad (446) are in the position shown in FIG. 28, distal tip (420) is attached to distal attachment portion (430). Accordingly, clamp pad (446) is correspondingly locked in position and clamp arm (410) is in a state for the performance of a surgical procedure using instrument (100) as described above.

Optionally, an operator may desire to remove clamp pad (446) to replace clamp pad (446) with another different clamp pad or a clamp pad identical to clamp pad (446). Although not shown, it should be understood that an operator may insert a detachment tool (not shown) into release bore (436) to disengage distal tip (420) from distal attachment portion (430). By way of example only, the detachment tool may comprise any suitable device such as an elongate rod. Once the detachment tool is inserted into release bore (436), the detachment tool may be used by an operator to manipulate resilient tabs (422, 424). To release distal tip (420) from attachment portion (430), resilient tabs (422, 424) are manipulated to move teeth (423, 425) out of engagement with retaining features (437, 438). Once teeth (424, 425) have been moved out of engagement with retaining features (437, 438), an operator may pull distal tip (420) and clamp pad (446) distally to decouple distal tip (420) and clamp pad (446) from body (412) of clamp arm (410). The procedure described above may then be repeated by an operator to couple a new clamp pad (446) to clamp arm (410).

B. Exemplary Clamp Arm with Removable Tip Having Dowel Attachment

FIGS. 29-32 show yet another exemplary alternative clamp arm (510) that may be readily incorporated into instrument (100) described above. Clamp arm (510) is substantially the same as clamp arm (144) described above unless otherwise described herein. However, unlike clamp arm (144) described above, at least a portion of clamp arm (510) is removable to permit removal of a clamp pad (546) from the distal end of clamp arm (510) rather than the proximal end. Clamp arm (510) comprises a body portion (512), a removable distal tip (520), and a distal attachment portion (530). Body portion (512) is configured to be pivotably coupled to instrument (100) and is generally the same as clamp arm (144) described above such that further details will not be described herein.

Figure 30:
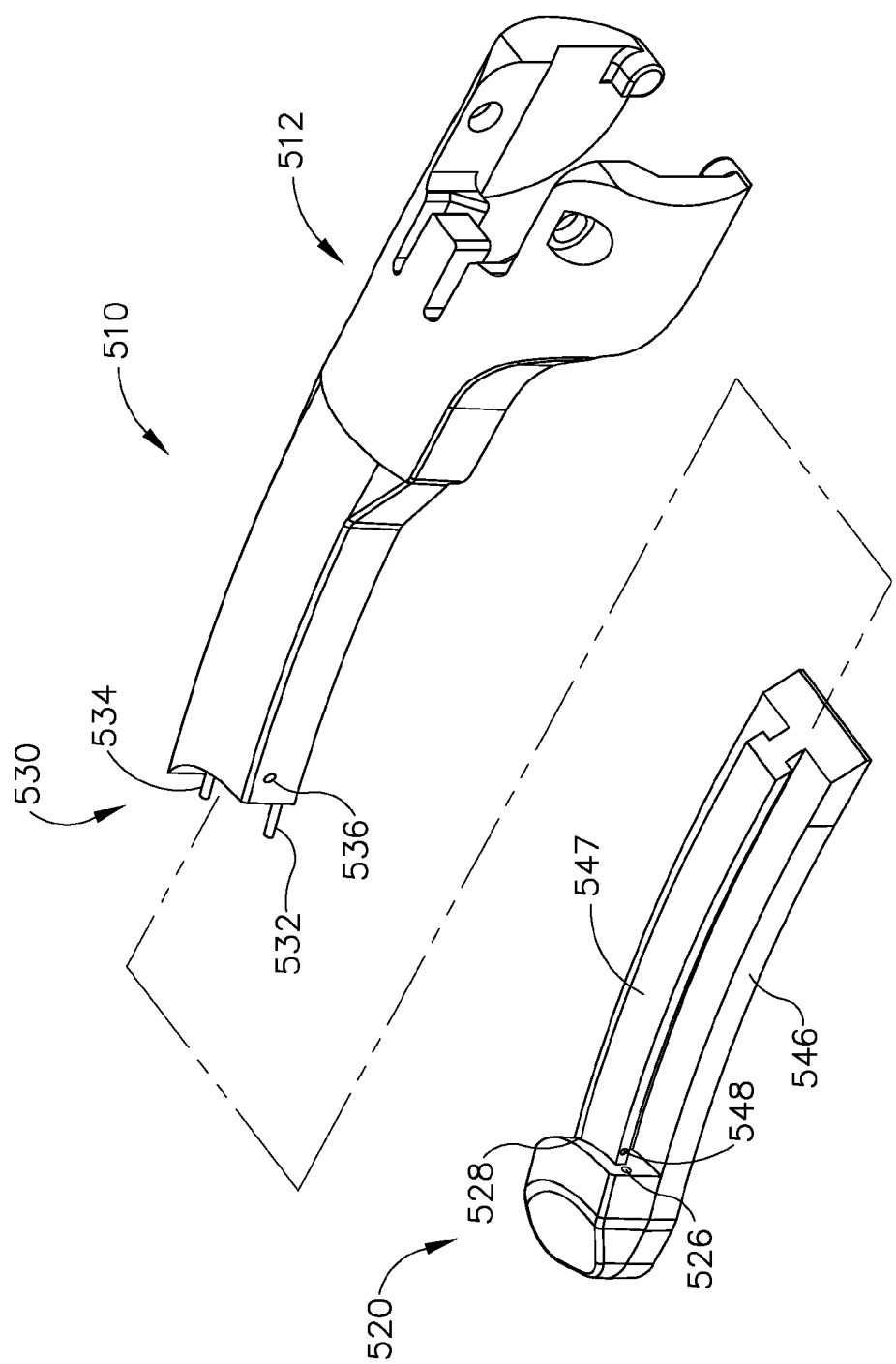
FIG. 30 depicts a perspective exploded view of the clamp arm of FIG. 29.

As can best be seen in FIG. 30, distal tip (520) comprises two bores (526, 528) disposed on the proximal face of distal tip (520). Bores (526, 528) of distal tip (520) extend through at least a portion of distal tip (520), although not through all of distal tip (520). Each bore (526, 528) is disposed directly above clamp pad (546). In other examples, bores (526, 528) are disposed in any other suitable location. In still other examples, any suitable number of bores (526, 528) may be used, with bores (526, 528) even being omitted entirely. As will be described in greater detail below, each bore (526, 528) is generally configured to receive a portion of distal attachment portion (530) to provide lateral stability to distal tip (520) when secured to distal attachment portion (530).

Distal tip (520) is secured to a clamp pad (546) such that clamp pad (546) and distal tip (520) form a unitary part. In the present example, distal tip (520) comprises a metal alloy, while clamp pad (546) comprises a polymer such as polytetrafluooroethylene (PTFE). Accordingly, it should be understood that in the present example distal tip (520) and clamp pad (546) are joined by a suitable method for joining dissimilar materials such as adhesive bonding. Of course, in examples where distal tip (520) and clamp pad (546) comprise similar materials, the particular method of joining may be varied accordingly.

Clamp pad (546) is substantially the same as clamp pad (146) described above. However, unlike clamp pad (146), clamp pad (546) comprises a T-shaped key (547) that extends for only a portion of clamp pad (546). In particular, key (547) stops at the proximal face of distal tip (520). Clamp pad (546) further comprises an attachment bore (548). Attachment bore (548) of the present example is disposed in the uppermost distal corner of key (547), although in other examples attachment bore (548) is disposed in other positions. As will be described in greater detail below, attachment bore (548) is configured to receive an attachment pin (550) to prevent longitudinal movement of distal tip (520) and clamp pad (546) relative to body (512) of clamp arm (510).

Like with key (147) described above, key (547) is configured to engage with a channel (540) of a corresponding shape such that channel (540) secures clamp pad (546) to body (512) of clamp arm (510). As will be described in greater detail below, channel (540) is integrated into body (512), extending the length of body (512) through distal attachment portion (530). Thus, channel (540) is exposed at distal attachment portion (530) such that key (547) may be inserted into distal attachment portion (530) from the distal end of clamp arm (510).

Figure 32:
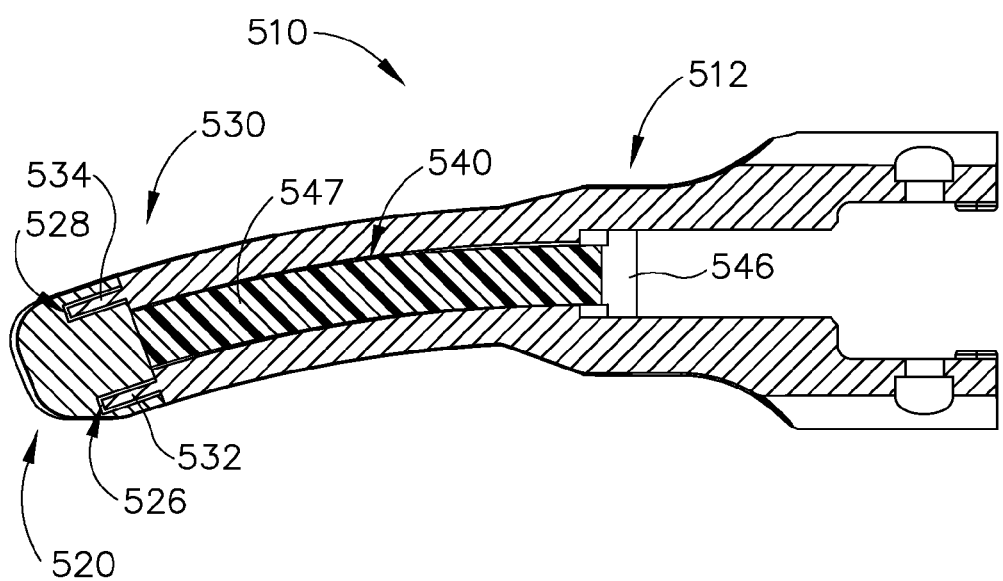
FIG. 32 depicts another top cross-sectional view of the clamp arm of FIG. 29, the cross-section taken along line 32-32 of FIG. 29.

Distal attachment portion (530) comprises two stabilizing members (532, 534), and an attachment bore (536) extending transversely through distal attachment portion (530). Each stabilizing member (532, 534) is configured and positioned to be received by bores (526, 528) of distal tip (520). When stabilizing members (532, 534) are received within bores (526, 528) (as shown in FIG. 32), stabilizing members (532, 534) are generally configured to enhance the lateral stability of distal tip (520).

Figure 31:
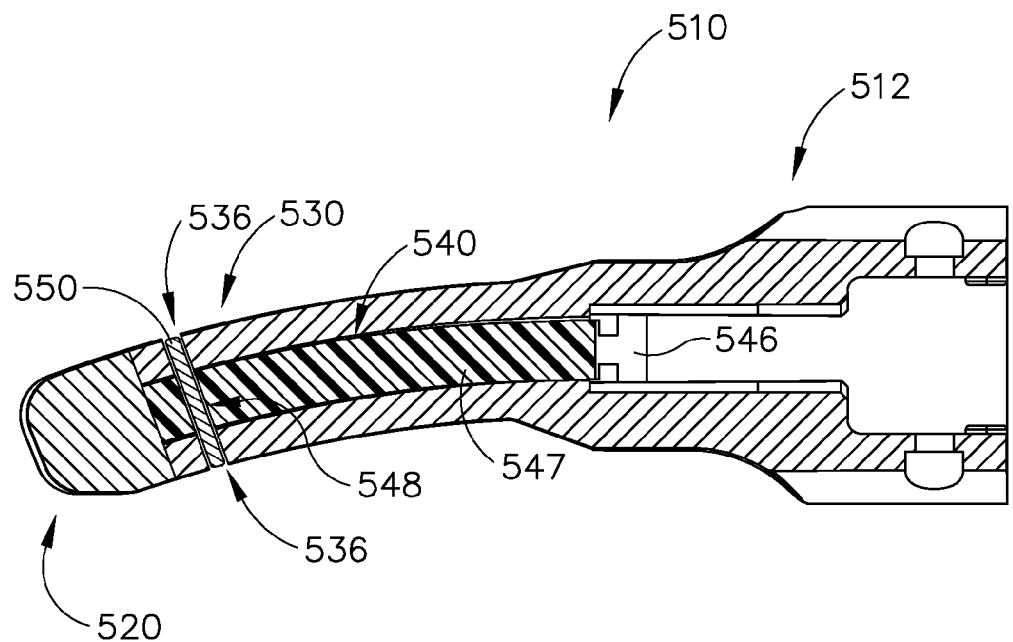
FIG. 31 depicts a top cross-sectional view of the clamp arm of FIG. 29, the cross-section taken along line 31-31 of FIG. 29.

Attachment bore (536) of distal attachment portion (530) is positioned to extend through channel (540) that extends from body (512) through distal attachment portion (530). Attachment bore (536) is further positioned to align with attachment bore (548) of clamp pad (546) when clamp pad (546) is fully inserted into channel (540). As can be seen in FIG. 31, attachment bore (536) of distal attachment portion (530) is configured to receive attachment pin (550) such that attachment pin (550) extends through attachment bore (536) of distal attachment portion (530) and into attachment bore (548) of clamp pad (546). As will be described in greater detail below, receipt of attachment pin (550) into both bores (536, 548) prevents longitudinal movement of clamp pad (546) relative to body (512) of clamp arm (510).

Figure 33:
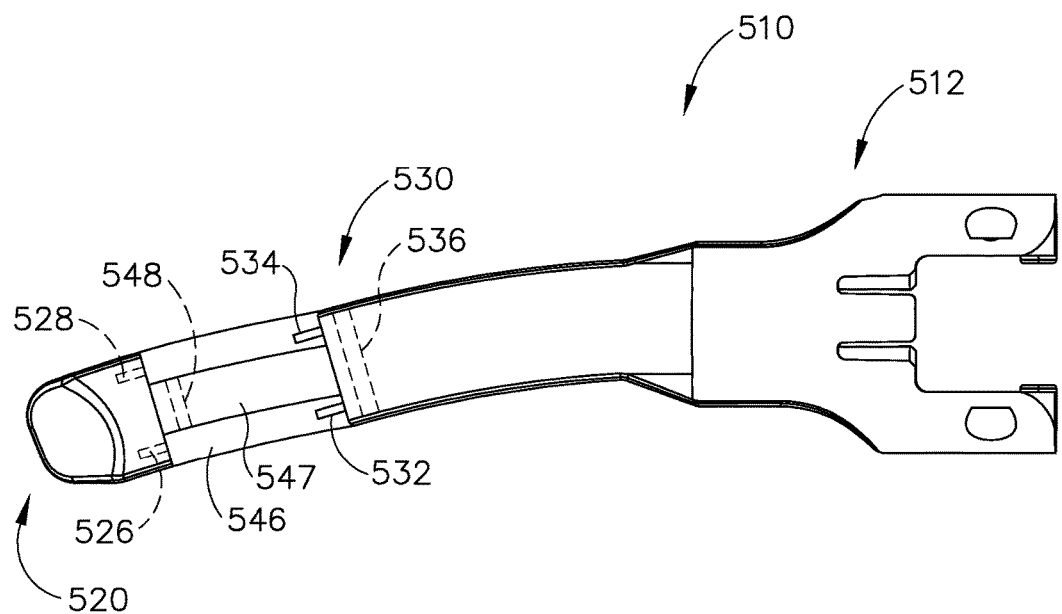
FIG. 33 depicts a top plan view of the clamp arm of FIG. 29, with a clamp pad partially inserted into the clamp arm.

FIGS. 33-38 show an exemplary use of clamp arm (510) to prepare clamp arm (510) for use in a surgical procedure. Initially, distal tip (520) and clamp pad (546) may be detached from body (512) of clamp arm (510). As can be seen in FIG. 33, key (547) of clamp pad (546) is initially inserted into channel (440). An operator may slide clamp pad (546) proximally relative to body (512) of clamp arm (510) until clamp pad (546) reaches the position in FIG. 34.

Figure 34:
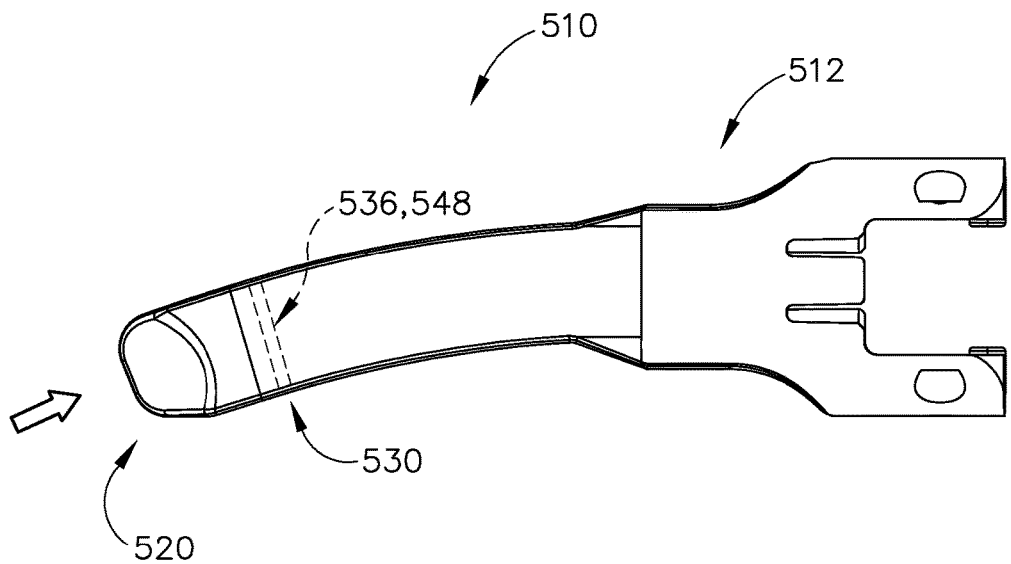
FIG. 34 depicts another top plan view of the clamp arm of FIG. 29, with the clamp pad of FIG. 33 fully inserted into the clamp arm.

Once clamp pad (546) reaches the position shown in FIG. 34, the proximal face of distal tip (520) is directly adjacent to the distal face of distal attachment portion (530). In this position, attachment bore (548) of clamp pad (546) is generally aligned with attachment bore (536) of distal attachment portion (530). Accordingly, attachment bores (536, 548) are positioned relative to each other such that pin (550) may be received through both bores (536, 548).

Figure 35:
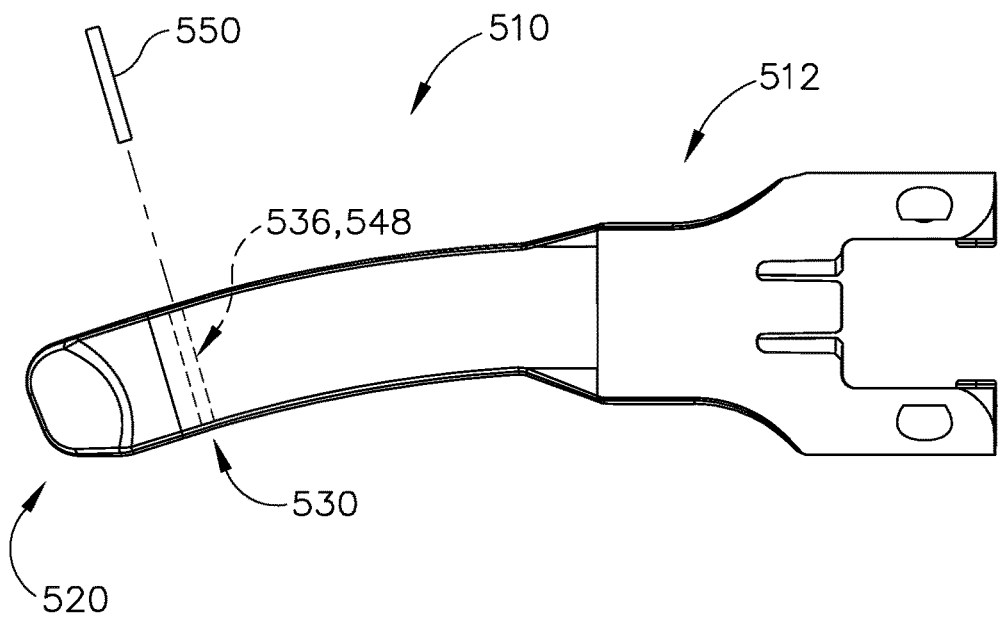
FIG. 35 depicts still another top plan view of the clamp arm of FIG. 29, with a pin adjacent to a bore of the clamp arm.
Figure 36:
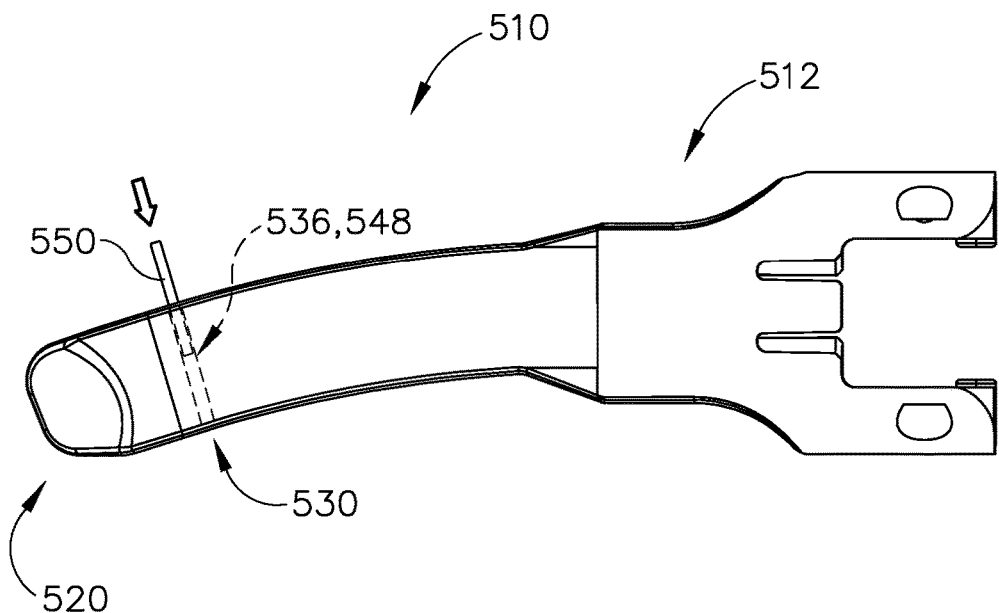
FIG. 36 depicts yet another top plan view of the clamp arm of FIG. 29, with the pin of FIG. 35 partially inserted into the bore of FIG. 35.

As can be seen in FIGS. 35 and 36, an operator may next grasp pin (550) and insert pin (550) into attachment bore (536) of distal attachment portion (530). Further insertion of attachment pin (550) will cause attachment pin (550) to engage attachment bore (548) of clamp pad (546) and then again engage attachment bore (536) of distal attachment portion (530). Such positioning of attachment pin (550) is shown in phantom in FIG. 37 and in cross section in FIG. 31. In this position, distal tip (520) and clamp pad (546) are secured to distal attachment portion (530) and the surgical procedure described above with respect to instrument (100) may be performed using clamp arm (510).

Figure 37:
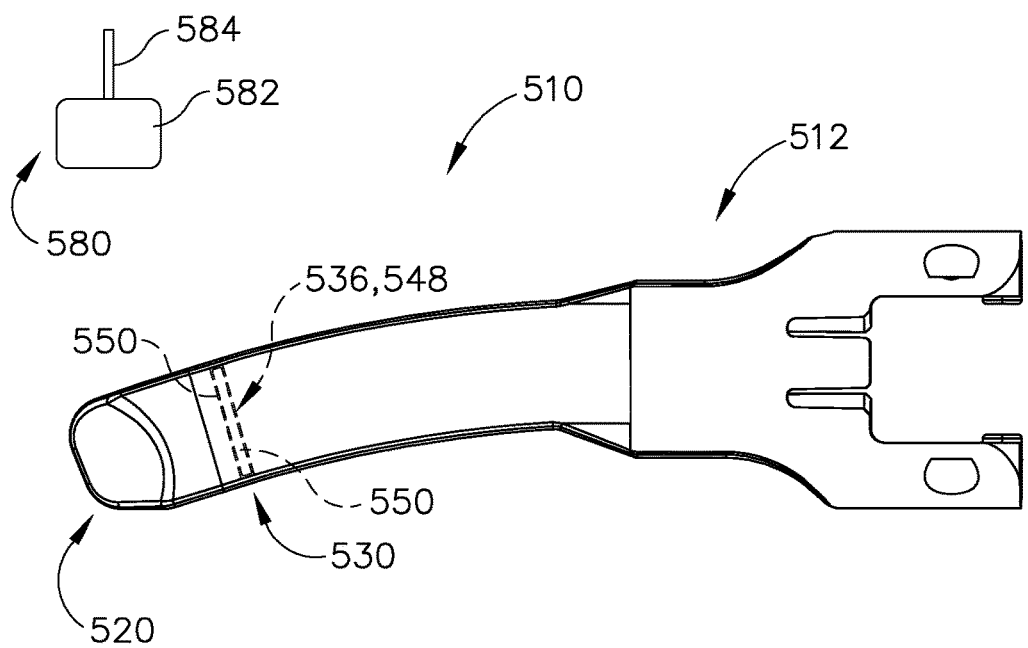
FIG. 37 depicts yet another top plan view of the clamp arm of FIG. 29, with the pin of FIG. 35 fully inserted into the bore of FIG. 35.

Optionally, an operator may desire to remove clamp pad (546) to replace clamp pad (546) with another different clamp pad or a clamp pad identical to clamp pad (546). To decouple clamp pad (546) from body (512) of clamp arm (510) an operator may first acquire a detachment tool (580), as shown in FIG. 37. As can be seen, detachment tool (580) comprises a handpiece (582) and an engagement member (584). Engagement member (584) of the present example generally corresponds to the size and shape of attachment pin (550) such that engagement member (584) may be used by an operator to displace attachment pin (550).

Figure 38:
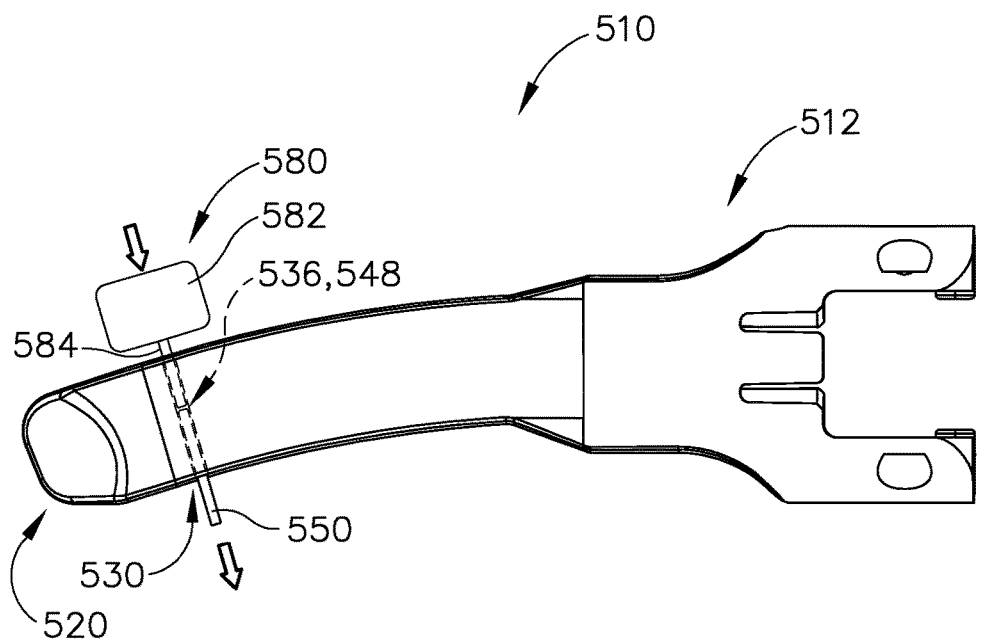
FIG. 38 depicts yet another top plan view of the clamp arm of FIG. 29, with the pin of FIG. 35 being ejected from the bore of FIG. 35 using a tool.
Figure 39:
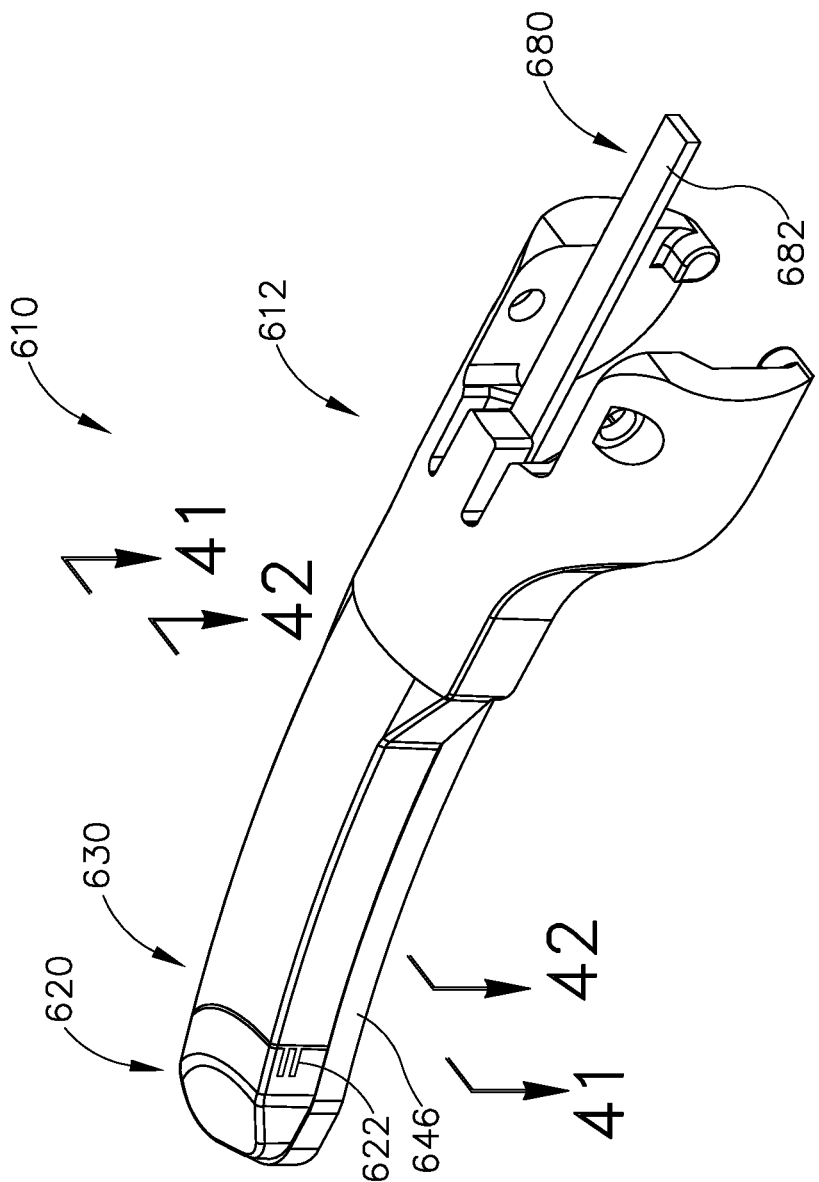
FIG. 39 depicts a perspective view of yet another clamp arm for use with the instrument of FIG. 2.

As can be seen in FIG. 38, an operator may grasp handpiece (582) of detachment tool (580) and manipulate engagement member (584) into alignment with attachment bore (536) of distal attachment portion (530). Next, an operator may push engagement member (584) into attachment bore (536). As an operator pushes engagement member (584) into attachment bore (536), engagement member (584) will displace attachment pin (550) until attachment pin (550) is forced out of both attachment bores (536, 548) completely.

With attachment pin (550) removed, an operator may removed engagement member (584) from attachment bores (536, 548), thereby releasing relative longitudinal movement between clamp pad (546) and body (512) of clamp arm (510). An operator may then pull distal tip (520) and clamp pad (546) distally to decouple distal tip (520) and clamp pad (546) from body (512) of clamp arm (510). The procedure described above may then be repeated by an operator to couple a new clamp pad (546) to clamp arm (510).

C. Exemplary Clamp Arm with Removable Tip Having Outer Resilient Tabs

FIGS. 39-42 show yet another exemplary alternative clamp arm (610) that may be readily incorporated into instrument (100) described above. Clamp arm (610) is substantially the same as clamp arm (144) described above unless otherwise described herein. However, unlike clamp arm (144) described above, at least a portion of clamp arm (610) is removable to permit removal of a clamp pad (646) from the distal end of clamp arm (610) rather than the proximal end. Clamp arm (610) comprises a body portion (612), a removable distal tip (620), and a distal attachment portion (630). Body portion (612) is configured to be pivotably coupled to instrument (100) and is generally the same as clamp arm (144) described above such that further details will not be described herein.

Figure 40:
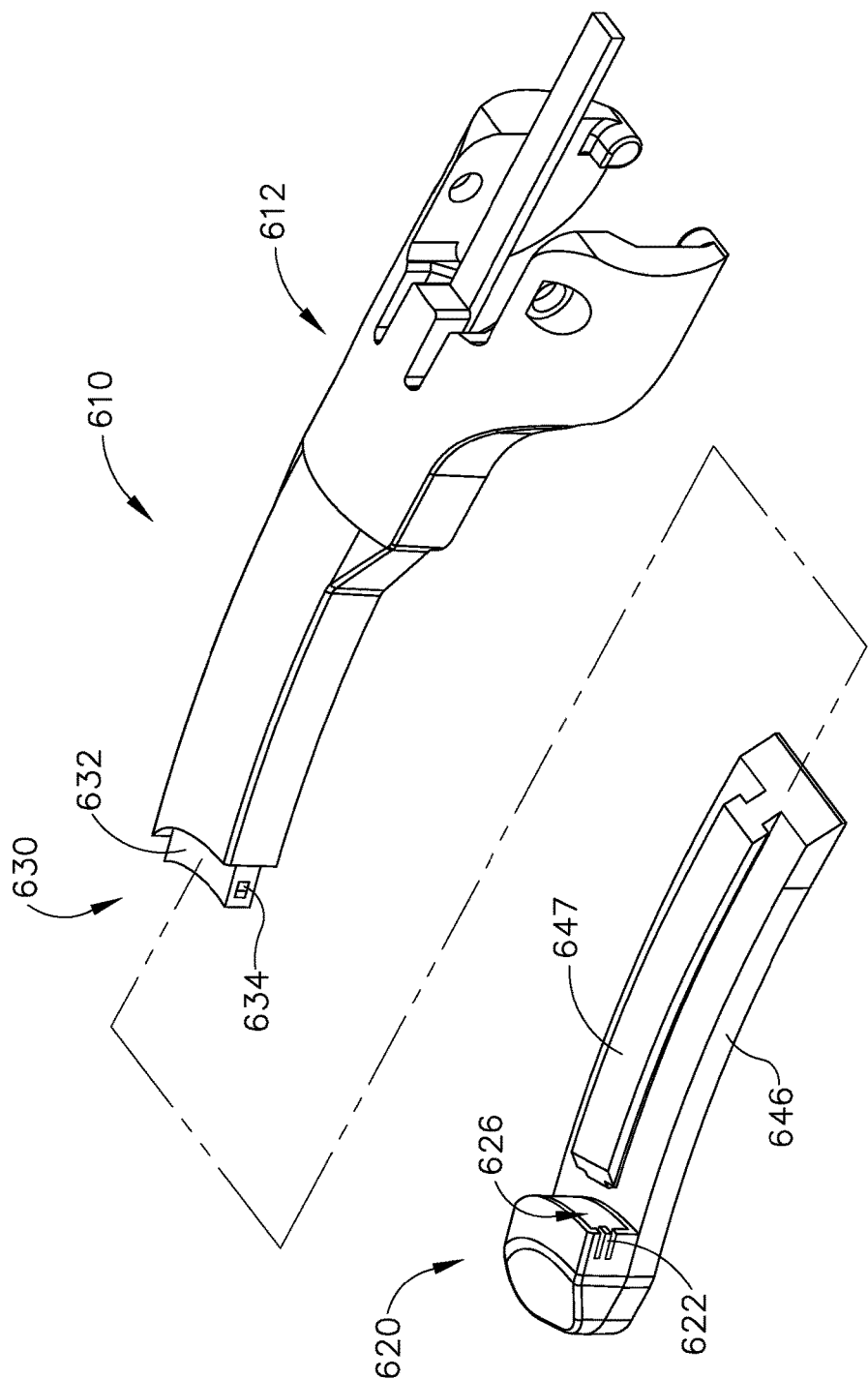
FIG. 40 depicts an exploded perspective view of the clamp arm of FIG. 39.

As can best be seen in FIG. 40, distal tip (620) comprises two resilient tabs (622, 624) and a single cavity (626). Each tab (622, 624) is integrated into the sidewall of distal tip (620) adjacent to cavity (626). Accordingly, each tab (622, 624) is configured to flex laterally outwardly relative to the sidewall of distal tip (620).

Figure 41:
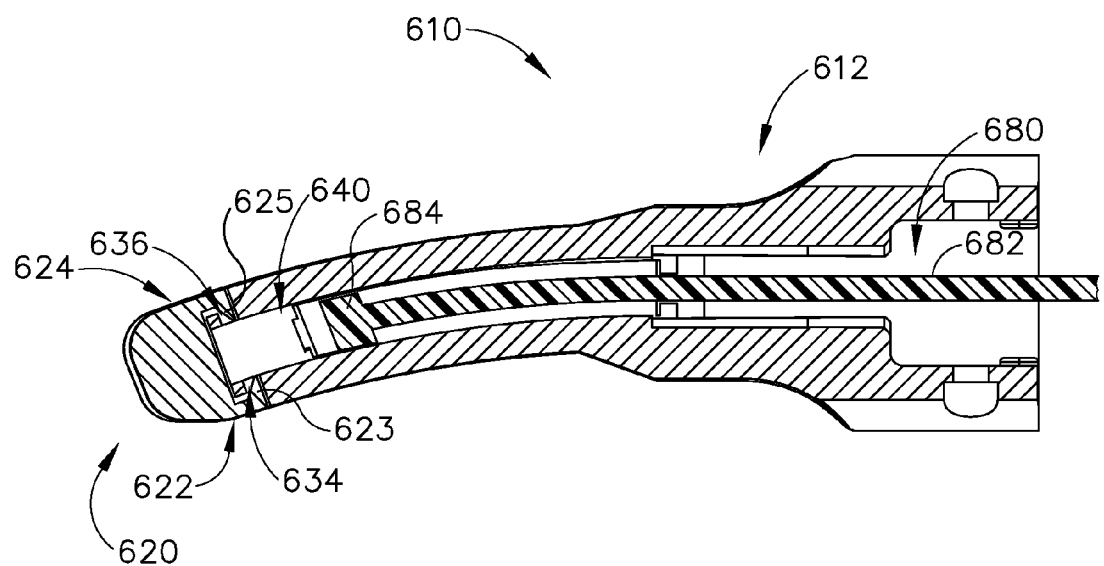
FIG. 41 depicts a top cross-sectional view of the clamp arm of FIG. 39, with the cross-section taken along line 41-41 of FIG. 39.

As can be seen in FIG. 41, each resilient tab (622, 624) defines a tooth (623, 625) at the proximal end of each resilient tab (622, 624). Although each tooth (623, 625) is shown as being generally triangular in shape, it should be understood that any suitable shape may be used. For instance, in some examples teeth (623, 625) incorporate rounded protrusions or detent features. As will be described in greater detail below, each tooth (623, 625) is generally configured to engage at least a portion of distal attachment portion (630) to selectively secure distal tip (620) to distal attachment portion (630). While the present example is shown as including two resilient tabs (622, 624), it should be understood that in other examples any suitable number of resilient tabs (622, 624) may be used.

Cavity (626) of distal tip (620) extends through at least a portion of distal tip (620), although not through all of distal tip (620). Cavity (626) is generally defined by a thin sidewall of distal tip (620) such that cavity (626) comprises a shape generally equivalent to the rectangular shape of the proximal face of distal tip. As will be described in greater detail below, cavity (626) is generally configured to receive at least portion of distal attachment portion (630) to permit engagement between tabs (622, 624) of distal tip (620) and at least a portion of distal attachment portion (630). Additionally, the engagement between cavity (626) and at least a portion of distal attachment portion (630) may provide lateral stability to distal tip (620) when secured to distal attachment portion (630).

Distal tip (620) is secured to a clamp pad (646) such that clamp pad (646) and distal tip (620) form a unitary part. In the present example, distal tip (620) comprises a metal alloy, while clamp pad (646) comprises a polymer such as polytetrafluoroethylene (PTFE). Accordingly, it should be understood that in the present example distal tip (620) and clamp pad (646) are joined by a suitable method for joining dissimilar materials such as adhesive bonding. Of course, in examples where distal tip (620) and clamp pad (646) comprise similar materials, the particular method of joining may be varied accordingly.

Clamp pad (646) is substantially the same as clamp pad (146) described above. However, unlike clamp pad (146), clamp pad (646) comprises a T-shaped key (647) that extends for only a portion of clamp pad (646). In particular, key (647) stops short of distal tip (620) to accommodate interaction of resilient tabs (622, 624) with distal attachment portion (630). Of course, in other examples clamp arm (610) may be configured such that key (647) extends distally to distal tip (620).

Like with key (147) described above, key (647) is configured to engage with a channel (640) of a corresponding shape such that channel (640) secures clamp pad (646) to clamp arm (610). As will be described in greater detail below, channel (640) is integrated into body (612), extending the length of body (612) through distal attachment portion (630). Thus, channel (640) is exposed at distal attachment portion (630) such that key (647) may be inserted into distal attachment portion (630) from the distal end of clamp arm (610).

Distal attachment portion (630) comprises an attachment member (632) extending distally from the distal end of body (612) of clamp arm (610). Attachment member (632) is generally the same shape as the elongate portion of body (612). However, attachment member (632) comprises a transverse cross-sectional size that is smaller relative to the longitudinal portion of body (612). This sizing permits attachment member (632) to be received in cavity (626) of distal tip (620), as will be described in greater detail below.

Each side of attachment member (632) defines a lock opening (634, 636). As will be described in greater detail below, lock openings (634, 636) are configured to receive teeth (623, 625) of distal tip (620) to selectively secure distal tip (620) to body (612) of clamp arm (610). It should be understood that lock openings (634, 636) extend transversely through attachment member (632) and into communication with channel (640). As will be described in greater detail below, this transverse extension into channel (640) permits selective release of teeth (623, 625) from lock openings (634, 636).

Figure 42:
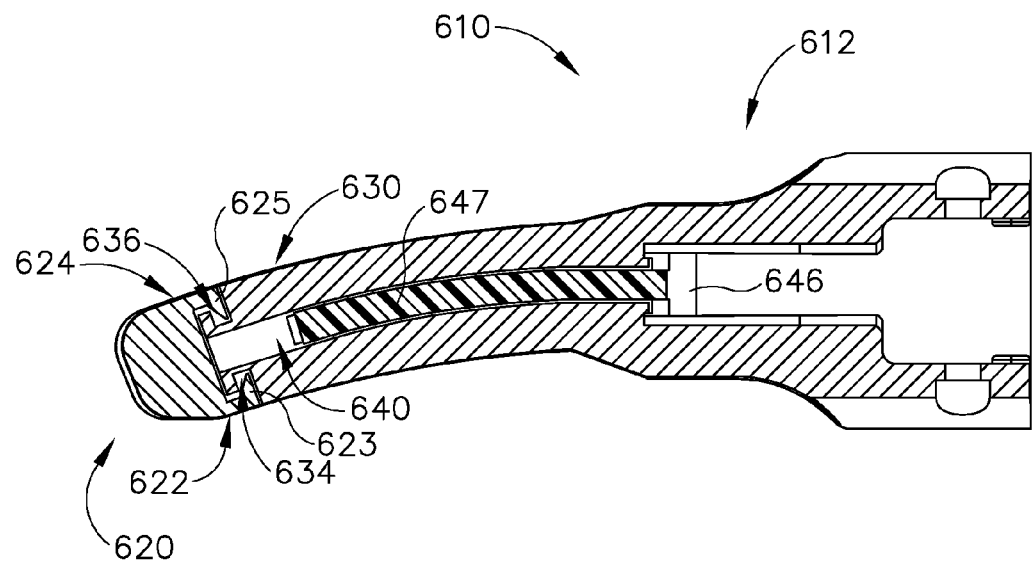
FIG. 42 depicts another top cross-sectional view of the clamp arm FIG. 39, with the cross-section taken along line 42-42 of FIG. 39.

As can be seen in FIGS. 41 and 42, channel (640) extends through distal attachment portion (630). Channel (640) also extends through attachment member (632) such that the distal end of attachment member (632) is open for reception of key (647) within channel (640). As is best seen in FIG. 41, channel (640) of the present example is additionally sized to receive an actuator (680). Actuator (680) comprises a flexible actuation portion (682) and an engagement portion (684). As will be described in greater detail below, actuator (680) is configured to translate through channel (640) to disengage teeth (623, 625) of distal tip (620) from lock openings (634, 636).

Figure 43:
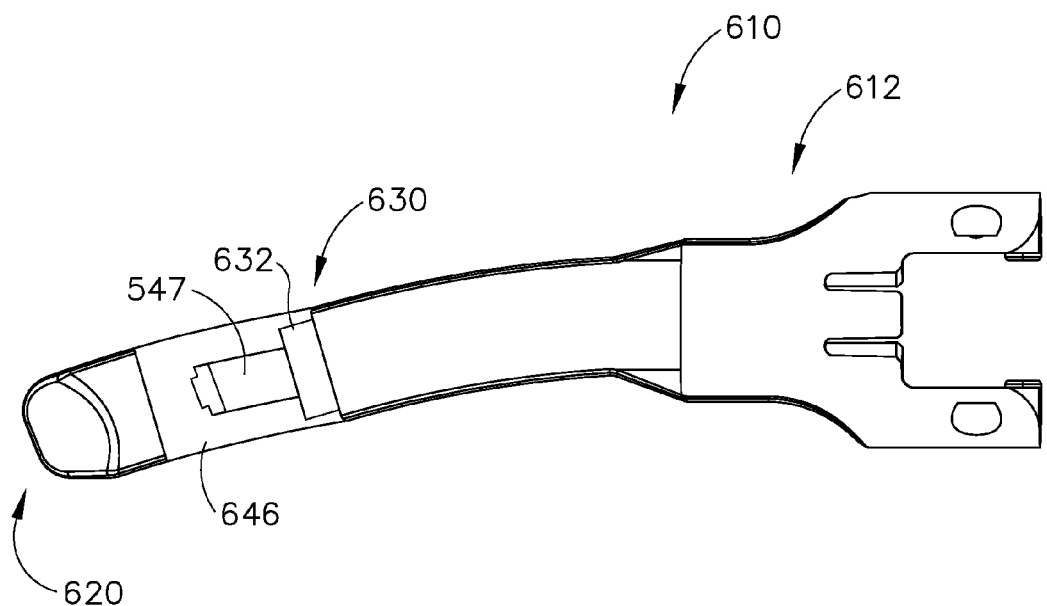
FIG. 43 depicts a top plan view of the clamp arm of FIG. 39, with a clamp pad partially inserted into the clamp arm.

FIGS. 43-46 show an exemplary use of clamp arm (610) to prepare clamp arm (610) for use in a surgical procedure. Initially, distal tip (620) and clamp pad (646) may be detached from body (612) of clamp arm (610). As can be seen in FIG. 43, key (647) of clamp pad (646) is initially inserted into channel (640). An operator may slide clamp pad (646) proximally relative to body (612) of clamp arm (610) until clamp pad (646) reaches the position in FIG. 44.

Figure 44:
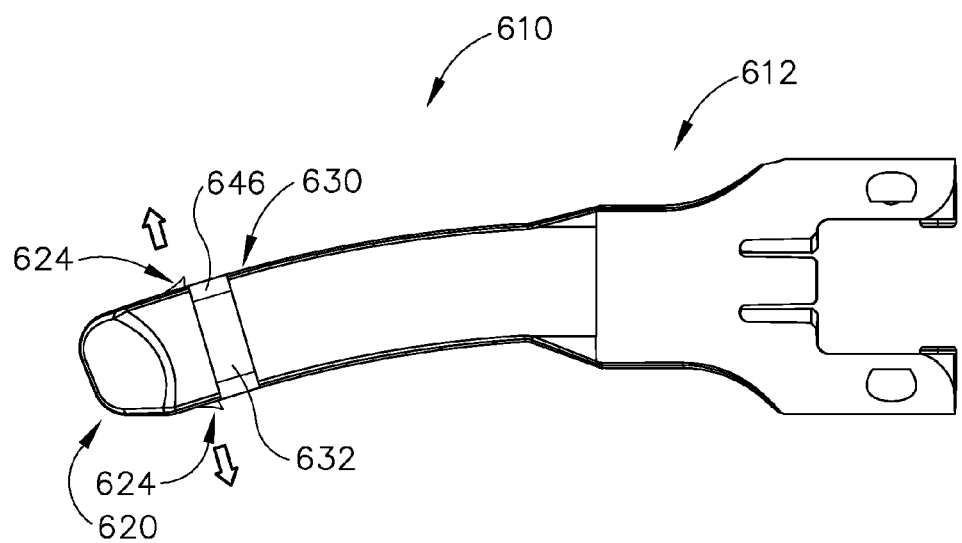
FIG. 44 depicts another top plan view of the clamp arm of FIG. 39, with a pair of resilient tabs engaging a distal attachment portion of the clamp arm.
Figure 45:
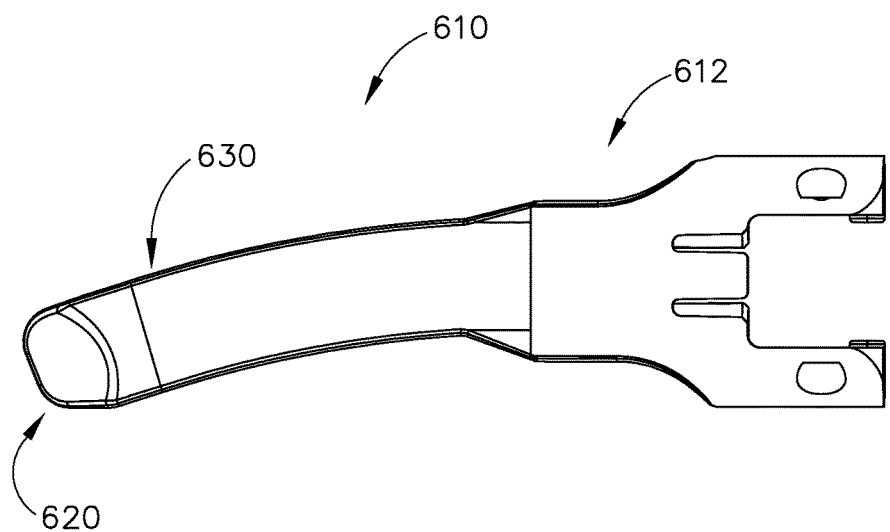
FIG. 45 depicts still another top plan view of the clamp arm of FIG. 39, with the clamp pad of FIG. 43 fully inserted into the clamp arm.

Once clamp pad (646) reaches the position shown in FIG. 44, distal tip (620) will begin to engage distal attachment portion (630). In particular, teeth (623, 625) of each resilient tab (622, 624) will begin to engage attachment member (632) of distal attachment portion (630). As clamp pad (646) is advanced further proximally, the triangular shape of each tooth (623, 625) will slide against the distal end of attachment member (632), pushing each resilient tab (622, 624) laterally outwardly relative to the sidewall of distal tip (620). Even further proximal advancement of clamp pad (646) will eventually lead to teeth (623, 625) snapping into position into lock openings (634, 636) of attachment member (632) as shown in FIG. 44. Such positioning of teeth (623, 625) corresponds to distal tip (620) and clamp pad (646) being positioned as shown in FIGS. 41 and 42.

Once teeth (623, 625) are in the position shown in FIG. 44, and distal tip (620) and clamp pad (646) are in the position shown in FIGS. 41 and 42, distal tip (620) is attached to distal attachment portion (630). Accordingly, clamp pad (646) is correspondingly locked in position and clamp arm (610) is in a state for the performance of a surgical procedure using instrument (100) as described above.

Optionally, an operator may desire to remove clamp pad (646) to replace clamp pad (646) with another different clamp pad or a clamp pad identical to clamp pad (646). To decouple distal tip (620) from distal attachment portion (630) and thereby release clamp pad (646), an operator may actuate actuator (680) distally. In some instances, instrument (100) may include actuation features such as buttons, levers, motors, cams, and/or etc. to actuate actuator (680). In other examples, actuator (680) may merely be manually operable by an operator.

Figure 46:
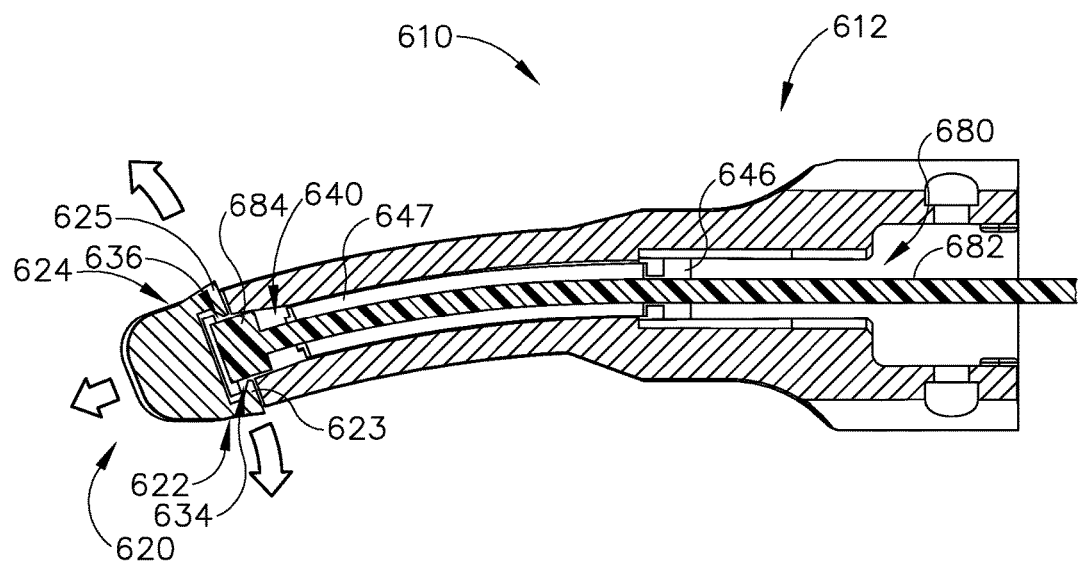
FIG. 46 depicts another top cross-sectional view of the clamp arm of FIG. 39, with the cross-section taken along line 41-41 of FIG. 39, and an actuator positioned distally relative to the clamp arm.
Figure 47:
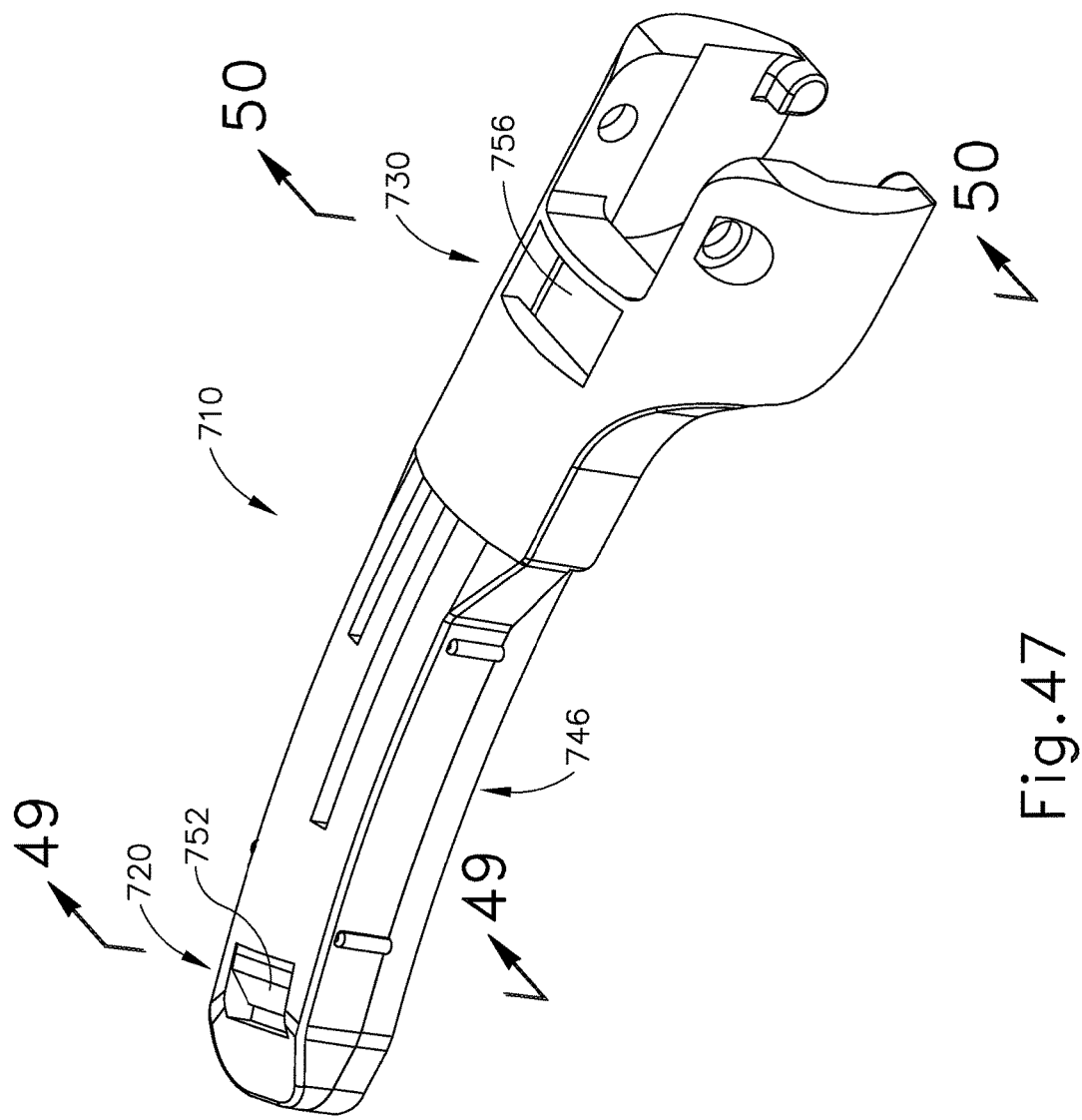
FIG. 47 depicts a perspective view of yet another clamp arm for use with the instrument of FIG. 2.

As can be seen in FIG. 46, distal actuation of actuator (680) will cause engagement portion (684) of actuator (680) to engage teeth (623, 625) of distal tip (620). Such engagement will force teeth (623, 625) outwardly against the resilient bias of resilient tabs (622, 624), thereby forcing teeth (623, 625) out of lock openings (634, 636). Once teeth (623, 625) are forced out of lock openings (634, 636), distal tip (620) may be pulled distally by an operator to thereby decouple clamp pad (646) from body (612) of clamp arm (610). The procedure described above may then be repeated by an operator to couple a new clamp pad (646) to clamp arm (610).

V. Exemplary Alternative Clamp Pads with Resilient Snap-on Features

In some instances, it may be desirable to provide clamp arms (144) and/or clamp pads (146) with features configured to allow an operator to selectively remove or otherwise decouple clamp pad (146) from clamp arm (114). One merely exemplary way in which to provide such selective operation to clamp arm (144) is to provide clamp arm (144) and/or clamp pad (146) with features operable to permit snap fit detachment of clamp pad (146) from clamp arm (114). Such features may be desirable because such features may permit an operator to more easily remove of clamp pad (146). The examples described below provide various examples of features and techniques configured to allow an operator to selectively remove or otherwise decouple a portion of a clamp arm similar to clamp arm (144). While various examples of features operable to provide such selective operation in clamp arm (144) will be described in greater detail below, other examples will be apparent to those of ordinary skill in the art according to the teachings herein. Similarly, various suitable ways in which the below teachings may be combined with the teachings of the various references cited herein will be apparent to those of ordinary skill in the art.

A. Exemplary Clamp Pad with Resilient Latch Features

FIGS. 47-50 show yet another exemplary alternative clamp arm (710) that may be readily incorporated into instrument (100) described above. Clamp arm (710) is substantially the same as clamp arm (144) described above unless otherwise noted herein. However, unlike clamp arm (144) described above, clamp arm (710) is configured to permit snap-fit coupling and decoupling of a clamp pad (746) clamp arm (710). Clamp arm (710) defines a distal snap receiver (720) and a proximal retainer (730). As will be described in greater detail below, distal snap receiver (720) and proximal retainer (730) are generally configured to work cooperatively to permit clamp pad (746) to selectively fasten to clamp arm (710).

Figure 48:
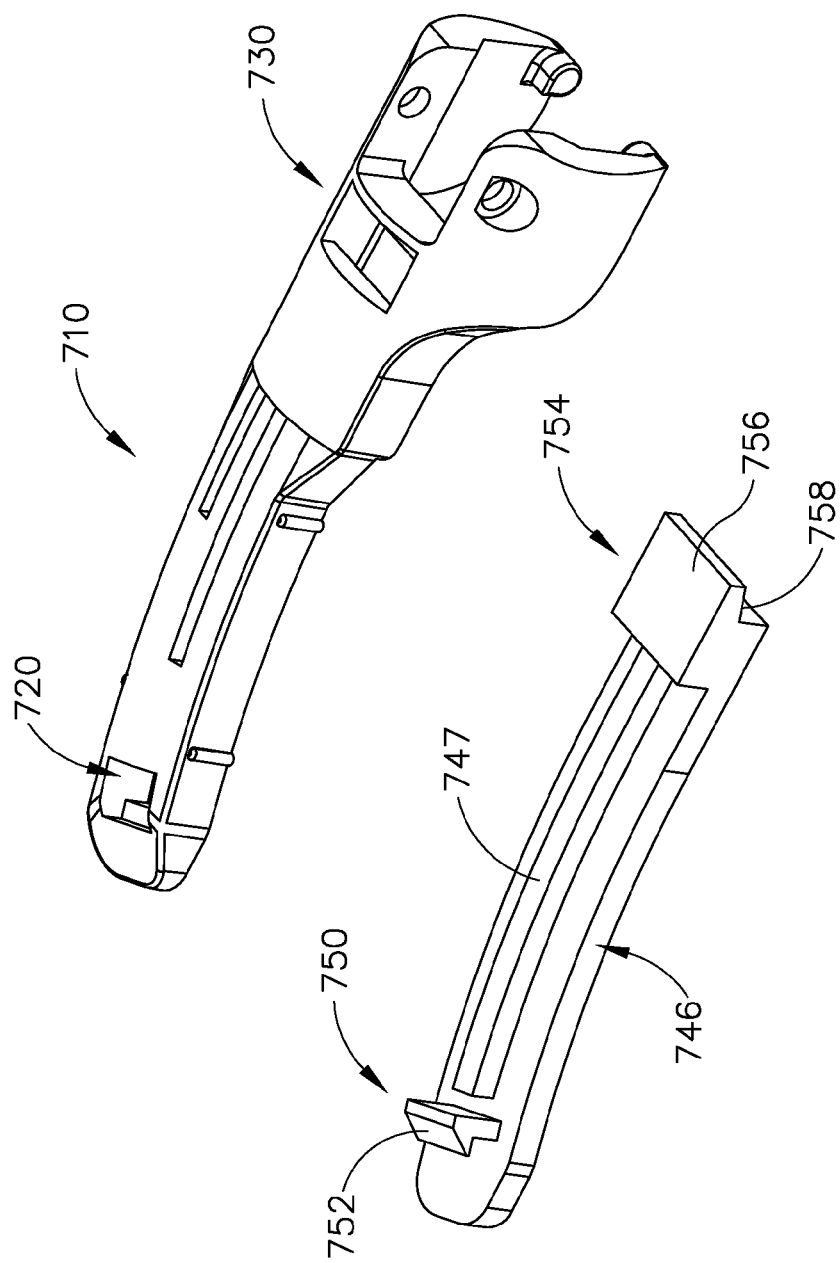
FIG. 48 depicts a perspective exploded view of the clamp arm of FIG. 47.

As is best seem in FIG. 48, clamp pad (746) comprises a rectangular key (747), a distal snap member (750) and a proximal retention member (754). Key (747) is similar to key (147) described above. However, unlike key (147), key (747) of the present example has a square cross-section rather than a faired cross-section. It should be understood that like key (147), key (747) is insertable into a corresponding channel (740) of clamp arm (710). However, because of the square cross-section, key (747) may be inserted into channel (740) laterally (e.g., up and down) and longitudinally. Thus, channel (740) of the present example does not function to maintain the up and down position of clamp pad (746). However, channel (740) will still maintain the side to side position of clamp pad (746).

Distal snap member (750) is positioned on the upper portion of clamp pad (746) distally of key (747). Distal snap member (750) extends upwardly from the upper face of clamp pad (746). On the upper most portion of distal snap member (750) distal snap member defines a lock tooth (752) extending distally from distal snap member (750). As will be described in greater detail below, lock tooth (752) is generally configured to engage in a snap fit action with distal snap receiver (720) of clamp arm (710) when clamp pad (746) is inserted onto clamp arm (710). Although lock tooth (752) comprises a generally triangular shape, it should be understood that in other examples numerous other shapes may be used. It should also be understood that because clamp pad (746) comprises a generally flexible material (e.g., PTFE) snap member (750) comprises generally resilient characteristics such that distal snap member (750) is resiliently biased toward the position shown in FIG. 48.

Proximal retention member (754) extends proximally from the proximal end of clamp pad (746). Proximal retention member (754) is offset from the upper face of clamp pad (746) such that proximal retention member (754) defines a retention feature (756) that is generally aligned with the upper face of clamp pad (746). Retention feature (756) includes an angled face (758) oriented on the underside of retention feature (756). As will be described in greater detail below, angled face (758) is generally configured to aid an operator in inserting retention feature (756) into proximal retainer (730) of clamp arm (710). Although angled face (758) is shown as being oriented at a given angle, no such limitation is intended. Indeed, in other examples angled face (758) is oriented at an angle more or less steep than the angle shown. Moreover, in other examples, the angle of angled face (758) is eliminated entirely and angled face (758) is merely parallel with the upper face of clamp pad (746).

Figure 49:
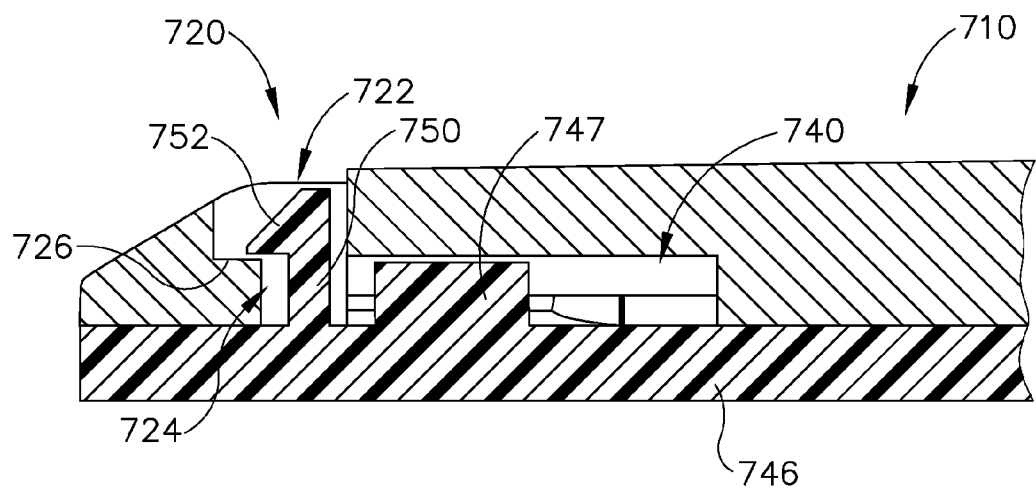
FIG. 49 depicts a partial side cross-sectional view of the clamp arm of FIG. 47, with the cross-section taken along line 49-49 of FIG. 47.

As is best seen in FIG. 49, distal snap receiver (720) of clamp arm (710) is generally configured to receive distal snap member (750) of clamp pad (746) when clamp pad (746) is fastened to clamp arm (710). In particular, distal snap receiver (720) defines a first opening (722) and a second opening (724). First opening (722) and second opening (724) are in communication with each other such that first opening (722) and second opening (724) together extend vertically through clamp arm (710). Both first and second openings (722, 724) generally have a rectangular cross-sectional shape. However, first opening (722) is generally wider than second opening (724). Because of the additional width of first opening (722), distal snap receiver (720) further defines a retention ledge (726). Retention ledge (726) comprises a generally flat surface. As will be described in greater detail below, the generally flat surface of retention ledge (726) is configured to receive lock tooth (752) of distal snap member (750) to selectively fasten clamp pad (746) to clamp arm (710).

Figure 50:
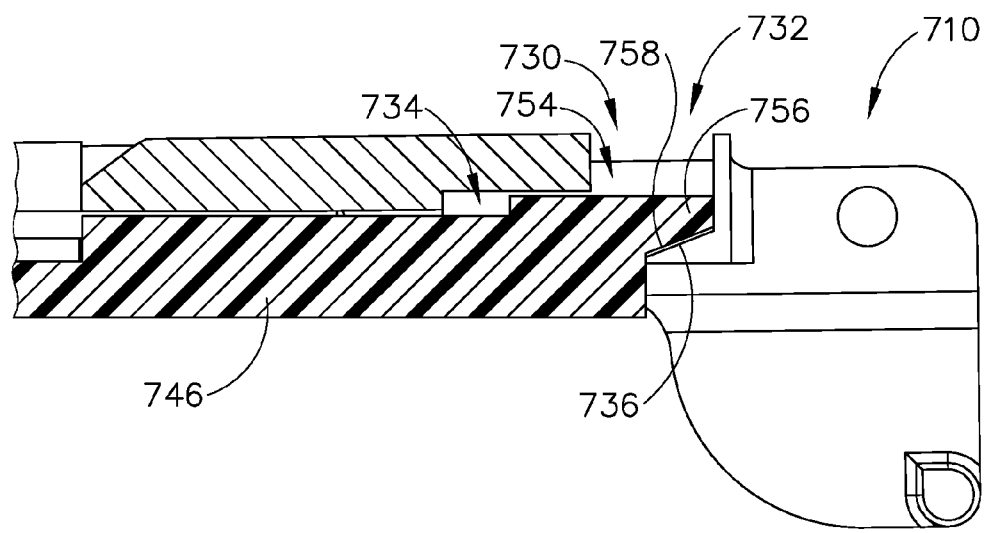
FIG. 50 depicts another partial side cross-sectional view of the clamp arm of FIG. 47, with the cross-section taken along line 50-50 of FIG. 47.

As is best seen in FIG. 50, proximal retainer (730) of clamp arm (710) is generally configured to receive proximal retention member (754) of clamp pad (746) when clamp pad (746) is fastened to clamp arm (710). In particular, proximal retainer (730) defines a first opening (732) and a second opening (734). Both first and second openings (732, 734) are in communication with each other such that openings (732, 734) together extend vertically through clamp arm (710). First opening (732) is offset relative to second opening (734) to accommodate proximal retention member (754) of clamp pad (746). Both first and second openings (732, 734) comprise a generally rectangular cross-sectional shape. However, second opening (734) comprises a larger width relative to first opening (732) to accommodate proximal retention member (754) entirely therein.

Proximal retainer (730) further defines a retention ledge (736) extending distally into second opening (734). Retention ledge (736) of the present example is oriented at an angle corresponding to the angle of angled face (758) of proximal retention member (754). Thus, retention ledge (736) is configured to engage angled face (758) of proximal retention member (754) thereon. As will be described in greater detail below, such engagement between angled face (758) and retention member (754) secures the proximal end of clamp pad (746) to clamp arm (746).

Figure 51:
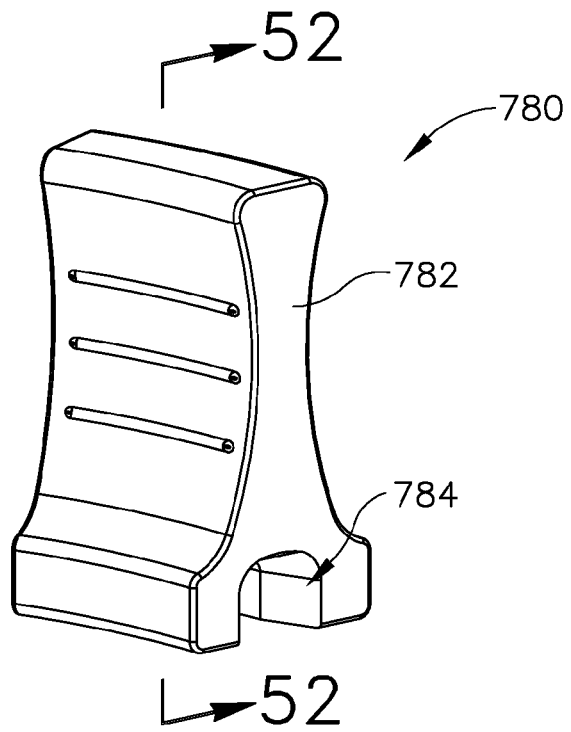
FIG. 51 depicts a perspective view of an exemplary tool for use with the clamp arm of FIG. 47.
Figure 52:
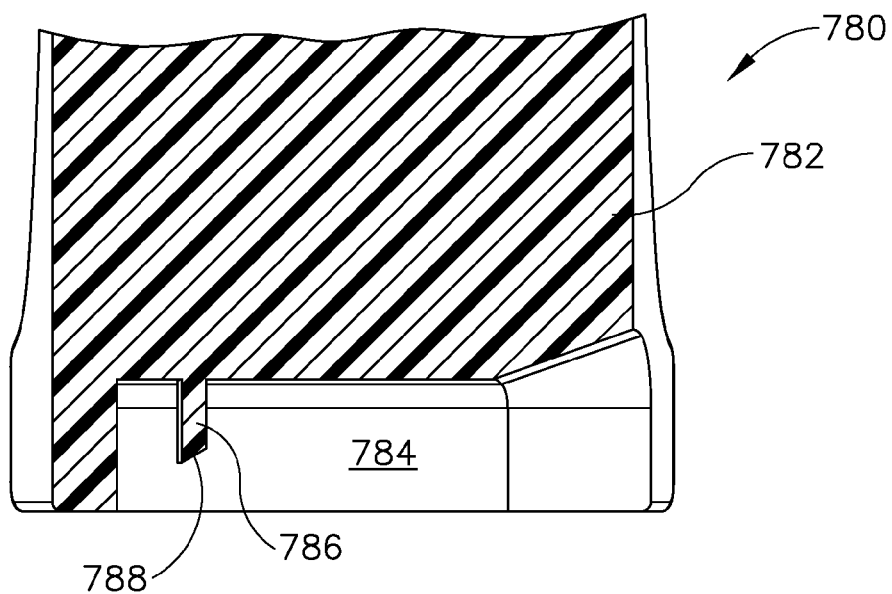
FIG. 52 depicts a side cross-sectional view of the tool of FIG. 51, with the cross-section taken along line 52-52 of FIG. 51.

FIGS. 51 and 52 show an exemplary detachment tool (780) that is usable with clamp arm (710) and clamp pad (746). Tool (780) comprises a handpiece (782) a clamp arm channel (784), and an engagement portion (786). Handpiece (782) is configured for gripping by an operator. Channel (784) corresponds to the shape of clamp arm (710) and is configured to receive clamp arm (710) therein. Engagement portion (786) extends downwardly into channel (784). As is best seen in FIG. 51, engagement portion (786) includes a ramped surface (788) that is configured to engage tooth (752) of clamp pad (746). As will be described in greater detail below, detachment tool (780) is generally configured to engage with clamp arm (710) to assist an operator with detachment of clamp pad (746) from clamp arm (710).

Figure 53:
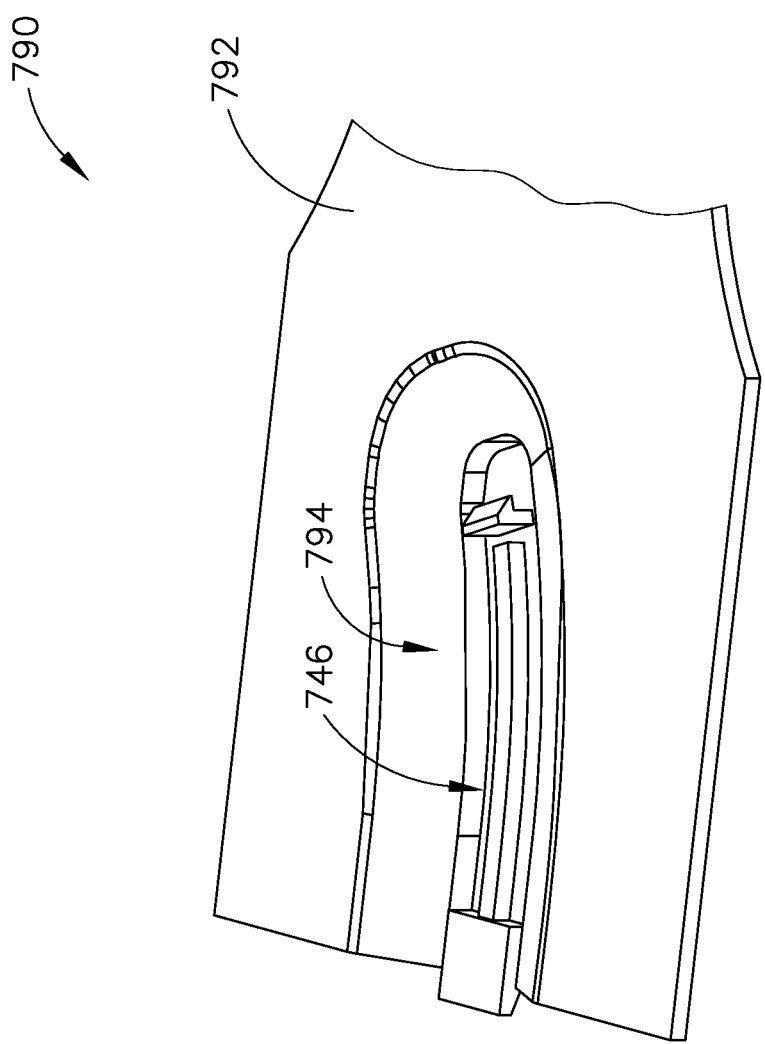
FIG. 53 depicts a perspective view of another exemplary tool for use with the clamp arm of FIG. 47.
Figure 54:
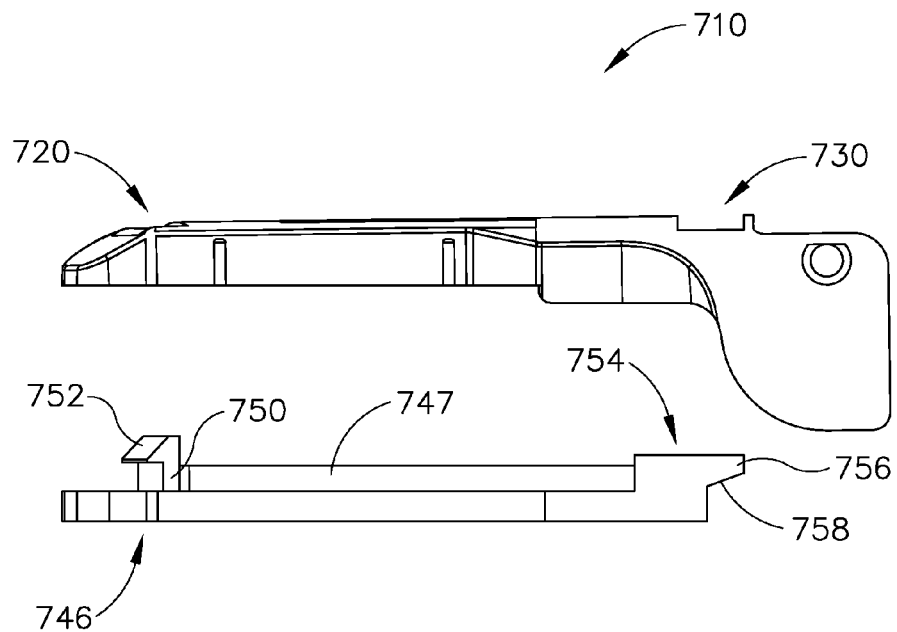
FIG. 54 depicts a side elevational view of the clamp arm of FIG. 47, with a clamp pad positioned adjacent to the clamp arm.

FIG. 53 shows an optional assembly tool (790). Assembly tool (790) is generally configured to receive clamp pad (746) to temporarily increase the size of clamp pad (746), thereby making clamp pad (746) more easily maneuverable. In particular, tool (790) includes a grip portion (792) and a pad receiving channel (794). Grip portion (792) extends outwardly from receiving channel (794), defining an area suitable for gripping by an operator.

Receiving channel (794) generally comprises a shape that corresponds to clamp pad (746). This permits clamp pad (746) to be received within receiving channel (794). While not shown, it should be understood that in other examples tool (790) may additionally include certain retention features to maintain clamp pad (746) within receiving channel (794) until clamp pad (746) is securely fastened to clamp arm (710).

Figure 55:
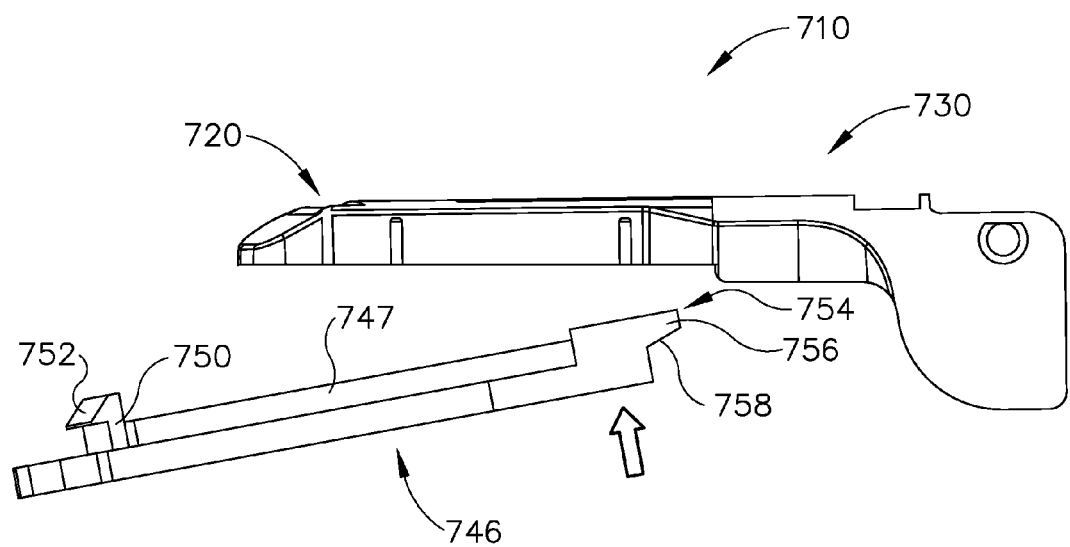
FIG. 55 depicts another side elevational view of the clamp arm of FIG. 47, with a proximal end the clamp pad of FIG. 54 oriented towards the clamp arm.

FIGS. 54-57 show an exemplary procedure for attaching clamp pad (746) to clamp arm (710). As can best be seen in FIG. 54, clamp pad (746) is initially manipulated by an operator to be adjacent to the underside of clamp arm (710). Once suitably positioned, an operator may manipulate clamp pad (746) (optionally with the use of tool (790) described above) to orient clamp pad (746) at an angle relative to clamp arm (710) as shown in FIG. 55.

Figure 56:
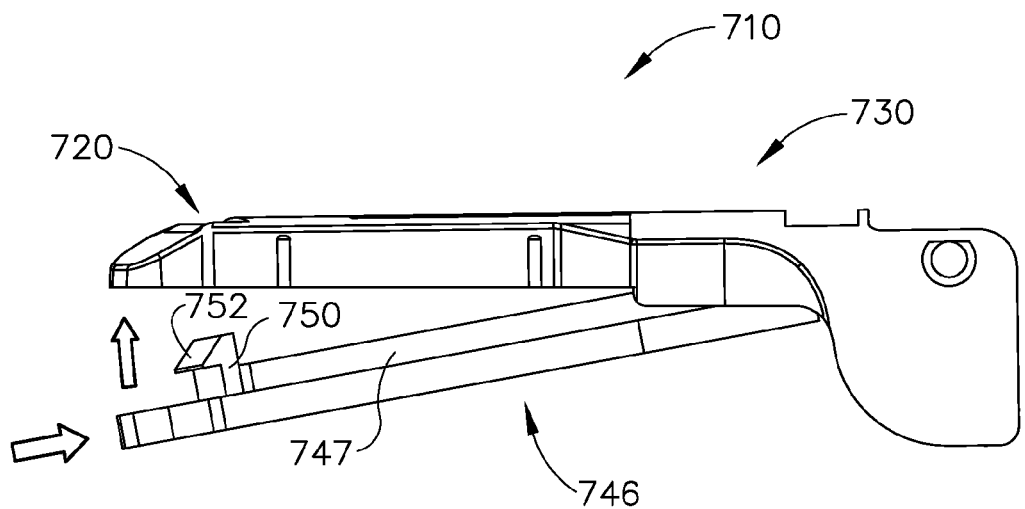
FIG. 56 depicts still another side elevational view of the clamp arm of FIG. 47, with the clamp pad of FIG. 54 partially inserted into the clamp arm.

Once oriented at an angle similar to that shown in FIG. 55, proximal retention member (754) of clamp pad (746) is inserted into second opening (734) of proximal retainer (730) as shown in FIG. 56. As proximal retention member (745) is inserted into second opening (734), angled face (758) of proximal retention member (745) will begin to engage retention ledge (736) of proximal retainer (730), thereby securing the proximal end of clamp pad (746) relative to clamp arm (710).

Figure 57:
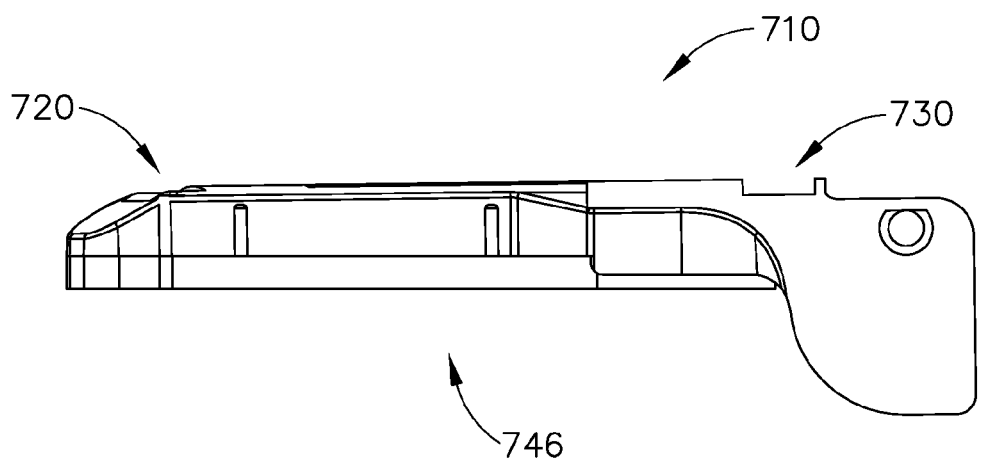
FIG. 57 depicts yet another side elevational view of the clamp arm of FIG. 47, with the clamp pad of FIG. 54 fully inserted into the clamp arm.

Once the proximal end of clamp pad (746) has been suitably secured relative to clamp arm (710), an operator may next push the distal end of clamp pad upwardly to the position shown in FIG. 57. As the distal end of clamp pad (746) moves upwardly, distal snap member (750) will enter second opening (724) of distal snap receiver (720). Engagement between tooth (752) of snap member (750) and the wall of second opening (724) will displace tooth (752) proximally permitting further upward movement of the distal end of clamp pad (746).

With further upward movement of the distal end of clamp pad (746), tooth (752) will enter first opening (722) of distal snap receiver (720). Once tooth (752) has fully entered first opening (722), tooth (752) will snap into engagement with retention ledge (726) of distal snap receiver (720) via the resilient bias of distal snap member (750). Once tooth (752) is fully engaged with retention ledge (726), clamp pad (746) is fastened to clamp arm (710) and a surgical procedure may be performed by an operator using instrument (100) as described above.

Figure 58:
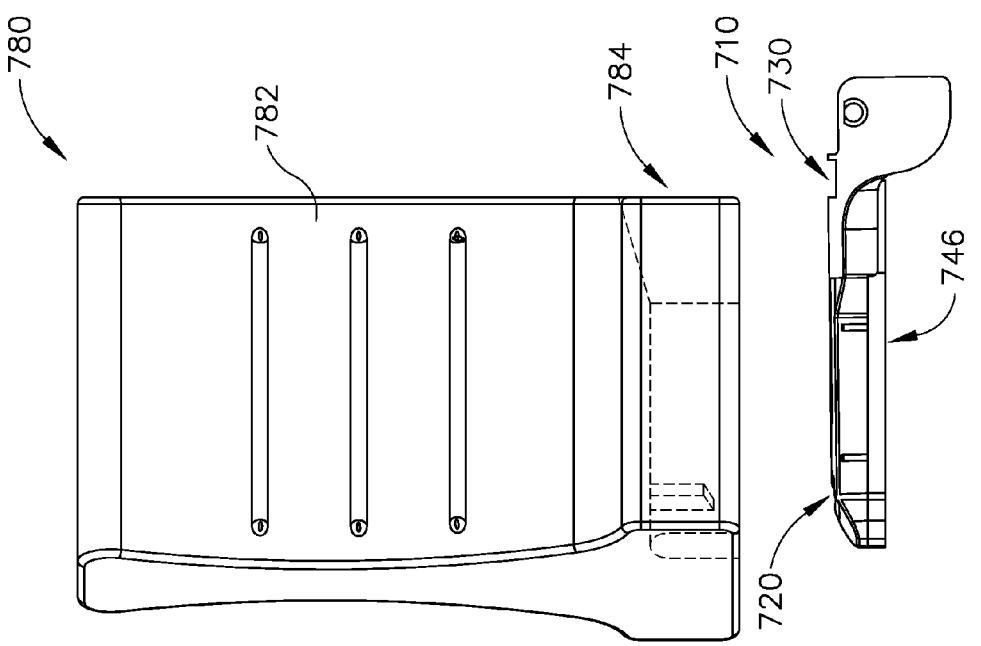
FIG. 58 depicts yet another side elevational view of the clamp arm of FIG. 47, with the tool of FIG. 51 positioned adjacent to the clamp arm.
Figure 60:
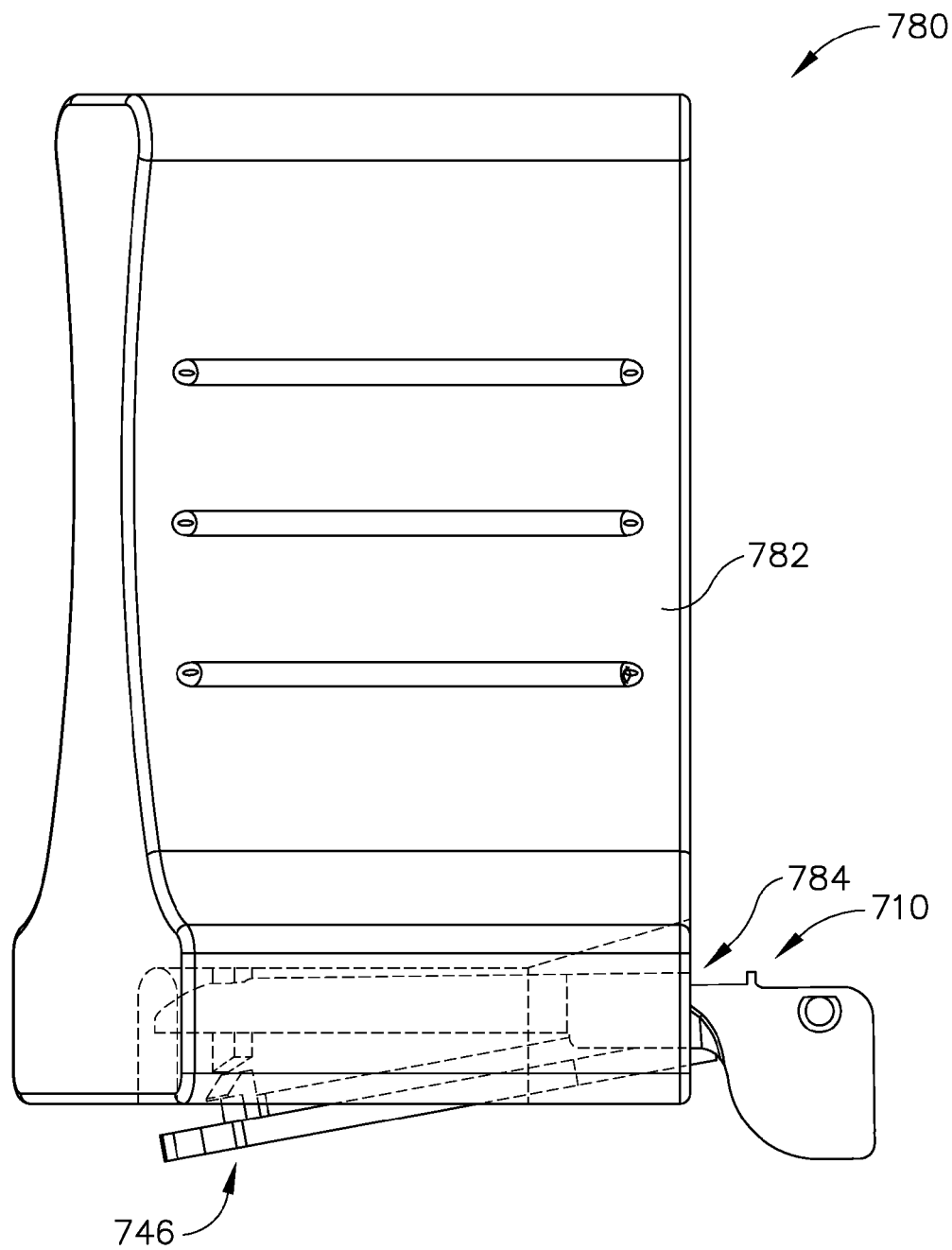
FIG. 60 depicts yet another side elevational view of the clamp arm of FIG. 47, with the tool of FIG. 51 fully engaged with the clamp arm.
Figure 61:
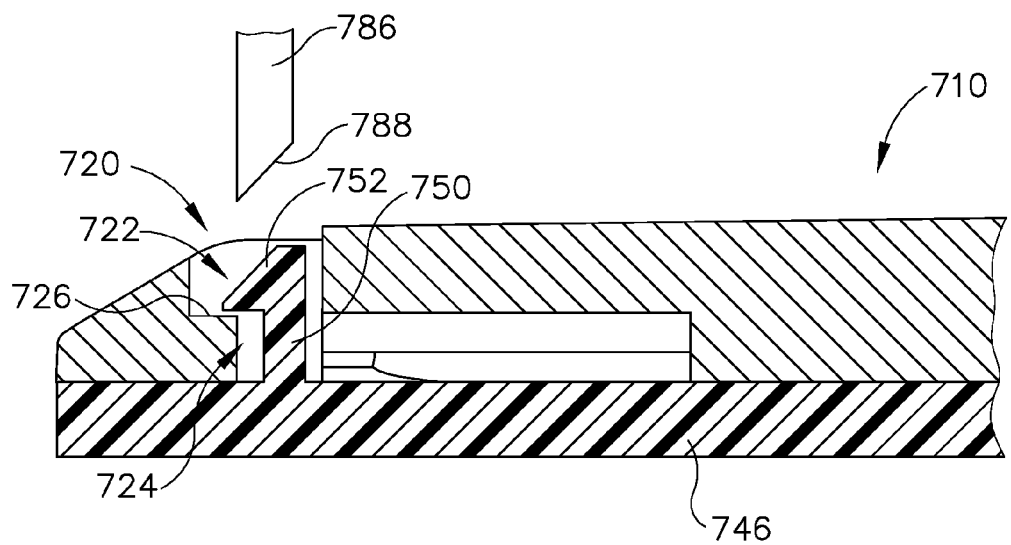
FIG. 61 depicts another partial side cross-sectional view of the clamp arm of FIG. 47, with a portion of the tool of FIG. 51 adjacent to the clamp arm.

Optionally, an operator may desire to decouple clamp pad (746) at some point during a surgical procedure or between surgical procedures. FIGS. 58-63 show an exemplary procedure for decoupling of clamp pad (746) from clamp arm (710). As can be seen in FIGS. 58 and 61, an operator may initially grasp detachment tool (780) and manipulate tool (780) adjacent to the upper side of clamp arm (710).

Figure 59:
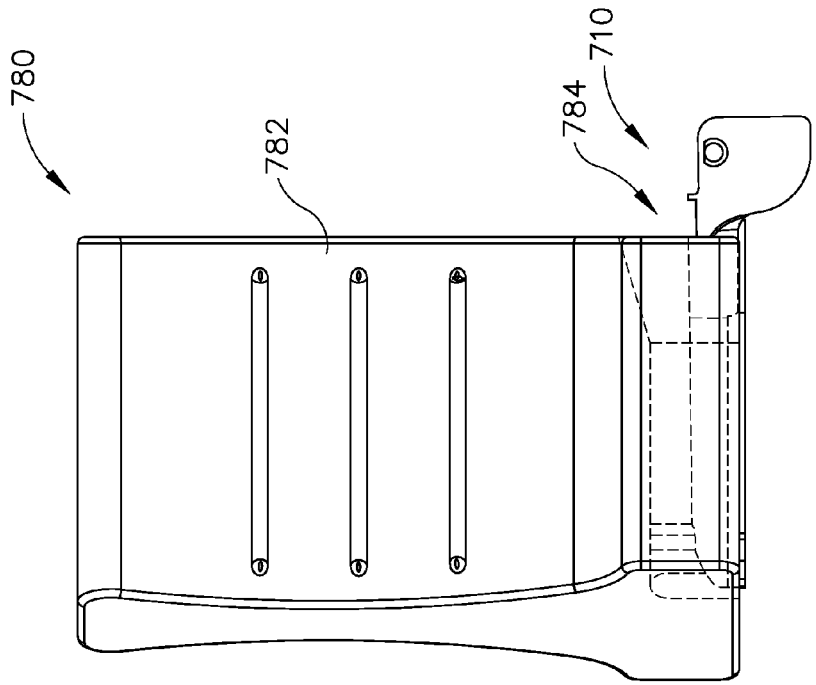
FIG. 59 depicts yet another side elevational view of the clamp arm of FIG. 47, with the tool of FIG. 51 partially engaged with the clamp arm.
Figure 62:
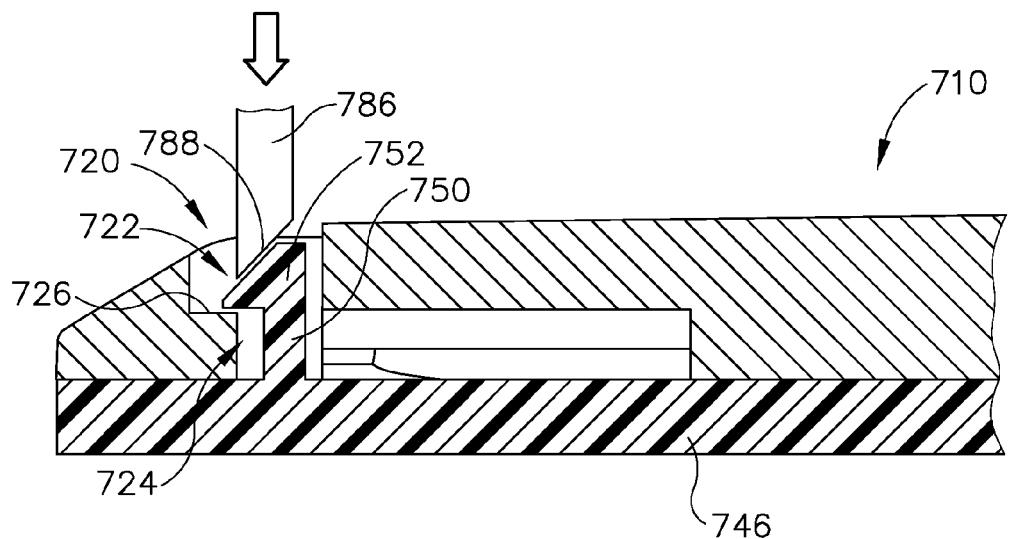
FIG. 62 depicts still another partial side cross-sectional view of the clamp arm of FIG. 47, with a portion of the tool of FIG. 51 partially engaging the clamp arm.

Once positioned as shown in FIGS. 58 and 61, an operator may begin decoupling clamp pad (746). To begin decoupling, an operator may move tool downwardly such that clamp arm (710) is partially received within channel (784), as shown in FIG. 59. With clamp arm (710) partially received within channel (784) engagement member (786) of tool (780) is positioned directly adjacent to snap member (750) of clamp pad (746), as shown in FIG. 62.

Figure 63:
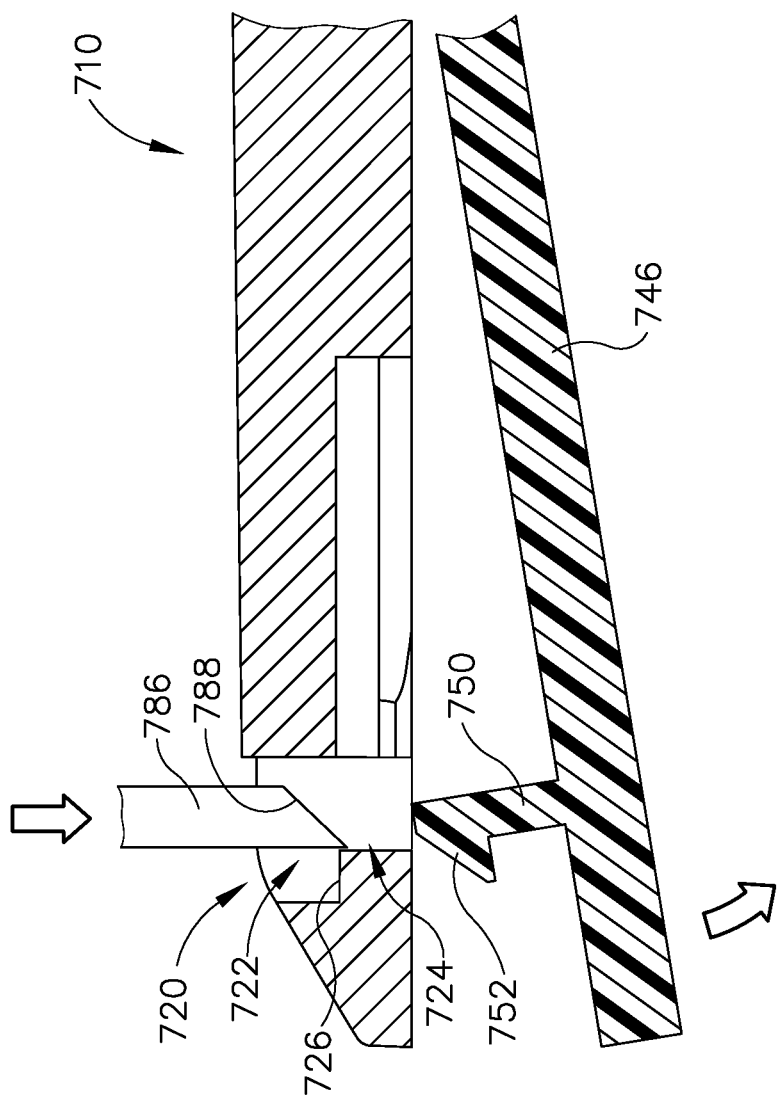
FIG. 63 depicts yet another partial side cross-sectional view of the clamp arm of FIG. 47, with a portion of the tool of FIG. 51 fully engaging the clamp arm.

Once engagement member (786) is positioned adjacent to snap member (750) an operator may push tool (780) downwardly toward the position shown in FIG. 59. As tool (780) is pushed downwardly, ramped surface (788) of engagement member (786) will begin to engage with tooth (752) of snap member (750). Engagement between ramped surface (788) and snap tooth (752) will overcome the resilient bias of snap member (750) as a user applies additional force to tool (780). Eventually, this force will cause snap member (750) to be displaced downwardly out of first and second openings (722, 724) of distal snap receiver (720) as shown in FIG. 63.

Once snap member (750) has been displaced from first and second openings (722, 724) of distal snap receiver (720), clamp pad (746) may be removed by an operator from clamp arm (710). An operator may then attach a new different clamp pad, or an identical clamp pad (746) using the attachment procedure described above.

B. Exemplary Clamp Pad with Resilient Side Tabs

Figure 64:
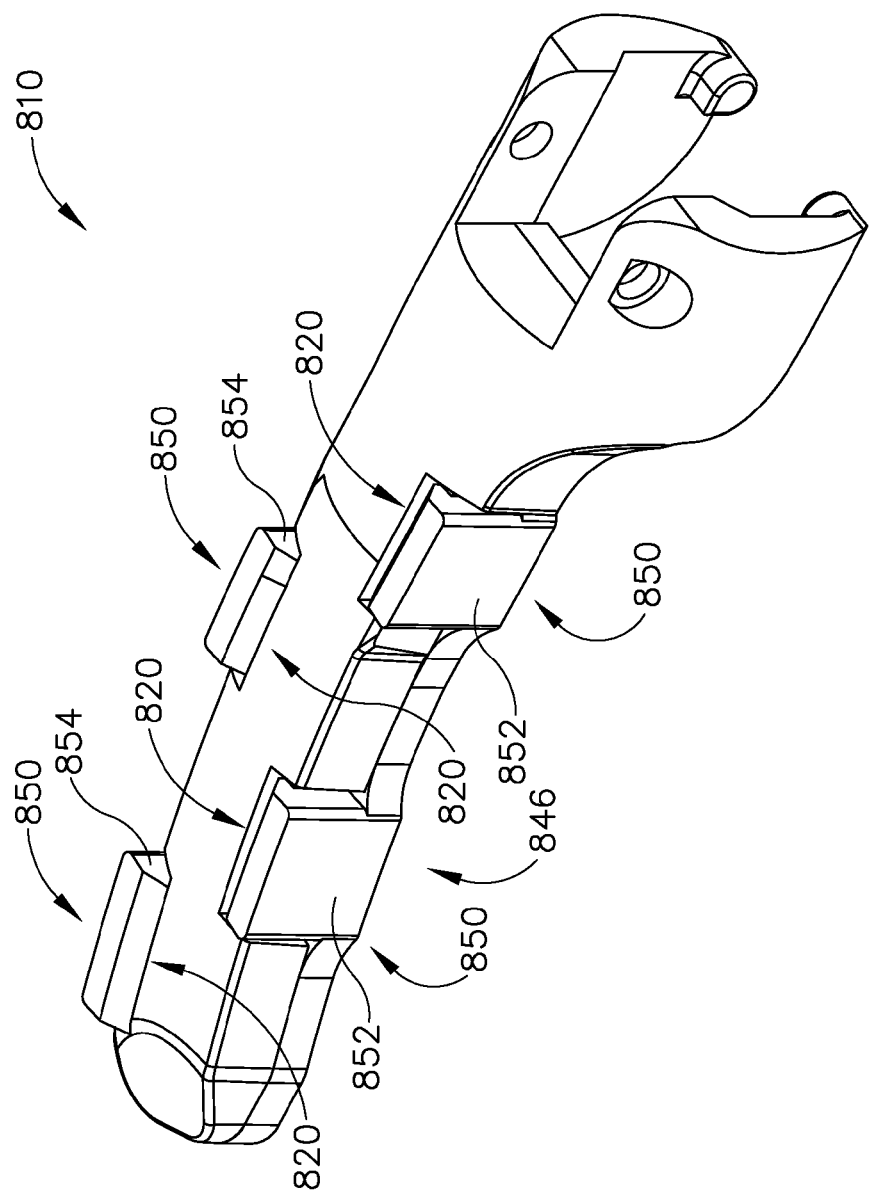
FIG. 64 depicts a perspective view of yet another clamp arm for use with the instrument of FIG. 2.
Figure 65:
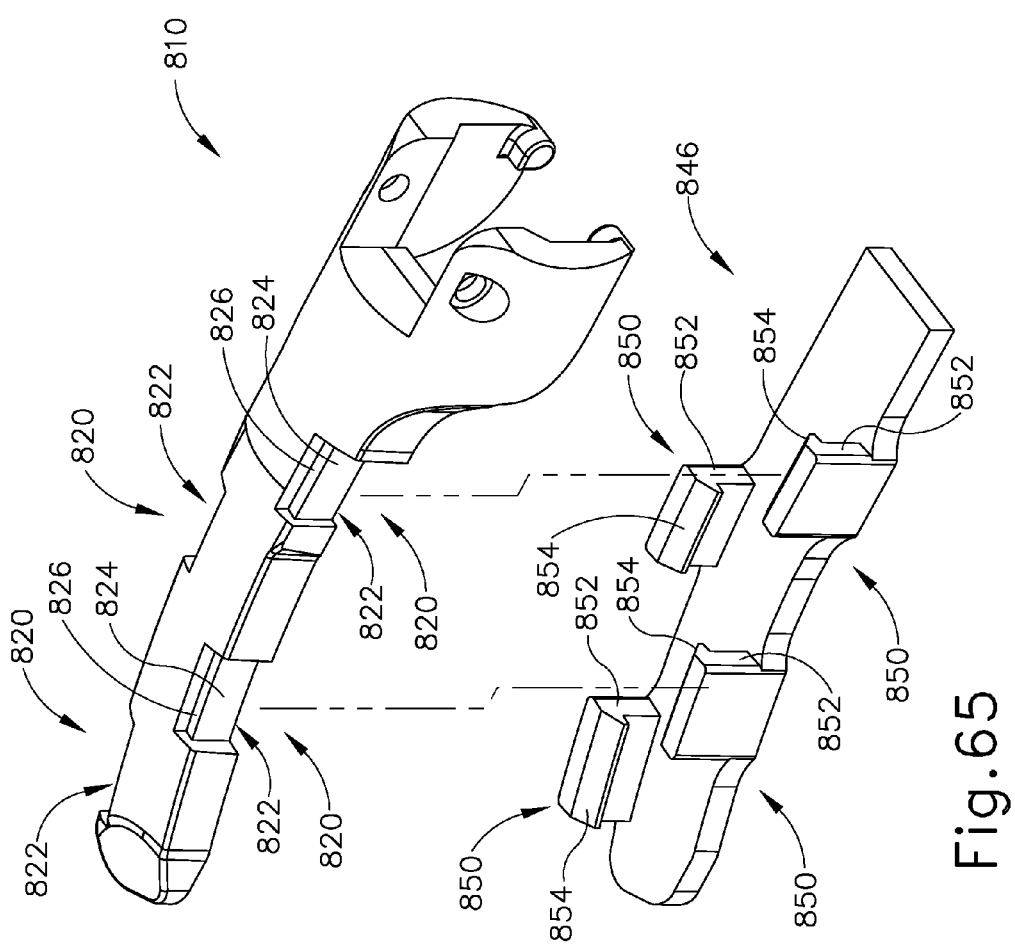
FIG. 65 depicts a perspective exploded view of the clamp arm of FIG. 64.

FIGS. 64 and 65 show yet another exemplary alternative clamp arm (810) that may be readily incorporated into instrument (100) described above. Clamp arm (810) is substantially the same as clamp arm (710) described above unless otherwise noted herein. For instance, like with clamp arm (710), clamp arm (810) is configured to permit snap-fit coupling and decoupling of a clamp pad (846) to clamp arm (810). However, unlike clamp arm (710) and clamp pad (746), clamp arm (810) and clamp pad (846) of the present example comprises multiple snap-fit mechanisms that couple clamp pad (846) to clamp arm (810).

FIG. 65 shows clamp pad (846) decoupled from clamp arm (810). As can be seen, clamp pad (846) comprises a plurality of generally identical snap members (850). Snap members (850) are disposed about the outer perimeter of clamp pad (846) along the sides of clamp pad (846). Each individual snap member (850) corresponds to another snap member (850) on the opposite side of clamp pad (846). However, it should be understood that each snap member (850) is not directly opposite of another snap member (850). Instead, each snap member (850) is staggered relative to its respective opposite snap member (850). In some examples this feature may be desirable to enhance the strength of the coupling between clamp pad (846) and clamp arm (810). However, it should be understood that this feature is merely optional and in some examples each snap member (850) is disposed in a position directly opposite of another snap member (850). Additionally, while the present example is shown as having four snap members (850), other examples may include any suitable number of snap members (850).

Each snap member (850) comprises an elongate resilient portion (852) and a generally triangular lock tooth (854). Resilient portion (852) extends upwardly from the upper face of clamp pad (846). Because clamp pad (846) is comprised of a generally flexible material such as PTFE, resilient portion (852) generally also has some flexibility but is resiliently biased toward the vertical positioning shown in FIG. 65. As will be described in greater detail below, the flexible yet resilient character of resilient portion (852) is configured to permit form a snap-fit when clamp pad (846) is inserted onto clamp arm (810).

Lock tooth (854) of each snap member (850) protrudes laterally inwardly from resilient portion (852). As will be described in greater detail below, lock tooth (854) is generally configured to engage at least a portion of clamp arm (810) to selectively secure clamp pad (846) to clamp arm (810). Although the shape of lock tooth (854) is generally triangular, it should be understood that numerous other shapes may be used. For instance, in some examples lock tooth (854) comprises a rounded protrusion to form a detent feature. Of course, other suitable shapes will be apparent to those of ordinary skill in the art in view of the teachings herein.

As is also seen in FIG. 65, clamp arm (810) includes a plurality of lock features (820). In the present example, each lock feature (820) corresponds to an associated snap member (850). Thus, each lock feature (820) is configured to receive a corresponding snap member (850) to thereby fasten clamp pad (846) to clamp arm (810). Each lock feature (820) is comprises an indentation (822) in the side of clamp arm (810). A lock shelf (824) is disposed inside of indentation (822). Lock shelf (824) generally comprises a rectangular member protruding into indentation (822). Lock shelf (824) defines an upwardly facing flat portion (826) that is configured to receive lock tooth (854) of snap member (850).

In an exemplary use, clamp pad (846) is attached to clamp arm (810) by an operator first aligning each snap member (850) of clamp pad (846) with each lock feature (820) of clamp arm (810). An operator then pushes clamp pad (846) upwardly such that each snap member (850) engages with each lock feature (820). This upward motion causes the triangular shape of each lock tooth (854) to engage with lock shelf (824). Each resilient portion (852) of each snap member (850) is initially pushed outwardly until each lock tooth (854) reaches each respective flat portion (826) of each respective lock shelf (824). Once reached, each lock tooth (854) is permitted to slide along each respective flat portion (826), thereby returning each resilient portion (852) to the position shown in FIG. 65. Clamp pad (846) is then selectively fastened to clamp arm (810) as shown in FIG. 64.

It should be understood that although not shown, clamp pad (846) may be used in conjunction with an attachment tool similar to attachment tool (790) described above. In some examples it may be desirable to use such an attachment tool to enhance the ease by which an operator may grip clamp pad (846). Of course, such an attachment tool is merely optional and is omitted in some examples.

To remove clamp pad (846) an operator may simply manually push each snap member (850) of clamp pad (846) out of engagement with each lock feature (820) of clamp arm (810) while simultaneously pushing clamp pad (846) downwardly. However, in some examples, manual removal of clamp pad (846) may be less desirable because manipulating each snap member (850) out of engagement with each lock feature (820) may be challenging or cumbersome with some operators. For instance, because the present example includes four snap members (850), all four snap members (850) may be disengaged before clamp pad (846) is removed. This may require simultaneous manipulation of all four snap members (850) or otherwise some previously disengaged snap members (850) may re-engage during disengagement of other snap members (850). Accordingly, in some instances it may be desirable to use a tool or other apparatus in conjunction with clamp arm (810) to more readily remove clamp pad (846).

Figure 66:
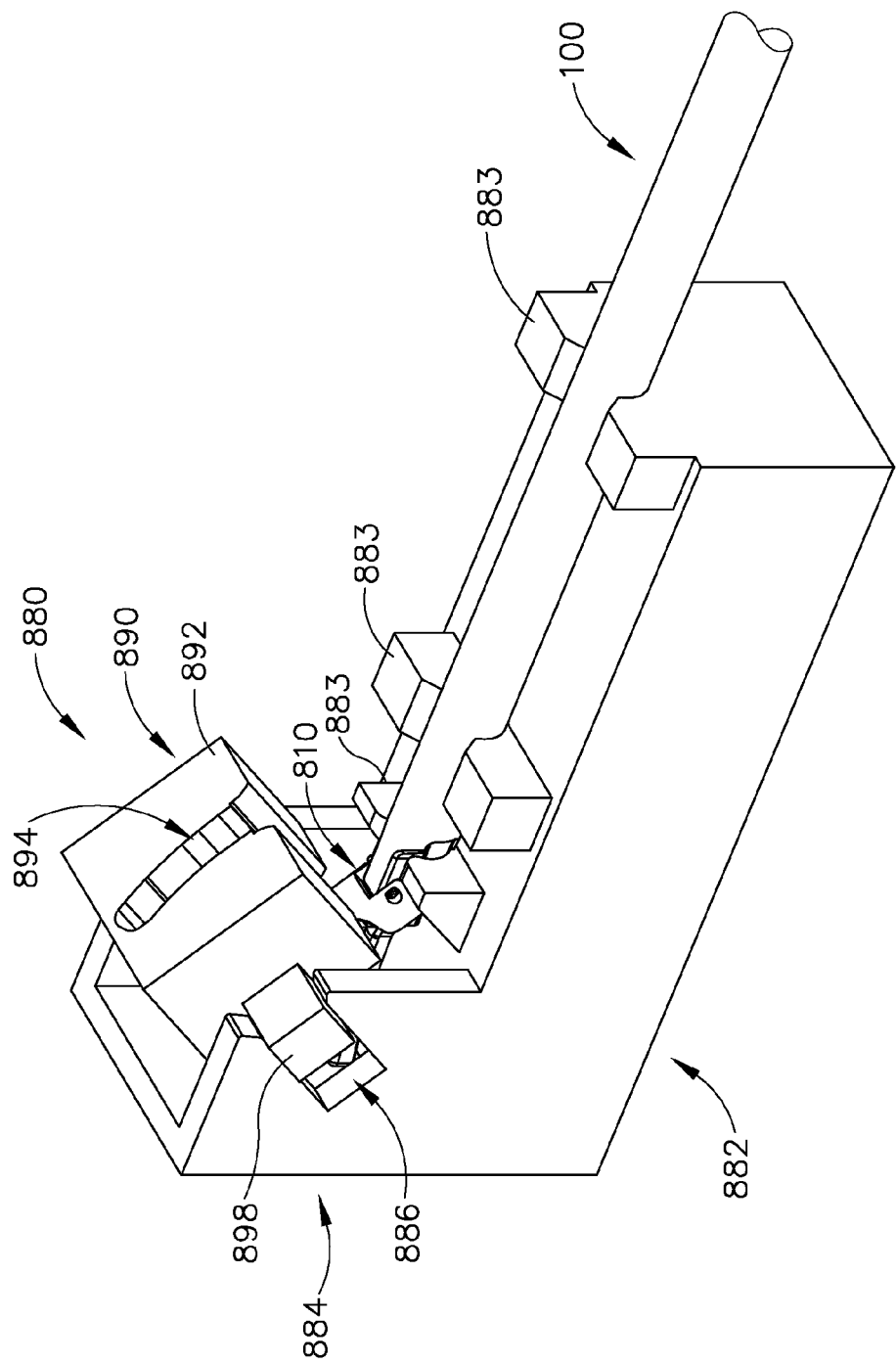
FIG. 66 depicts a perspective view of a removal tool for use with the clamp arm of FIG. 64.
Figure 67:
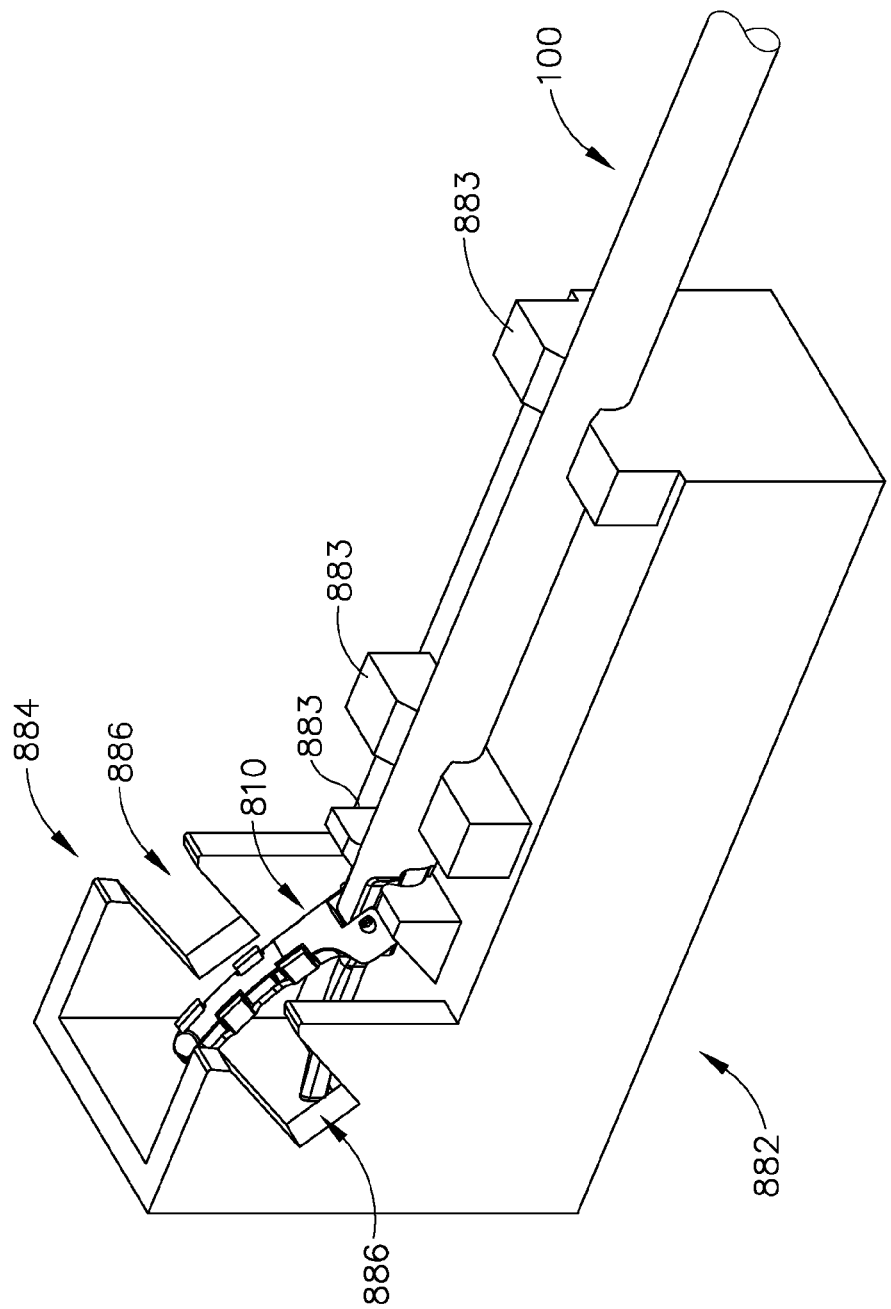
FIG. 67 depicts a perspective view of a bracket of the removal tool of FIG. 66.
Figure 68:
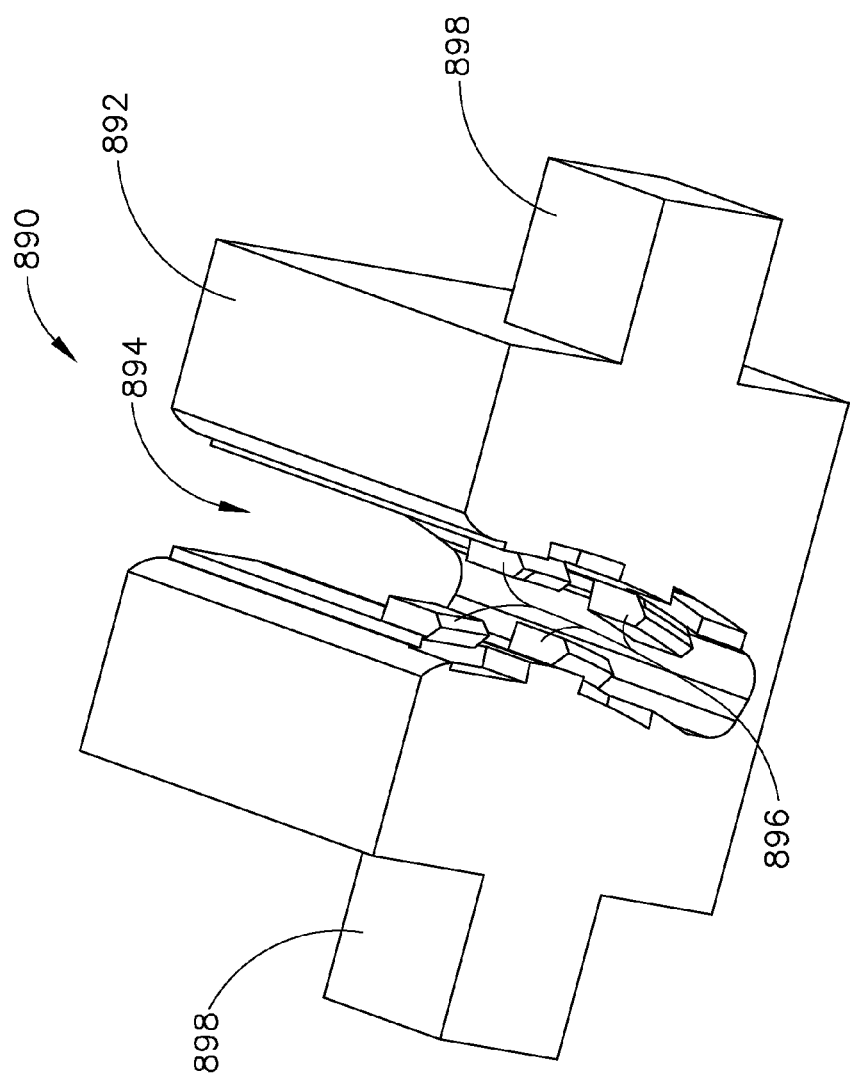
FIG. 68 depicts a perspective view of a block for use with the removal tool of FIG. 66.

FIGS. 66-68 show an exemplary removal tool (880) for use with clamp arm (810) to remove clamp pad (846) by simultaneously disengaging all snap members (850) of clamp pad (846) from lock features (820) of clamp arm (810). As can be seen in FIG. 66, tool (880) comprises a bracket (882) and a decoupling block (890). Bracket (882) is shown in FIG. 67 with decoupling block (890) removed. As can be seen, bracket (822) comprises a plurality of cradling features (883) and a block bracket (884). Cradling features (883) are configured to support clamp arm (810) and the rest of instrument (100) in a desirable position relative to block bracket (884). While a specific configuration of cradling features (883) is shown, it should be understood that in other examples cradling features ((883) may take on numerous alternative configurations as will be apparent to those of ordinary skill in the art in view of the teachings herein.

Block bracket (884) comprises two slots (886) disposed on either side of clamp arm (810). Each slot (886) is generally rectangular and is oriented at an angle that is perpendicular to the angle of clamp arm (810) when instrument (100) has actuated clamp arm (810) into an open position. Alternatively, in some examples, removal tool (880) may be configured for use while clamp arm (810) has been actuated to a closed position. In such examples, it should be understood that the particular angle of each slot (886) may be altered correspondingly. As will be described in greater detail below, each slot (886) is configured to receive at least a portion of decoupling block (890) to permit coupling block (890) to translate at an angle perpendicular to clamp arm (810). Decoupling block (890) is shown in FIG. 68. Decoupling block (890) comprises a body (892), and two sliders (898). Body (892) defines a clamp arm channel (894). Channel (894) is shaped to receive clamp arm (810) therein. The interior of channel (894) includes a plurality of wedges (896). Each wedge (896) corresponds to a particular snap member (850) of clamp pad (846). As will be described in greater detail below, each wedge (896) is configured to engage with a corresponding snap member (850) to simultaneously drive each snap member (850) outwardly and downwardly (e.g., perpendicularly relative to the longitudinal axis of clamp arm (810)).

Each slider (898) is disposed on either side of body (892). Each slider (898) extends outwardly from body (892), defining a generally square or rectangular cross-section. As will be understood, each slider (898) is configured to engage with a corresponding clot (886) of block bracket (884) such that decoupling block (890) may slide between a predetermined range of motion.

Figure 69:
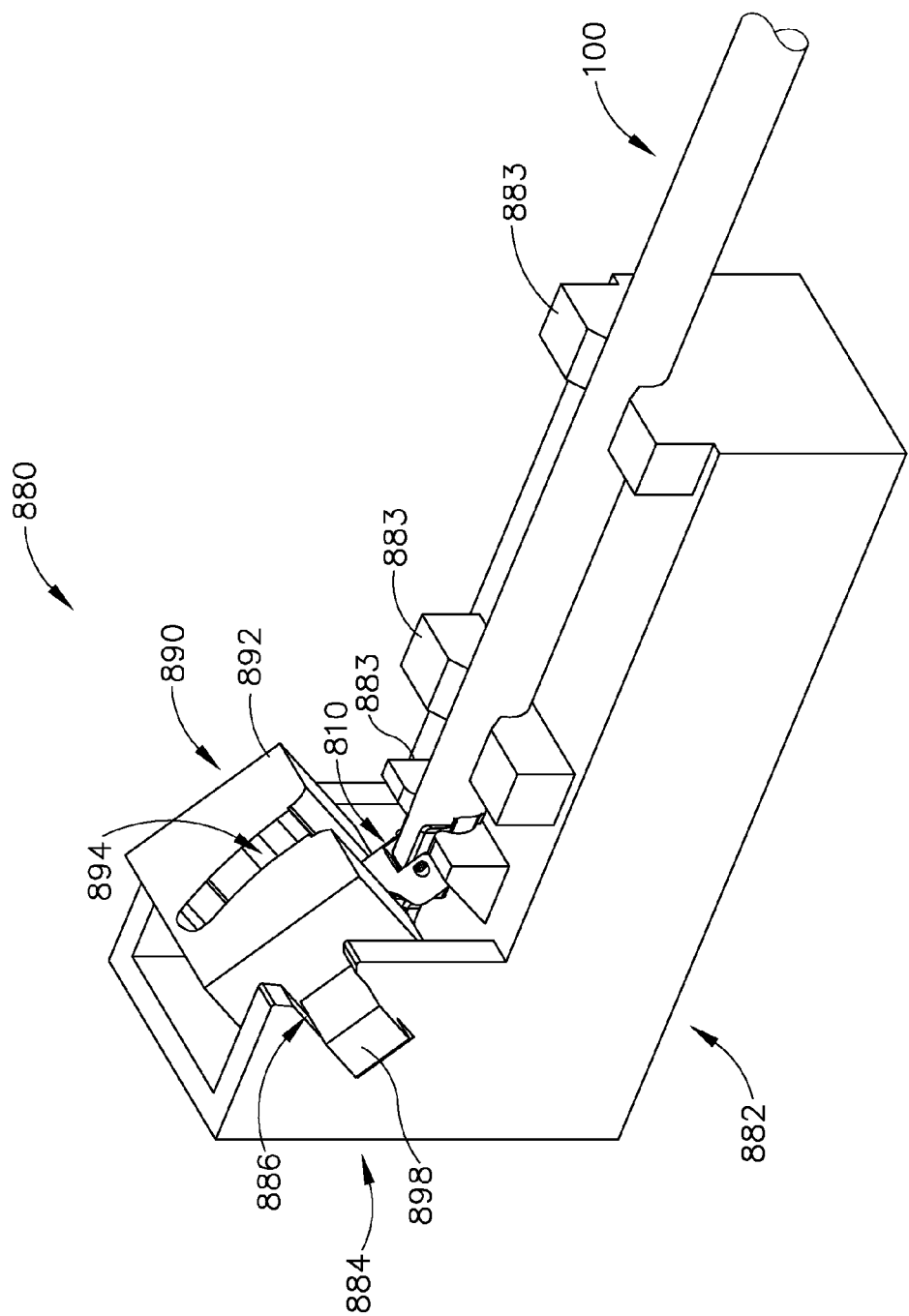
FIG. 69 depicts another perspective view of the removal tool of FIG. 66, with the block of FIG. 66 advanced.

An exemplary use of tool (880) can be seen by comparing FIGS. 66 and 69. For instance, instrument (100) and clamp arm (810) may be initially inserted into bracket (882) with clamp arm (810) in the open position. Next, decoupling block (890) is inserted onto bracket (882) with sliders (898) inserted into slots (886) of block bracket (884). This configuration is shown in FIG. 66.

Once tool (880) is assembled with instrument (100) and clamp arm (810) placed therein, an operator may remove clamp pad (846) from clamp arm (810) by simply pushing decoupling block (890) in the direction of slots (886) to the position shown in FIG. 69. This motion causes wedges (896) of decoupling block (890) to engage with each snap member (850) of clamp pad (846). As decoupling block (890) is translated, wedges (896) simultaneously act on each corresponding snap member (850) pushing each snap member (850) outwardly and perpendicularly away from clamp arm (810). Continued translation will then completely separate clamp pad (846) from clamp arm (810). Once clamp pad (846) is removed, an operator may optionally replace clamp pad (846) with a new different clamp pad or new identical clamp pad (846) using the same assembly procedure described above.

C. Exemplary Clamp Pad with Resilient Cap Features

Figure 70:
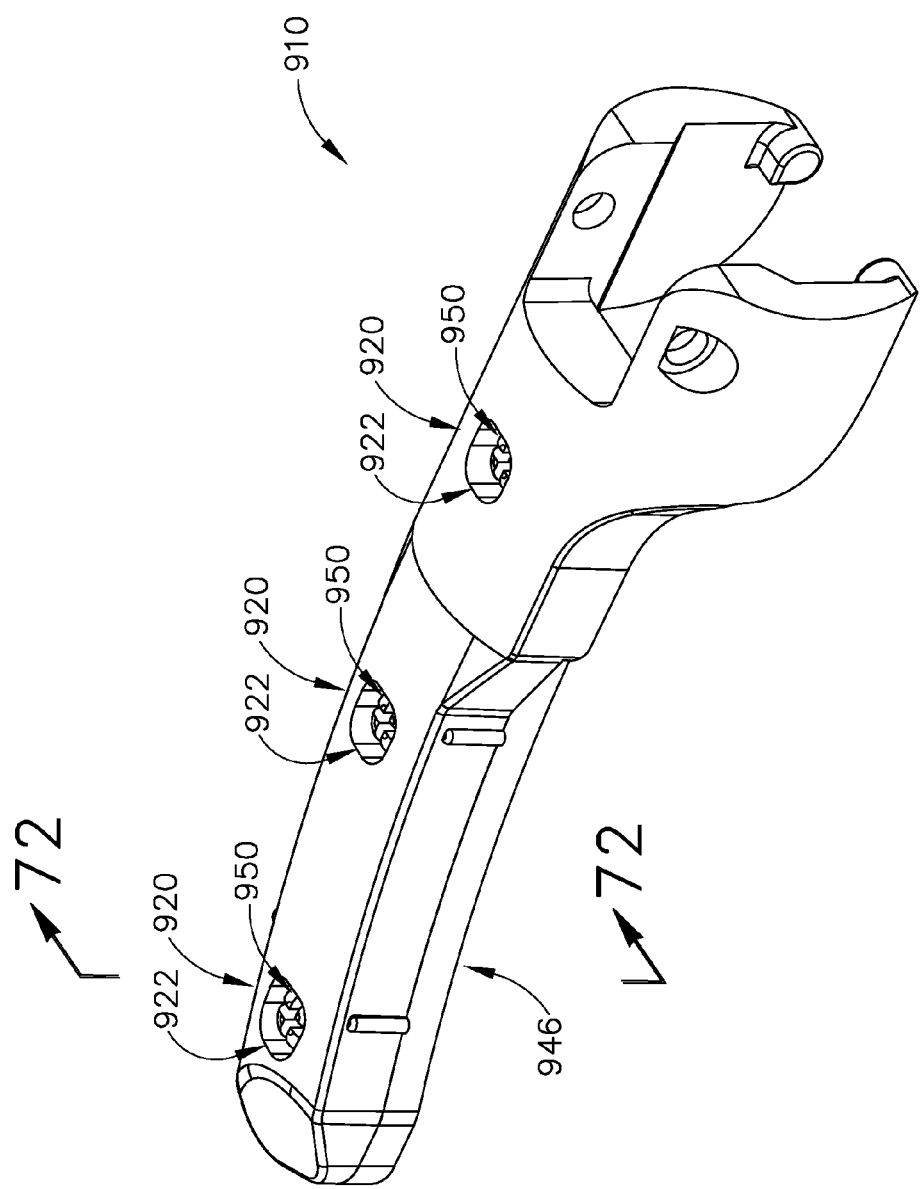
FIG. 70 depicts a perspective view of yet another clamp arm for use with the instrument of FIG. 2.
Figure 71:
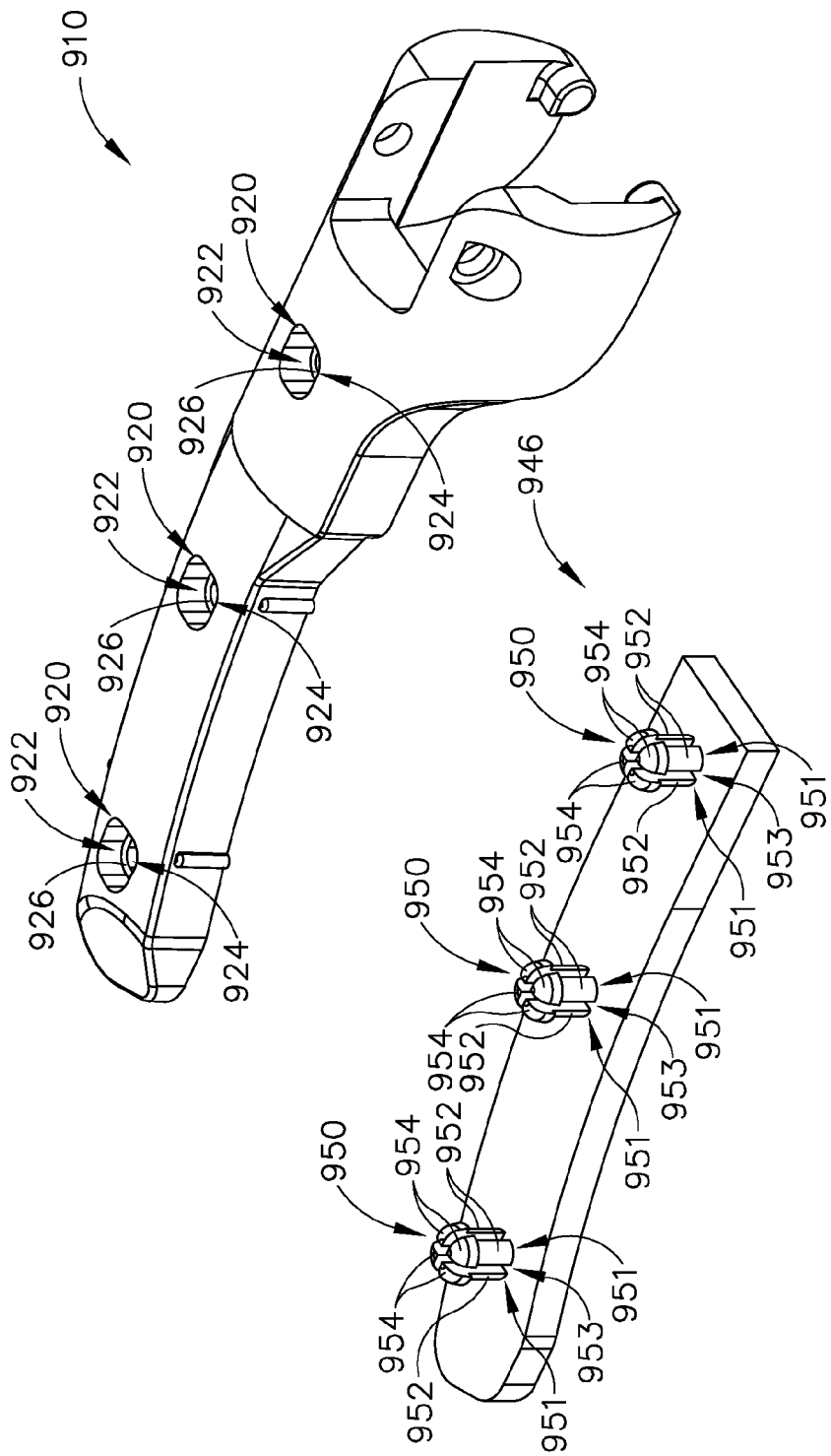
FIG. 71 depicts an exploded perspective view of the clamp arm of FIG. 70.
Figure 72:
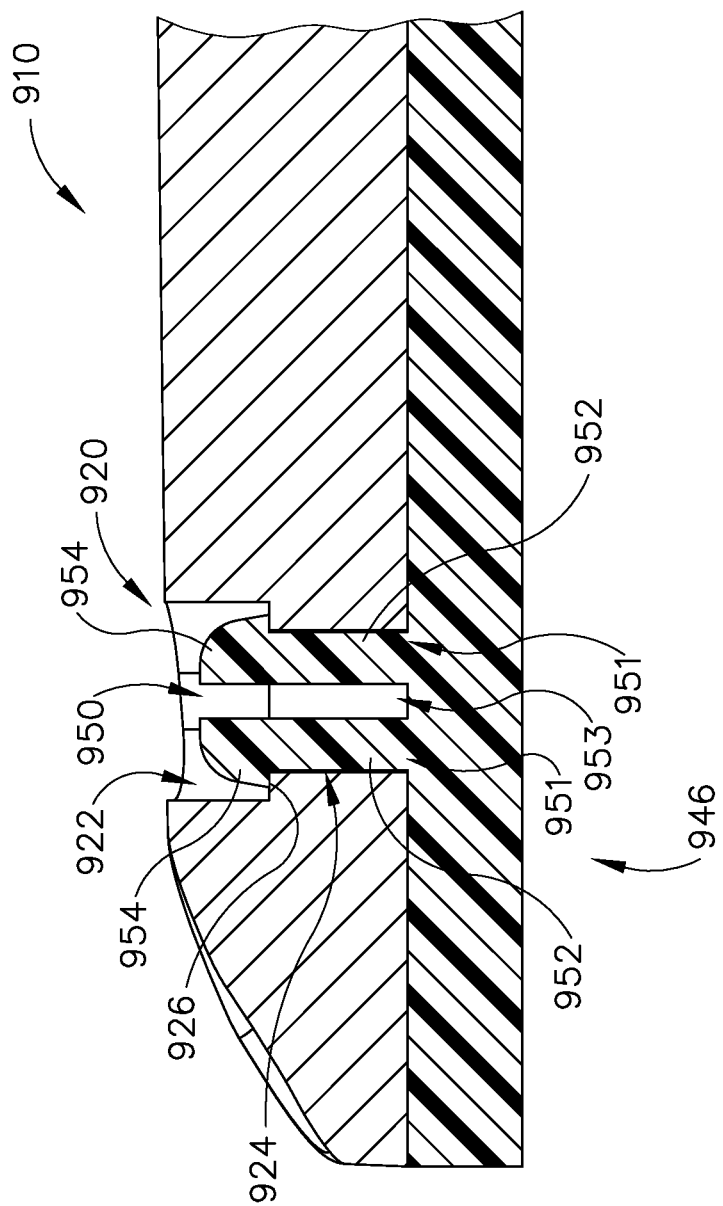
FIG. 72 depicts a partial side cross-sectional view of the clamp arm of FIG. 70, with the cross-section taken along 72-72 of FIG. 70.

FIGS. 70-72 show yet another exemplary alternative clamp arm (910) that may be readily incorporated into instrument (100) described above. Clamp arm (910) is substantially the same as clamp arm (710) described above unless otherwise noted herein. For instance, like with clamp arm (710), clamp arm (910) is configured to permit snap-fit coupling and decoupling of a clamp pad (946) to clamp arm (910). However, unlike clamp arm (710) and clamp pad (746), clamp arm (910) and clamp pad (946) of the present example comprise multiple snap-fit mechanisms that couple clamp pad (946) to clamp arm (910).

FIG. 71 shows clamp pad (946) decoupled from clamp arm (910). As can be seen, clamp pad (946) comprises a plurality of generally substantially similar snap assemblies (950). Snap assemblies (950) are disposed along the central longitudinal axis of clamp pad (946). Snap assemblies (950) are generally spaced at unequal distances from each other. However, it should be understood that in other examples snap assemblies (950) are spaced equal distances from each other. While the present example is shown as having three snap assemblies (950), other examples may include any suitable number of snap assemblies (950).

Each snap assembly (950) defines a generally mushroom shaped assembly. Such a shape is formed by four individual snap members (951) arranged in a generally circular, semi-circular, or ovular pattern. To permit deflection of each individual snap member (951), snap members (951) are spaced from each other to define a gap (953) between each snap member (951) of a given snap assembly (950). It should be understood that each gap (953) is not limited to the particular gap size shown herein. In other examples, each gap (953) is larger or smaller and size than the particular size shown. By way of example only, in some examples gap (953) is generally a function of the physical characteristics of each snap assembly (950). For instance, larger or smaller snap members (951) may include larger or smaller corresponding gap (953) size.

Each snap member (951) comprises an elongate resilient portion (952) and a generally semi-hemispherical lock tooth (954). Resilient portion (952) extends upwardly from the upper face of clamp pad (946). Because clamp pad (946) is comprised of a generally flexible material such as PTFE, resilient portion (952) generally also has some flexibility but is resiliently biased toward the vertical positioning shown in FIG. 71. As will be described in greater detail below, the flexible yet resilient character of resilient portion (952) is configured to permit form a snap-fit when clamp pad (946) is inserted onto clamp arm (910).

Lock tooth (954) of each snap member (951) protrudes laterally outwardly from resilient portion (952). As will be described in greater detail below, lock teeth (954) of a given snap assembly (950) are generally configured to engage at least a portion of clamp arm (910) to selectively secure clamp pad (946) to clamp arm (910). As can be seen, the lock teeth (954) of a given snap assembly (950) together define the "cap" of the mushroom shape of each snap assembly (950). Although the shape of lock tooth (954) is generally semi-hemispherical, it should be understood that numerous other shapes may be used.

As is also seen in FIG. 71, clamp arm (910) includes a plurality of lock features (920). In the present example, each lock feature (920) corresponds to an associated snap member (950). Thus, each lock feature (920) is configured to receive a corresponding snap member (950) to thereby fasten clamp pad (946) to clamp arm (910). As is best seen in FIG. 72, each lock feature (920) comprises a first opening (922) and a second opening (924). First opening (922) is in communication with second opening (924) such that openings (922, 924) together extend vertically through clamp arm (910). However, second opening (924) comprises a size that is smaller relative to first opening (922). This difference in sizing defines a lock ledge (926) in clamp arm (910). Lock ledge (926) is a generally flat surface that is configured to engage with each lock tooth (954) of a given snap assembly (950). It should be understood that openings (922, 924) of the present example comprise a generally cylindrical (circular or elliptical) that corresponds to the shape defined by the combination of the snap members (951) of a given snap assembly (950). Thus, lock ledge (926) generally extends around the resilient portions (952) of a given snap assembly (951) extending outwardly therefrom.

Figure 73:
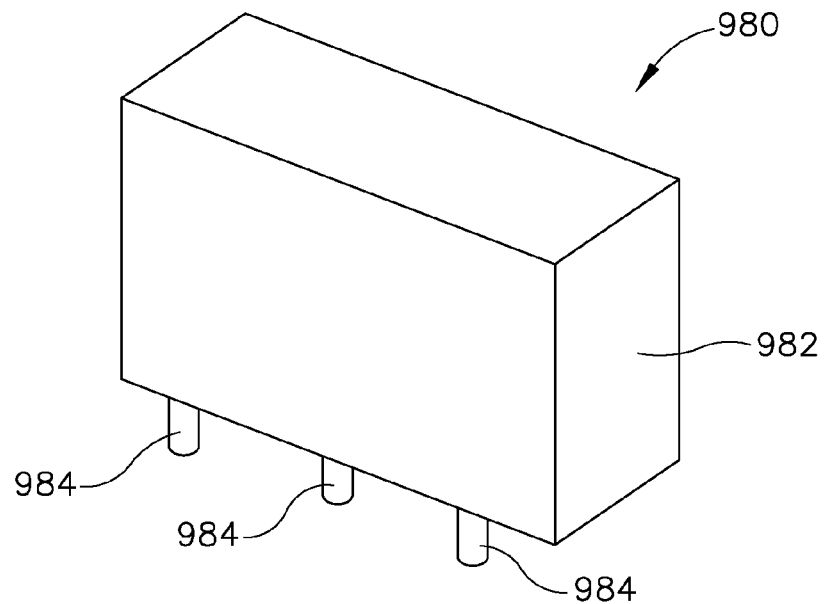
FIG. 73 depicts a perspective view of an exemplary removal tool for use with the clamp arm of FIG. 70.

FIG. 73 shows an exemplary removal tool (980) that may be used with clamp arm (910) to removed clamp pad (946) from clamp arm (910). Tool (980) comprises a handle portion (982) and a plurality of engagement portions (984). Handle portion (982) is configured to be gripped by an operator to manipulate tool (980). Engagement portions (984) are configured to engage each snap assembly (950) of clamp pad (946) to disengage clamp pad (946) from clamp arm (910), as will be described in greater detail below.

Figure 74:
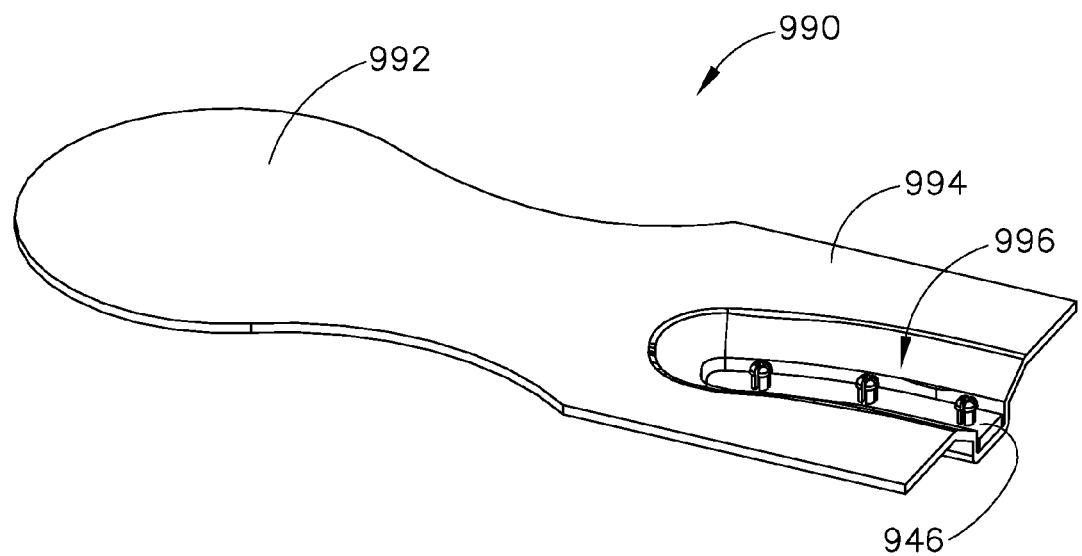
FIG. 74 depicts a perspective view of an exemplary attachment tool for use with the clamp arm of FIG. 70.

FIG. 74 shows an exemplary assembly tool (990) that may be used in conjunction with clamp pad (946) to attach clamp pad (946) to clamp arm (910). Tool (990) comprises a grip portion (992) and a pad portion (994). Grip portion (992) is configured to generally provide an area for gripping by an operator such that an operator more readily manipulate clamp pad (946). Pad portion (994) includes a pad channel (996) that is configured to receive clamp pad (946). Although not shown, it should be understood that in some examples pad channel (996) includes fastening features that are configured to hold clamp pad (946) temporarily within pad channel (996) while clamp pad (946) is being manipulated by an operator.

Figure 75:
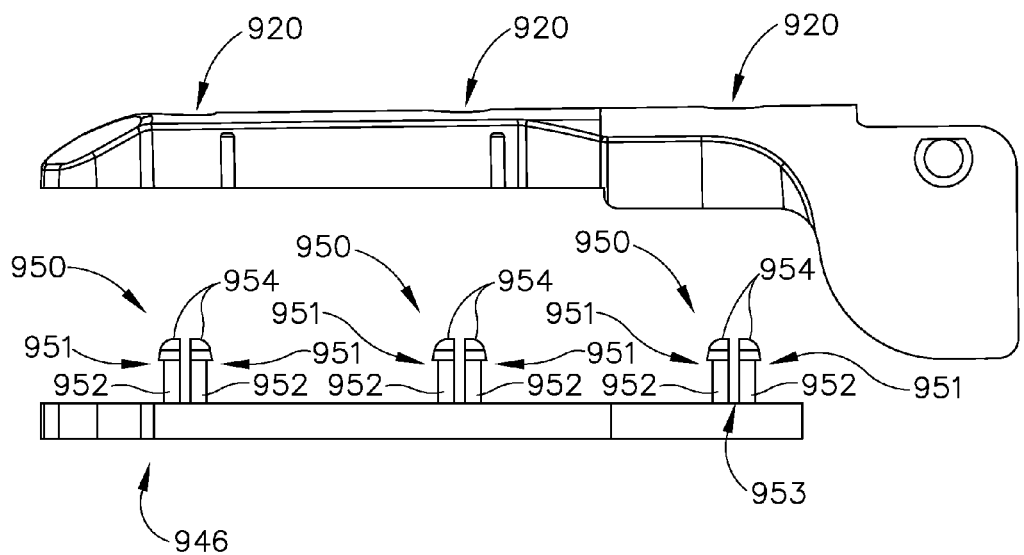
FIG. 75 depicts a side elevational view of the clamp arm of FIG. 70, with a clamp pad positioned adjacent to the clamp arm.
Figure 76:
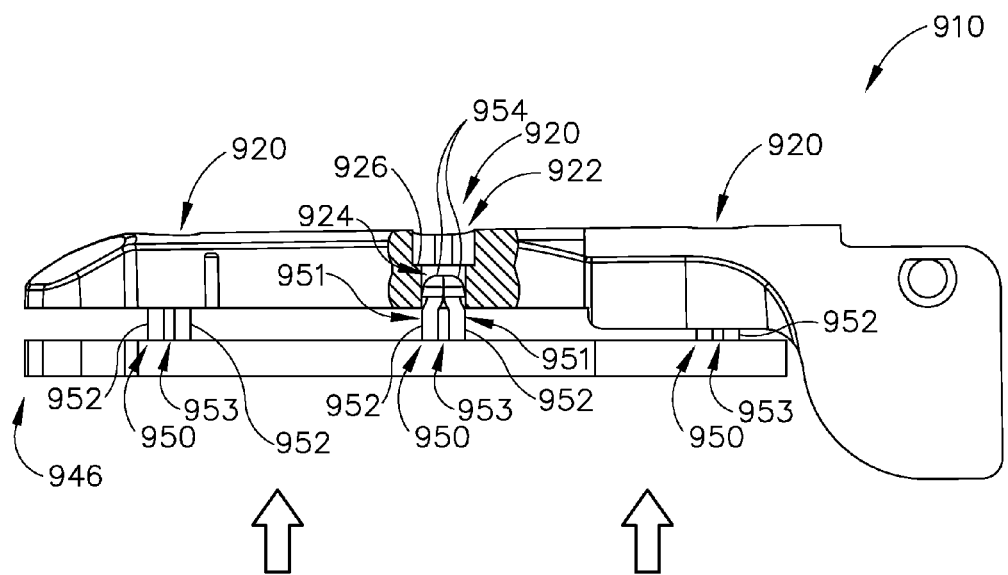
FIG. 76 depicts another side elevational view of the clamp arm of FIG. 70, with the clamp pad of FIG. 75 partially inserted into the clamp arm.
Figure 77:
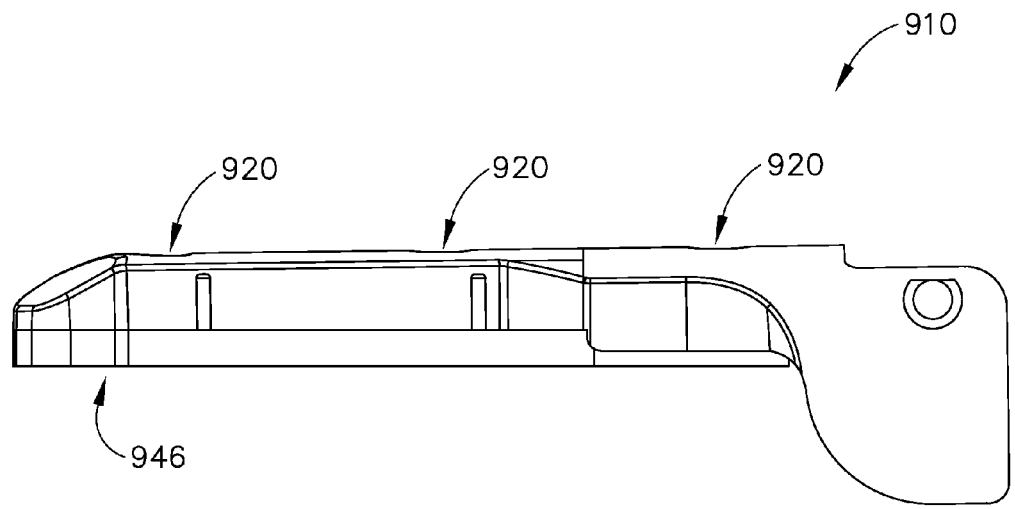
FIG. 77 depicts still another side elevational view of the clamp arm of FIG. 70, with the clamp pad of FIG. 75 fully inserted into the clamp arm.

FIGS. 75-77 show an exemplary procedure for attaching clamp pad (946) to clamp arm (910). As can be seen in FIG. 75, clamp pad (946) is attached to clamp arm (910) by an operator first aligning each snap assembly (950) of clamp pad (946) with each lock feature (920) of clamp arm (910). An operator then pushes clamp pad (946) upwardly such that each snap assembly (950) engages with each lock feature (920), as shown in FIG. 76. As can be seen, this upward motion causes the each snap member (951) of a given snap assembly (950) to deflect inwardly as each snap assembly (950) is pushed into second opening (924) of a given lock feature (920).

Continued upward movement of clamp pad (946) will result in lock teeth (954) entering first opening (922) of lock features (920). Once lock teeth (954) are fully disposed within first opening (922), each snap member (951) will return to the position corresponding to the position shown in FIG. 71 and lock teeth (954) will engage lock ledge (926). Such engagement between each lock ledge (926) and lock teeth (954) will fasten clamp pad (946) to clamp arm (910) in the position shown in FIG. 77.

It should be understood that although not shown, clamp pad (946) may be used in the procedure described above in conjunction with attachment tool (990) described above. In some examples it may be desirable to use such an attachment tool to enhance the ease by which an operator may grip clamp pad (946). Of course, such an attachment tool is merely optional and is omitted in some examples.

Figure 78:
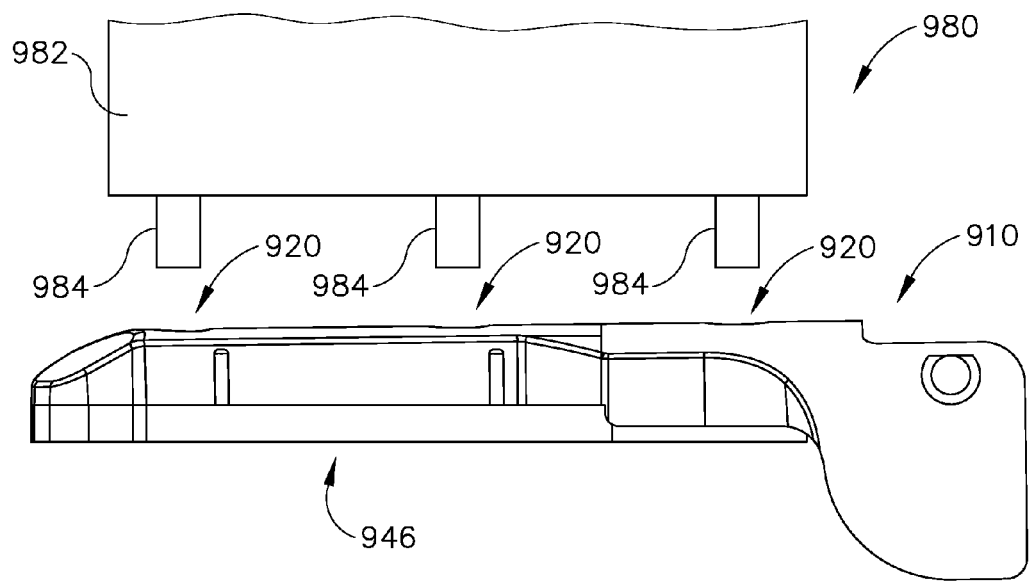
FIG. 78 depicts another side elevational view of the clamp arm of FIG. 70, with the removal tool of FIG. 73 adjacent to the clamp arm.
Figure 79:
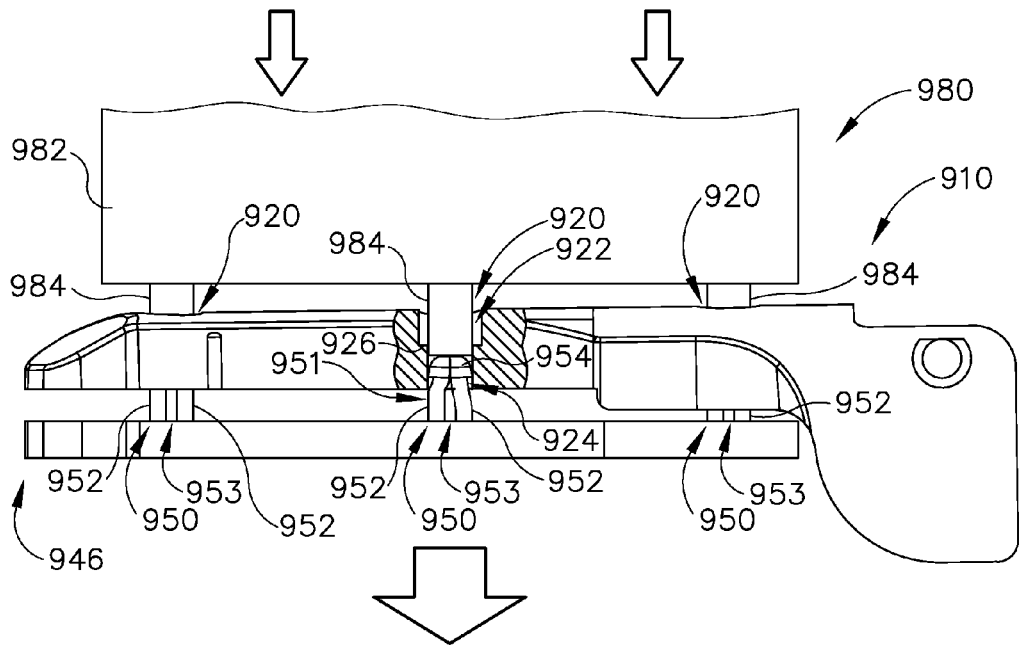
FIG. 79 depicts another side elevational view of the clamp arm of FIG. 70, with the removal tool of FIG. 73 partially to the clamp arm.
Figure 80:
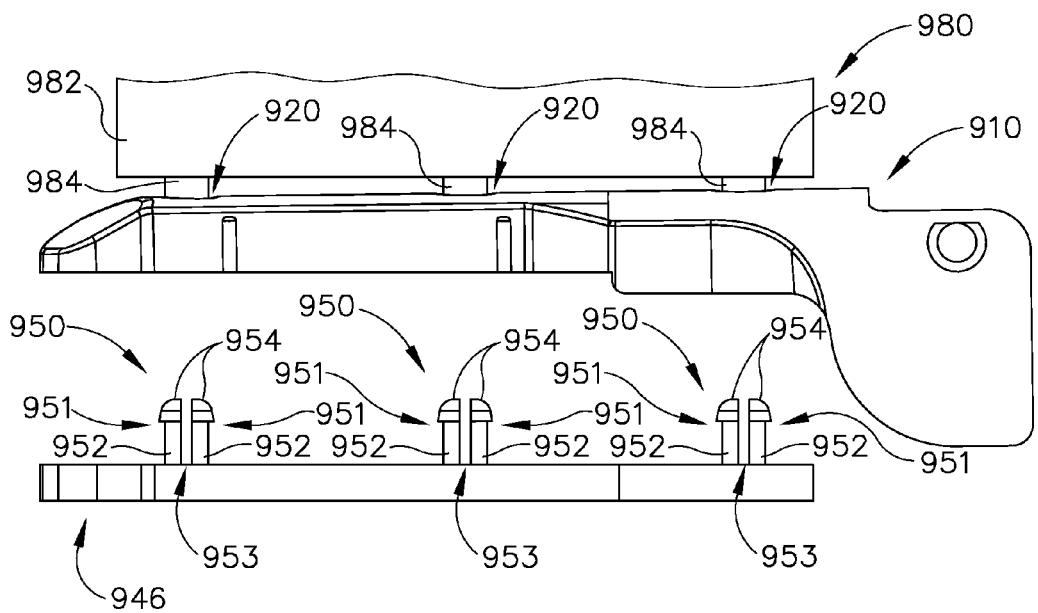
FIG. 80 depicts another side elevational view of the clamp arm of FIG. 70, with the removal tool of FIG. 73 fully engaged with the clamp arm and the clamp pad of FIG. 75 fully removed.
Figure 81:
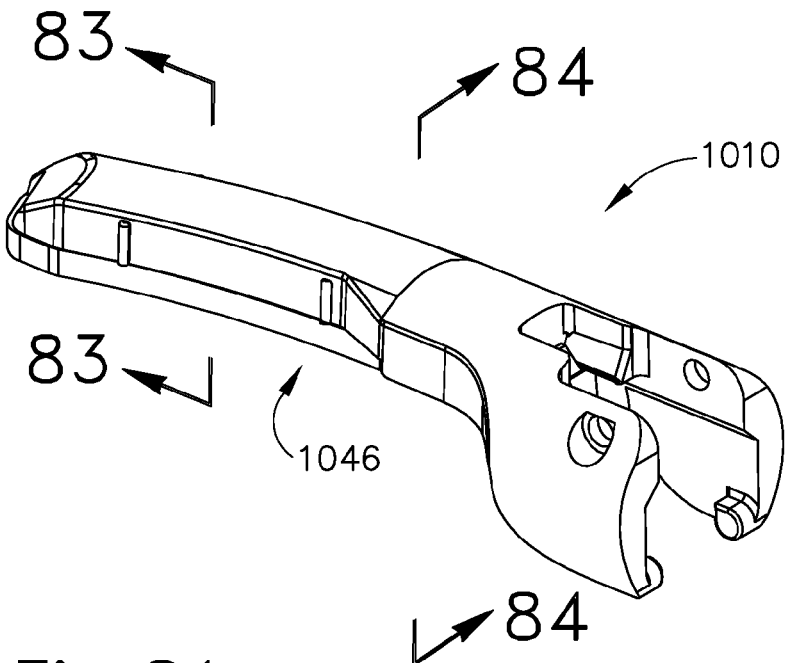
FIG. 81 depicts a perspective view of yet another clamp arm for use with the instrument of FIG. 2.

After clamp pad (946) has been attached to clamp arm (910), an operator may perform a surgical procedure using clamp arm (910) and instrument (100). At the conclusion of such a procedure or at any point during the procedure an operator may desire to decouple clamp pad (946) from clamp arm (910) to clean clamp pad (946) or otherwise replace clamp pad (946) with a new identical or different clamp pad (946). FIGS. 78-80 show an exemplary procedure for detachment of clamp pad (946) from clamp arm (910).

As can be seen in FIG. 78, the procedure initially begins with removal tool (980) being positioned by an operator in a position adjacent to the top of clamp arm (910). In particular, in this initial position, removal tool (980) is positioned such that each engagement portion (984) is positioned adjacent to a corresponding lock feature (920) of clamp arm (910).

Once tool (980) is positioned as described above, an operator may begin removal by pushing tool downwardly. As can be seen in FIG. 79, downward movement of tool (980) causes engagement portions (984) to engage a respective snap assembly (950) of clamp pad (946). This engagement causes each snap feature (951) of a given snap assembly (950) to deform inwardly such that each lock tooth (954) of each snap feature (951) may fit into second opening (924) of clamp arm (910). With each snap assembly (950) deformed, further downward motion of tool (980) will force each snap assembly (950) out of second opening (924), thereby decoupling clamp pad (946) from clamp arm (910), as shown in FIG. 80.

To remove clamp pad (846) an operator may simply manually push each snap member (850) of clamp pad (846) out of engagement with each lock feature (820) of clamp arm (810) while simultaneously pushing clamp pad (846) downwardly. However, in some examples, manual removal of clamp pad (846) may be less desirable because manipulating each snap member (850) out of engagement with each lock feature (820) may be challenging or cumbersome with some operators. For instance, because the present example includes four snap members (850), all four snap members (850) may be disengaged before clamp pad (846) is removed. This may require simultaneous manipulation of all four snap members (850) or otherwise some previously disengaged snap members (850) may re-engage during disengagement of other snap members (850). Accordingly, in some instances it may be desirable to use a tool or other apparatus in conjunction with clamp arm (810) to more readily remove clamp pad (846).

VI. Exemplary Alternative Claim Pads with Resilient Slide-In Features

In some instances, it may be desirable to provide clamp arms (144) and/or clamp pads (146) with features configured to allow an operator to selectively remove or otherwise decouple clamp pad (146) from clamp arm (114). One merely exemplary way in which to provide such selective operation to clamp arm (144) is to provide clamp arm (144) and/or clamp pad (146) with features operable to permit longitudinal insertion of clamp pad (146) from the distal end of clamp arm (144). Additionally, features may be included in clamp arm (144) and/or clamp pad (146) to selectively fix the longitudinal position of clamp pad (146) relative to clamp arm (144). Such features may be desirable because such features may permit an operator to more easily remove of clamp pad (146). The examples described below provide various examples of features and techniques configured to allow an operator to selectively remove or otherwise decouple a portion of a clamp arm similar to clamp arm (144). While various examples of features operable to provide such selective operation in clamp arm (144) will be described in greater detail below, other examples will be apparent to those of ordinary skill in the art according to the teachings herein. Similarly, various suitable ways in which the below teachings may be combined with the teachings of the various references cited herein will be apparent to those of ordinary skill in the art.

A. Exemplary Clamp Pad with Resilient Slide-In Latch

FIGS. 81-84 show yet another exemplary alternative clamp arm (1010) that may be readily incorporated into instrument (100) described above. Clamp arm (1010) is substantially the same as clamp arm (144) described above unless otherwise noted herein. For instance, like with clamp arm (144), clamp arm (1010) is configured to receive a clamp pad (1046) by sliding clamp pad (1046) longitudinally relative to clamp arm (1010). However, unlike clamp arm (144) described above, clamp arm (1010) of the present example is configured to receive clamp pad (1046) from the distal end of clamp arm (1010) rather than the proximal end.

Figure 82:
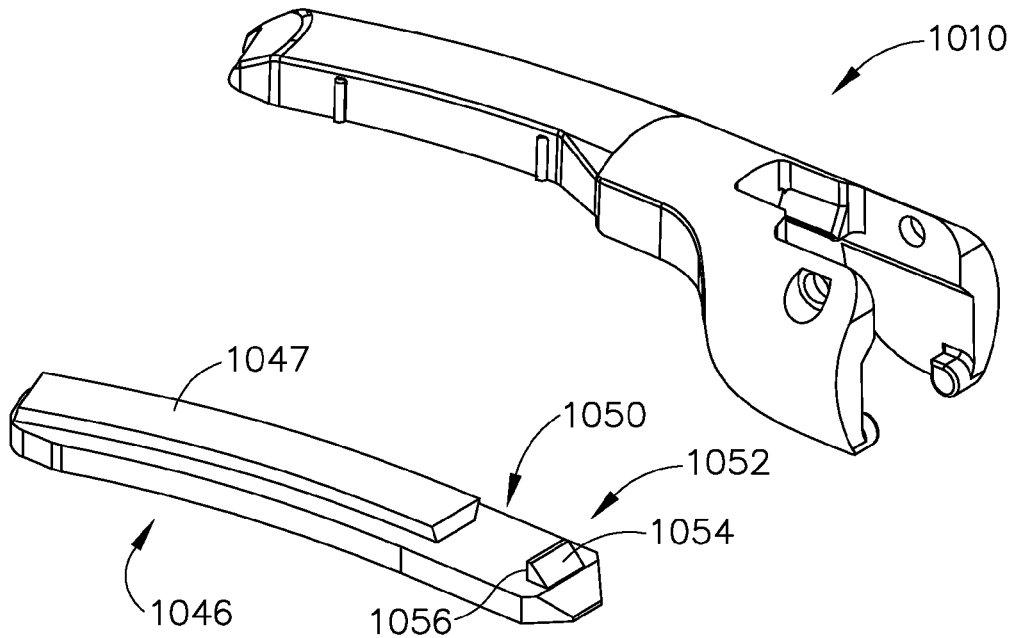
FIG. 82 depicts an exploded perspective view of the clamp arm of FIG. 81.

As is best seen in FIG. 82, clamp pad (1046) of the present example comprises a dovetailed key (1047) extending proximally from the distal end of clamp pad (1046). Key (1047) is substantially the same as key (147) described above. For instance, like with key (147), key (1047) of the present example flairs outwardly as key (1047) extends upwardly away from the upper face of clamp pad (1046). Thus, it should be understood that like with key (147), key (1047) of the present example is configured to be received within a corresponding channel (1040) of clamp arm (1010).

Unlike key (147), key (1047) of the present example terminates distally of the proximal end of clamp pad (1046). This configuration defines an open portion (1050) in clamp pad (1046). As will be described in greater detail below, such a configuration permits clamp pad (1046) to selectively fasten to clamp arm (1010) when clamp pad (1046) is inserted into clamp arm (1010).

Clamp pad (1046) further includes a proximal snap member (1052). Snap member (1052) is integral with clamp pad (1046), extending upwardly from the upper face of clamp pad (1046). Snap member (1052) comprises a ramped portion (1054) and a vertical portion (1056). Ramped portion (1054) is generally oriented at an acute angle relative to the upper face of clamp pad (1046). Although ramped portion (1054) is shown as being oriented at a particular angle, it should be understood that any other suitable acute angle may be used. As will be described in greater detail below, ramped portion (1054) is generally configured to deflect at least a portion of clamp pad (1046) away from clamp arm (1010) as clamp pad (1046) is inserted onto clamp arm (1010).

Vertical portion (1056) is oriented generally perpendicularly relative to the upper face of clamp pad (1046). Although this suggests that vertical portion (1056) is angled at a generally 90 degree angle relative to the flat face of clamp pad (1046), it should be understood that no such limitation is intended. Indeed, in some examples vertical portion (1056) is angled relative to the flat face of clamp pad (1046) at a relatively large acute angle or a relatively small obtuse angle. Regardless of the angle of vertical portion (1056), it should be understood that vertical portion (1056) is generally configured to engage at least a portion of clamp arm (1010) to retain clamp pad (1046) within clamp arm (1010).

Figure 83:
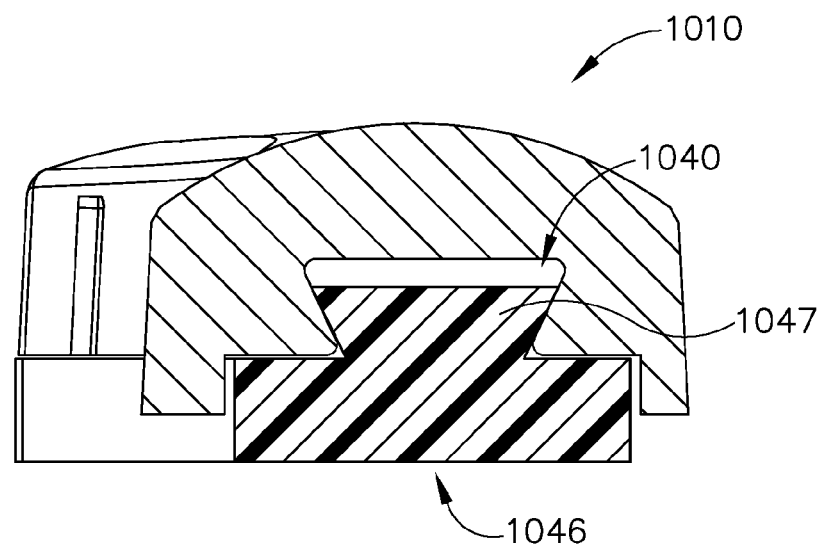
FIG. 83 depicts a front cross-sectional view of the clamp arm of FIG. 81, with the cross-section taken along line 83-83 of FIG. 81.

As described above, clamp arm (1010) comprises a channel (1040) extending longitudinally through clamp arm (1010). As is best seen in FIG. 83, channel (1040) has a transverse cross-sectional shape corresponding to the shape of key (1047) of clamp pad (1046). Accordingly, channel (1040) of the present example comprises a generally dovetailed shape. It should be understood that in examples where key (1047) comprises an alternative shape (e.g., T-shape), channel (1040) may be correspondingly altered to accommodate key (1047).

Figure 84:
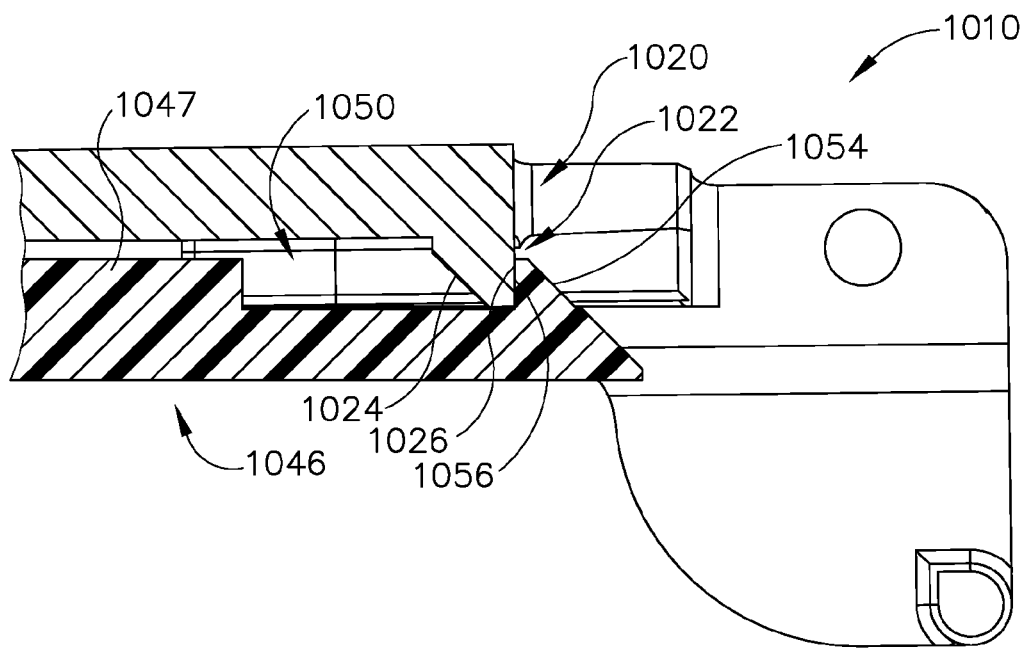
FIG. 84 depicts a partial side cross-sectional view of the clamp arm of FIG. 81, with the cross-section taken along line 84-84 of FIG. 81.

As can best be seen in FIG. 84, clamp arm (1010) further comprises a lock assembly (1020). Lock assembly (1020) includes a generally rigid tooth (1022) extending downwardly into channel (1040) at the proximal end of channel (1040). Tooth (1022) comprises an angled portion (1024) and a vertical portion (1026). Angled portion (1024) is similar to ramped portion (1054) described above with respect to clamp pad (1046). In particular, angled portion (1024) generally corresponds to ramped portion (1054) of clamp pad (1046). This correspondence permits angled portion (1024) to engage ramped portion (1054) to more readily deflect clamp pad (1046), as will be described in greater detail below. It should be understood that angled portion (1024) may be modified in some examples to utilize other suitable angles while still improving the functionality of ramped portion (1054).

Vertical portion (1026) generally corresponds to vertical portion (1056) of clamp pad (1046). As can be seen in FIG. 84, vertical portion (1026) is configured to engage with vertical portion (1056) of clamp pad (1046). As will be described in greater detail below, engagement between vertical portion (1026) of clamp arm (1010) and vertical portion (1056) of clamp pad (1046) is generally operable to selectively prevent distal longitudinal movement of clamp pad (1046) relative to clamp arm (1010). It should be understood that in examples where vertical portion (1056) of clamp pad (1046) is oriented at a different angle, vertical portion (1026) of clamp arm (1010) may also be correspondingly different to accommodate such an angle while retaining the same functionality described above.

Figure 85:
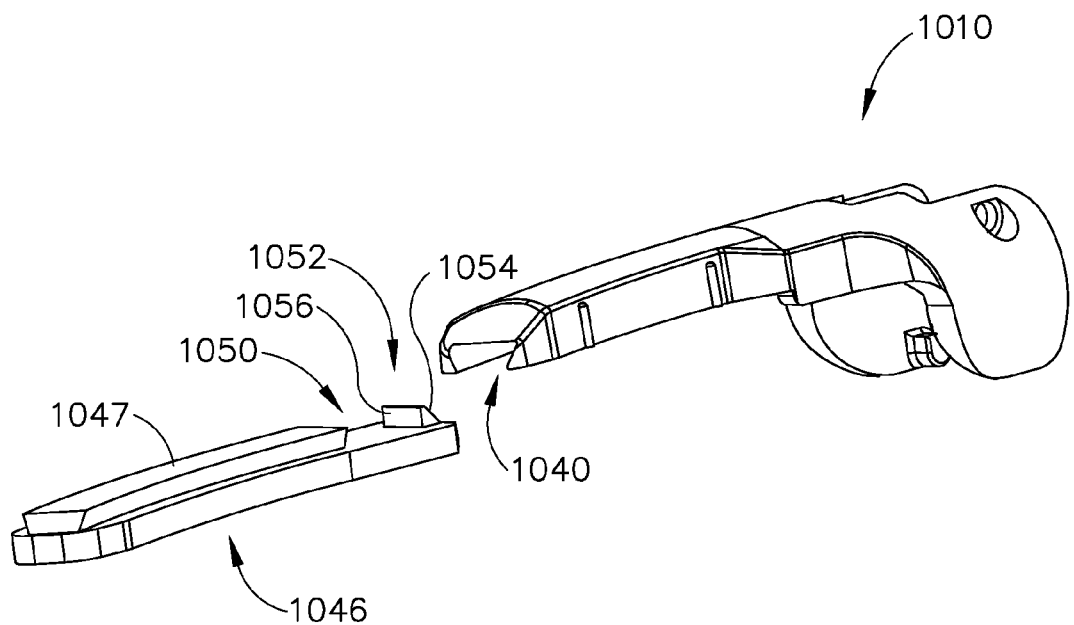
FIG. 85 depicts another perspective view of the clamp arm of FIG. 81, with a clamp pad adjacent to the clamp arm.

FIGS. 85-90 show an exemplary procedure for fastening clamp pad (1046) to clamp arm (1010). As can be seen in FIG. 85, clamp pad (1046) may be initially positioned adjacent to the distal end of clamp arm (1010). Channel (1040) of the present example extends through the distal end of clamp arm (1010). Thus, channel (1040) is accessible from the distal end of clamp arm (1010). Accordingly, an operator may begin to fasten clamp pad (1046) to clamp arm (1010) by moving clamp pad (1046) longitudinally such that key (1047) enters channel (1040).

Figure 86:
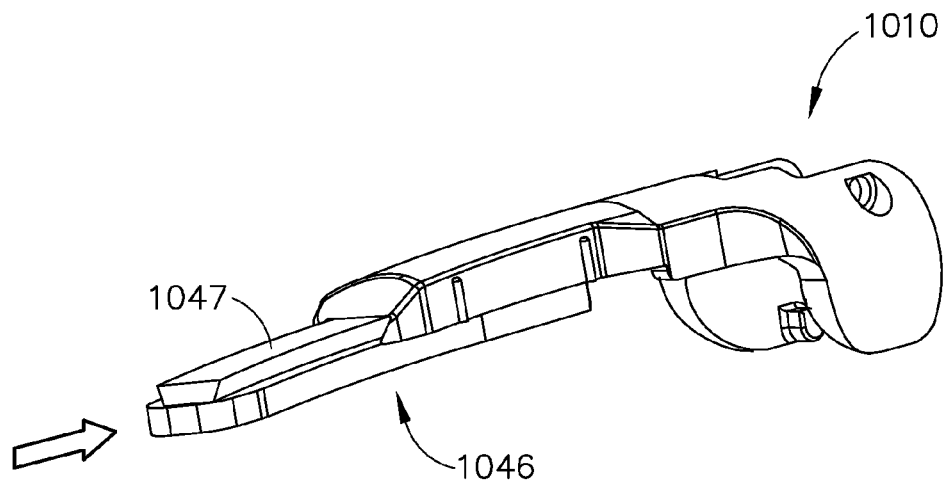
FIG. 86 depicts still another perspective view of the clamp arm of FIG. 81, with the clamp pad of FIG. 85 partially inserted into the clamp arm.
Figure 88:
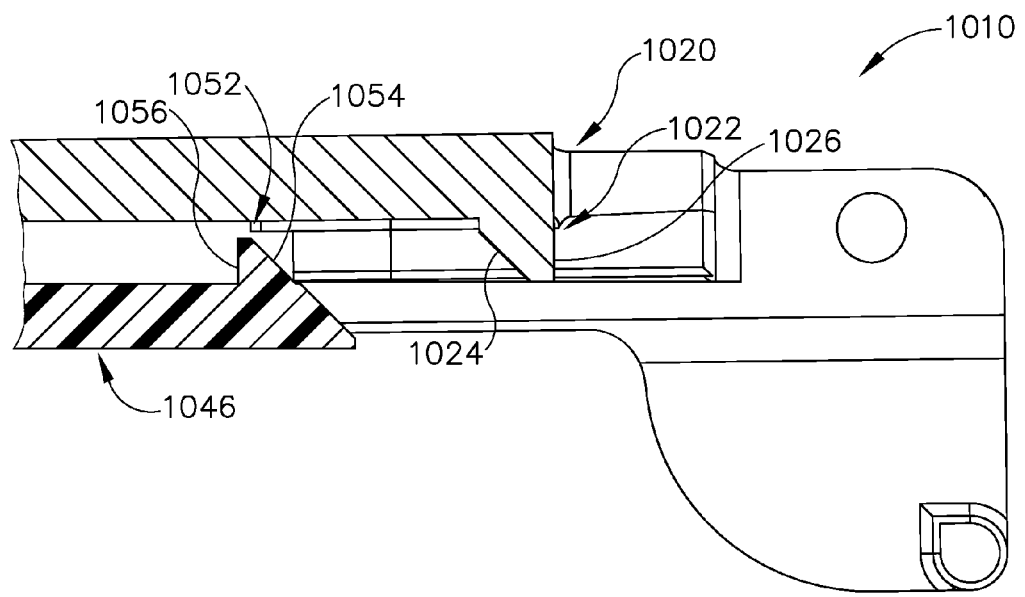
FIG. 88 depicts another partial side cross-sectional view of the clamp arm of FIG. 81, with the clamp pad of FIG. 85 partially inserted into the clamp arm.

Once key (1047) enters channel (1040), clamp pad (1046) may be slid longitudinally relative to clamp arm (1010) through the position shown in FIG. 86. FIG. 88 shows the corresponding position of snap member (1052) of clamp pad (1046) relative to lock assembly (1020) when clamp pad (1046) is in the position shown in FIG. 86.

Figure 87:
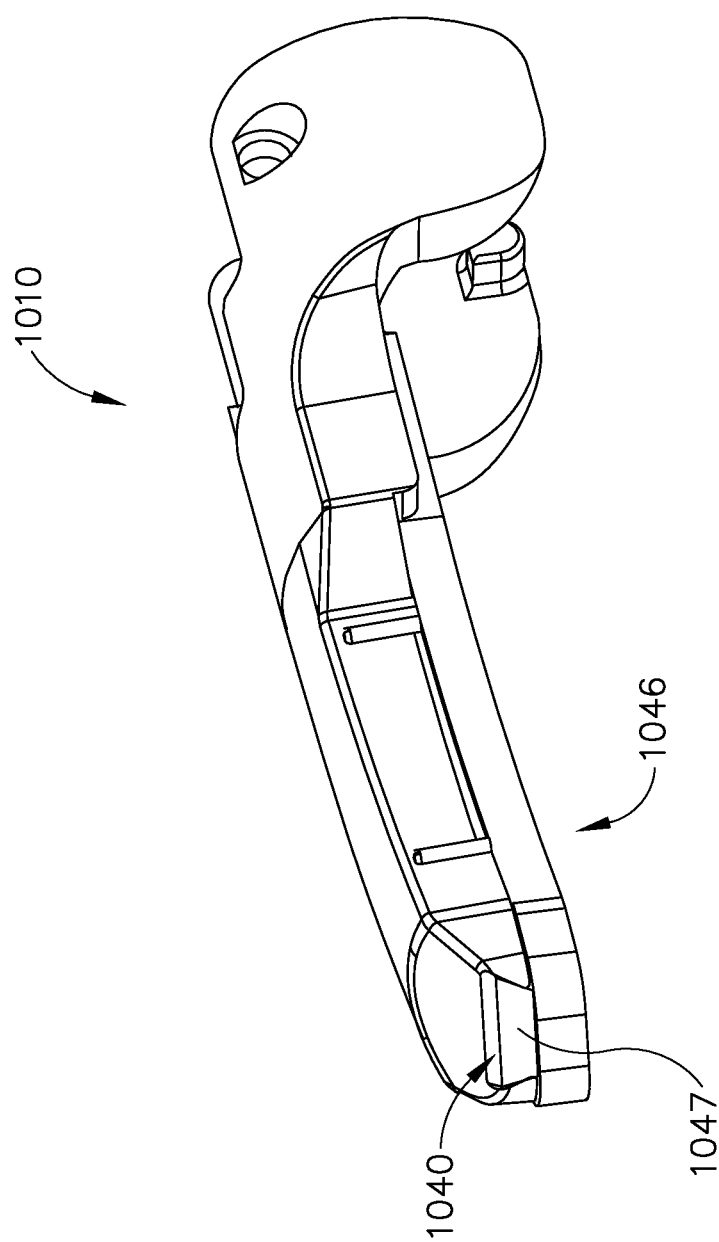
FIG. 87 depicts yet another perspective view of the clamp arm of FIG. 81, with the clamp pad of FIG. 85 fully inserted into the clamp arm.
Figure 89:
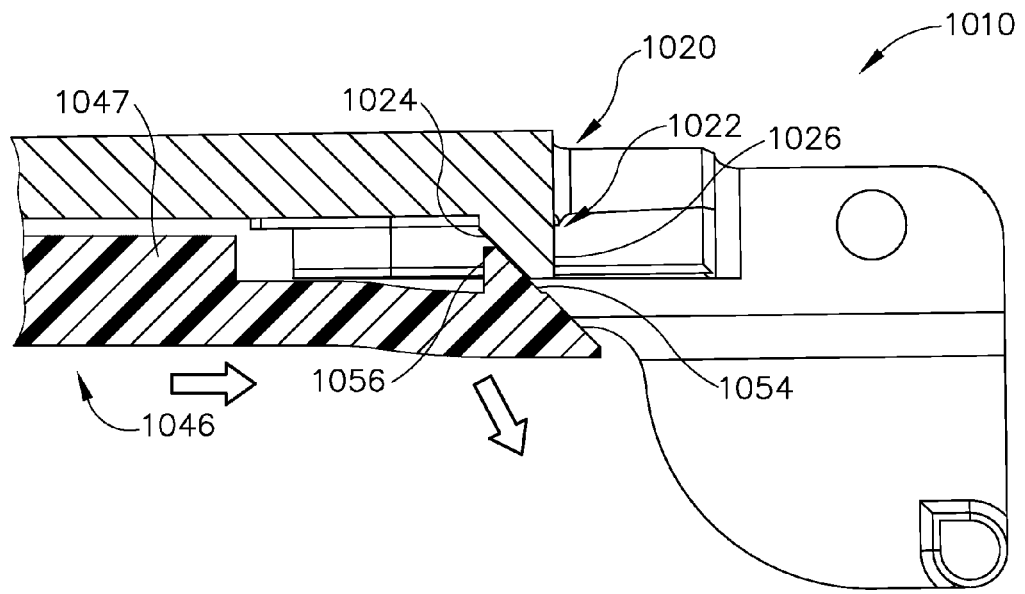
FIG. 89 depicts still another partial side cross-sectional view of the clamp arm of FIG. 81, with the clamp pad of FIG. 85 engaging a lock tooth of the clamp arm.

As clamp pad (1046) is moved further proximally toward the position shown in FIG. 87, snap member (1052) will begin to engage lock assembly (1020) as shown in FIG. 89. This causes ramped portion (1054) of snap member (1052) to engage with angled portion (1024) of lock tooth (1022). It should be understood that because clamp pad (1046) is comprised of a generally flexible material such as PTFE, the corresponding surfaces of ramped portion (1054) and angled portion (1024) will cause snap member (1052) to deflect away from lock tooth (1022). Further proximal movement of clamp pad (1046) will cause additional deflection, until snap member (1052) moves past angled portion (1024) of lock tooth (1022).

Figure 90:
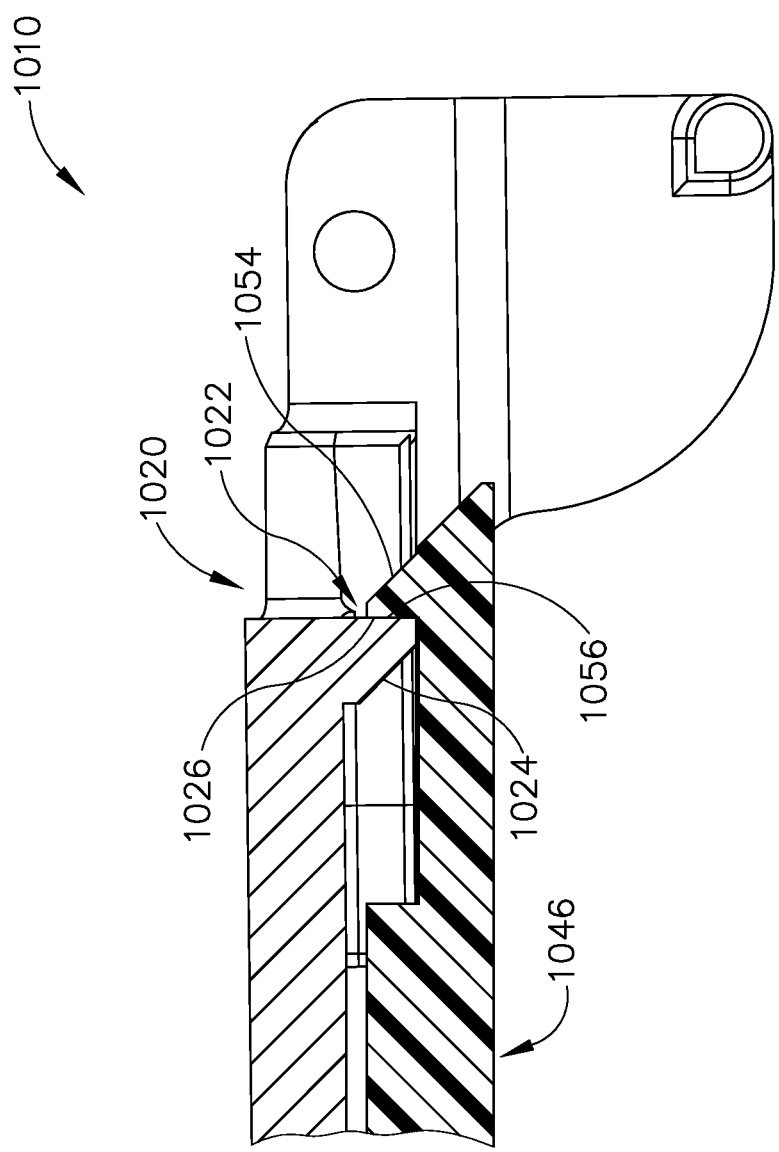
FIG. 90 depicts yet another partial side cross-sectional view of the clamp arm of FIG. 81, with the clamp pad of FIG. 85 fully inserted into the clamp arm.

Once snap member (1052) passes angled portion (1024) of lock tooth (1022), vertical portion (1026) of lock tooth (1022) will permit snap member (1052) to return to a non-deflected state as shown in FIG. 90. In this position, vertical portion (1056) of clamp pad (1046) will engage with vertical portion (1026) of clamp arm (1010). Once vertical portions (1026, 1056) are engaged, distal translation of clamp pad (1046) is prevented and clamp pad (1046) is selectively fastened in the position shown in FIG. 87.

Figure 91:
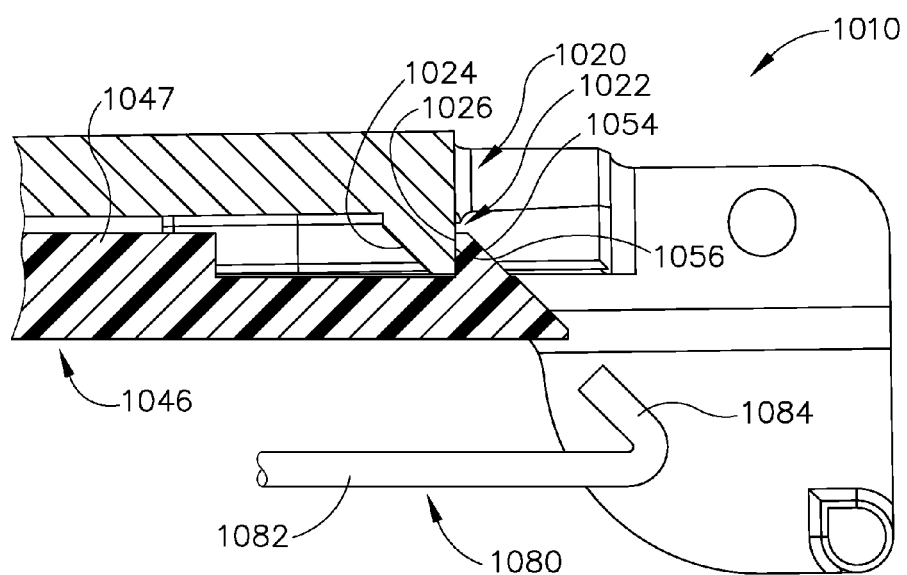
FIG. 91 depicts yet another partial side cross-sectional view of the clamp arm of FIG. 81, with a tool adjacent to the clamp pad of FIG. 85.
Figure 92:
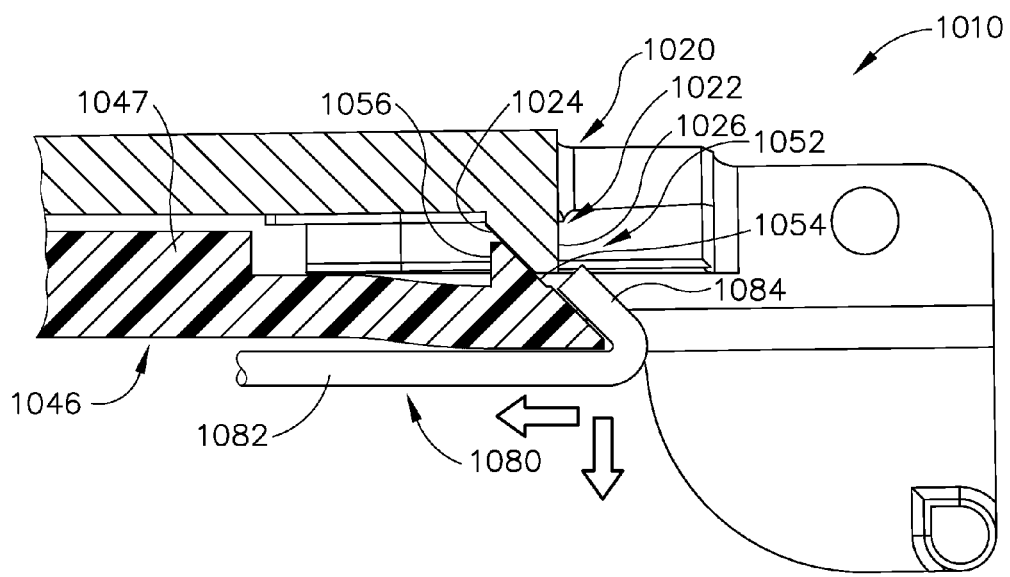
FIG. 92 depicts yet another partial side cross-sectional view of the clamp arm of FIG. 81, with the tool of FIG. 91 grasping at least a portion of the clamp pad of FIG. 85.
Figure 93:
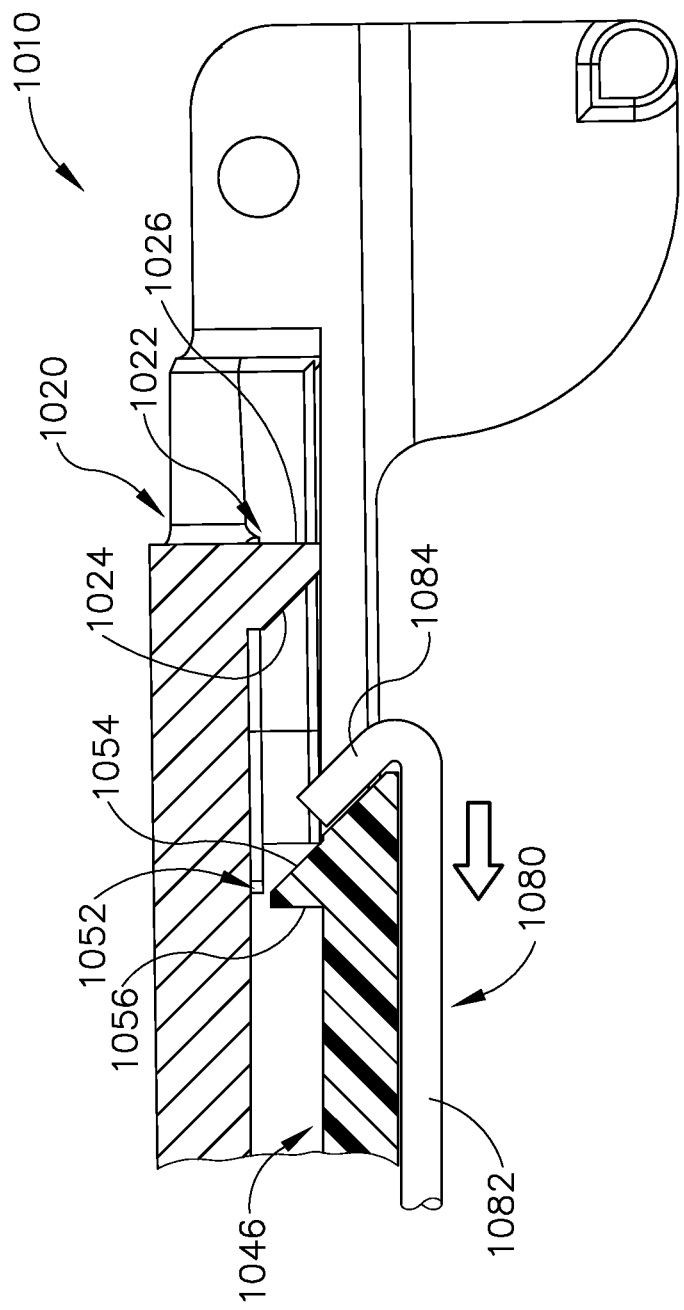
FIG. 93 depicts yet another partial side cross-sectional view of the clamp arm of FIG. 81, with the clamp pad of FIG. 85 partially removed from the clamp arm.

After clamp pad (1046) has been attached to clamp arm (1010), an operator may perform a surgical procedure using clamp arm (1010) and instrument (100). At the conclusion of such a procedure or at any point during the procedure an operator may desire to decouple clamp pad (1046) from clamp arm (1010) to clean clamp pad (1046) or otherwise replace clamp pad (1046) with a new identical or different clamp pad (1046). FIGS. 91-93 show an exemplary procedure for detachment of clamp pad (1046) from clamp arm (1010).

As can be seen in FIG. 91, an operator may use a detachment tool (1080) for removal of clamp pad (1046). Although many other suitable detachment tools (1080) may be used, detachment tool (1080) of the present example comprises a handle portion (1082) and a hook portion (1084). Handle portion (1082) comprises an elongate rod that is configured for gripping by an operator to manipulate hook portion (1084). Hook portion (1084) is generally hook shaped (1084) to permit aid an operator in manipulating clamp pad (1046).

Hook portion (1084) of tool (1080) is initially manipulated by an operator into a position adjacent to the proximal end of clamp pad (1046). An operator may then move hook portion (1084) upwardly to grasp the proximal end of clamp pad (1046) as shown in FIG. 92.

With hook portion (1084) grasping proximal end of clamp pad (1046), an operator may pull downwardly and distally on tool (1080). The downward force vector will deflect clamp pad (1046) as shown in FIG. 92 such that snap member (1052) of clamp pad (1046) will clear lock tooth (1022) of clamp arm (1010). The distal force vector will cause clamp pad (1046) to be pulled distally through channel (1040) and out of the distal end of clamp arm (1010), thereby removing clamp pad (104) from clamp arm (1010), as shown in FIG. 93. Once clamp pad (1046) is removed, an operator may optionally replace clamp pad (1046) with a new different clamp pad or new identical clamp pad (1046) using the same assembly procedure described above.

B. Exemplary Clamp Pad with Detent Features

Figure 94:
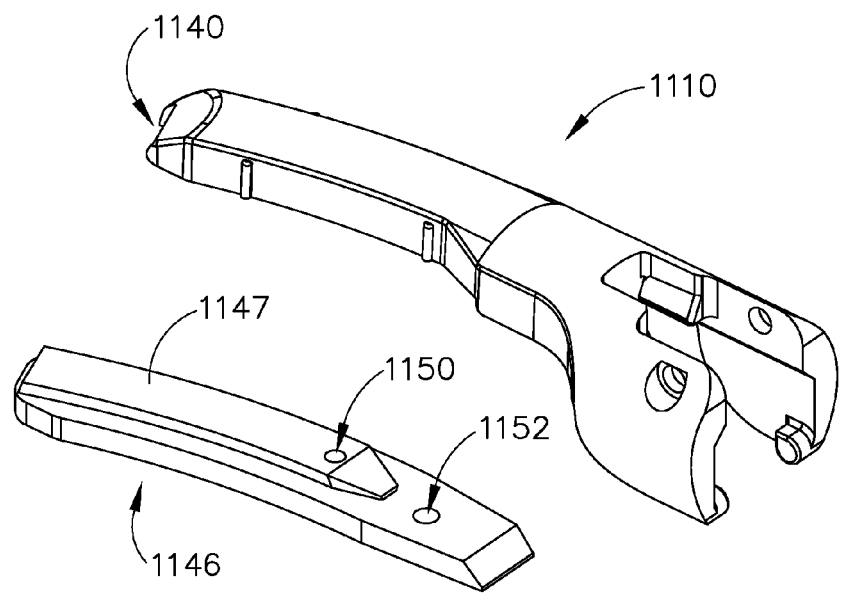
FIG. 94 depicts an exploded perspective view of yet another clamp arm for use with the instrument of FIG. 2.
Figure 95:
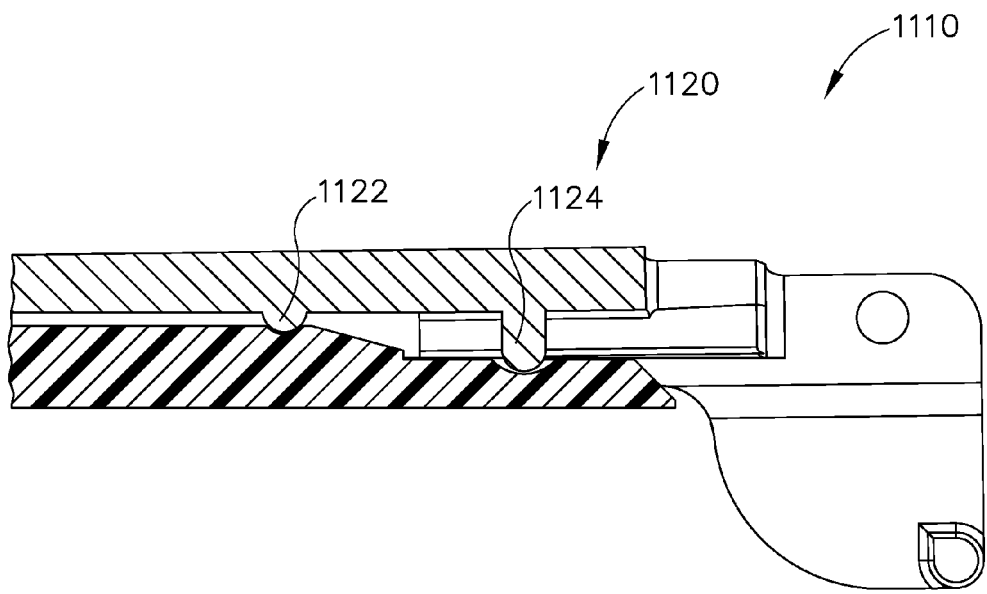
FIG. 95 depicts a side cross-sectional view of the clamp arm of FIG. 94, with at least a portion of the clamp arm engaging at least a portion of a clamp pad.

FIGS. 94 and 95 show yet another exemplary alternative clamp arm (1110) that may be readily incorporated into instrument (100) described above. Clamp arm (1110) is substantially the same as clamp arm (1010) described above, unless otherwise noted herein. For instance, like with clamp arm (1010), clamp arm (1110) is configured to receive a clamp pad (1146) by sliding clamp pad (1146) longitudinally relative to clamp arm (1110). Also like clamp arm (1010) described above, clamp arm (1110) of the present example is configured to receive clamp pad (1146) from the distal end of clamp arm (1110) rather than the proximal end. However, unlike clamp arm (1010) and clamp pad (1047), clamp arm (1110) and clamp pad (1146) of the present example utilize certain detent features to selectively lock clamp pad (1146) into position relative to clamp arm (1110).

As can be seen in FIG. 94, clamp pad (1146) of the present example comprises a dovetailed key (1147) extending proximally from the distal end of clamp pad (1146). Key (1147) is substantially the same as key (1047) described above such that the particular details of key (1147) will not be described further.

Clamp pad (1146) further includes a first detent feature (1150) and a second detent feature (1152). First detent feature (1150) is disposed on the upper face of key (1147) on the proximal end of key (1147). Second detent feature (1152) is disposed on the upper face of clamp pad (1146) adjacent to the proximal end of key (1147). Both detent features (1150, 1152) comprise a generally hemispherical indentation disposed in the surface of clamp pad (1146). As will be described in greater detail below, detent features (1150, 1152) are configured to engage corresponding features of clamp arm (1110) to selectively lock clamp pad (1146) into position relative to clamp arm (1110). Although the present example includes two detent features (1150, 1152), it should be understood that any number of detent features (1150, 1152) may be used such as one, or a plurality of detent features (1150, 1152).

Clamp arm (1110) comprises a channel (1140) extending longitudinally through clamp arm (1110) through the distal end of clamp arm (1110). Accordingly, it should be understood that channel (1140) is accessible from the distal end of clamp arm (1110). Channel (1140) is configured to receive key (1147) of clamp pad (1146) and is substantially the same as channel (1040) described above.

As can best be seen in FIG. 95, clamp arm (1110) further comprises a lock assembly (1120). Lock assembly (1120) includes two generally rigid detent features (1122, 1124) extending downwardly into channel (1140). Detent features (1122, 1124) comprise a first detent feature (1122) and a second detent feature (1124). Detent features (1122, 1124) generally correspond to detent features (1150, 1152) of clamp pad (1146). In particular, first detent feature (1122) corresponds to first detent feature (1150), and second detent feature (1124) corresponds to second detent feature (1152). Because second detent feature (1124) corresponds to second detent feature (1152) of clamp pad (1146), it should be understood that second detent feature (1152) extends downwardly a greater distance relative to first detent feature (1122) to accommodate the positioning of second detent feature (1152) on clamp pad (1146). As will be described in greater detail below, each detent feature (1122, 1124) of clamp arm (1110) is configured to engage each corresponding detent feature (1150, 1152) to selectively secure clamp pad (1146) to clamp arm (1110)

Vertical portion (1026) generally corresponds to vertical portion (1056) of clamp pad (1046). As can be seen in FIG. 84, vertical portion (1026) is configured to engage with vertical portion (1056) of clamp pad (1046). As will be described in greater detail below, engagement between vertical portion (1026) of clamp arm (1010) and vertical portion (1056) of clamp pad (1046) is generally operable to selectively prevent distal longitudinal movement of clamp pad (1046) relative to clamp arm (1010). It should be understood that in examples where vertical portion (1056) of clamp pad (1046) is oriented at a different angle, vertical portion (1026) of clamp arm (1010) may also be correspondingly different to accommodate such an angle while retaining the same functionality described above.

Figure 96:
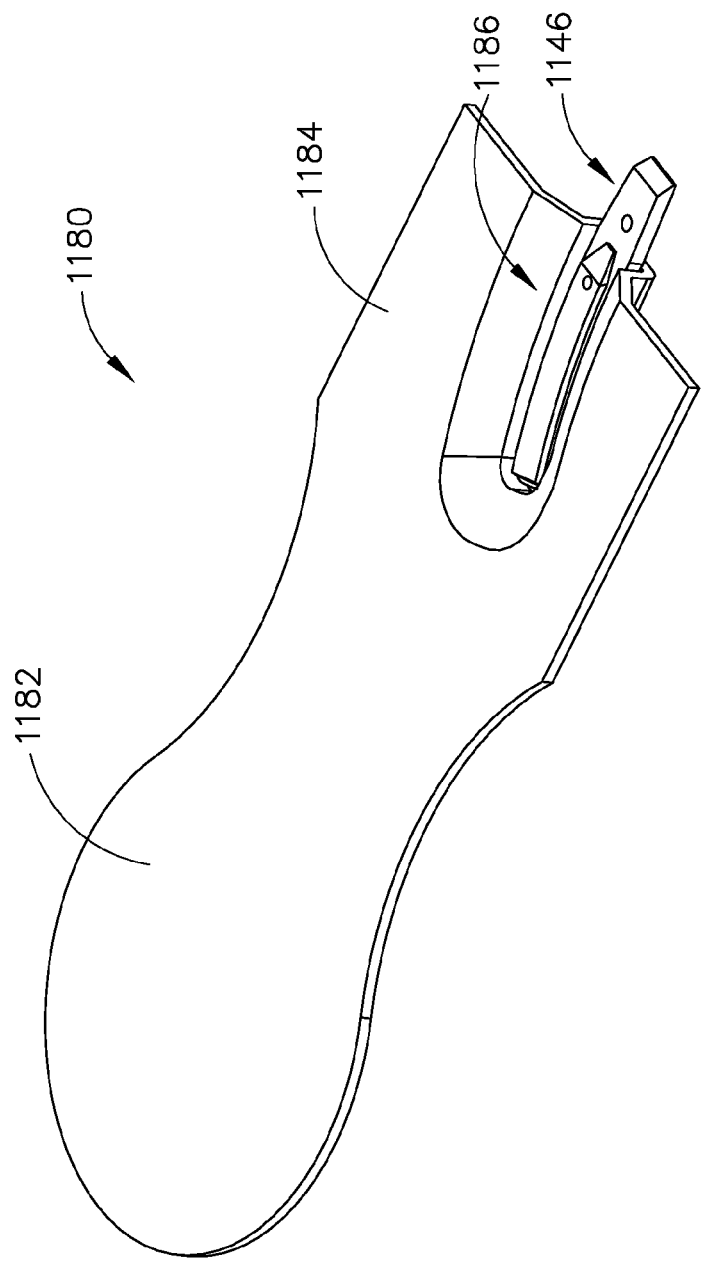
FIG. 96 depicts a perspective view of an attachment tool for use with the clamp arm of FIG. 94.

FIG. 96 shows an exemplary attachment tool (1180) for use in assisting an operator in attaching clamp pad (1146) to clamp arm (1110). Tool (1180) comprises a grip portion (1182) and a pad portion (1184). Grip portion (1182) provides a region for an operator to grip to more readily manipulate clamp pad (1146). Pad portion (1184) comprises a pad channel (1186). Pad channel (1186) is configured to receive clamp pad (1146) therein. Although not shown, it should be understood that channel (1186) also include certain features to retain clamp pad (1146) within channel (1186) until clamp pad (1146) is attached to clamp arm (1110). Of course, such features are merely optional and may be omitted in some examples.

Figure 97:
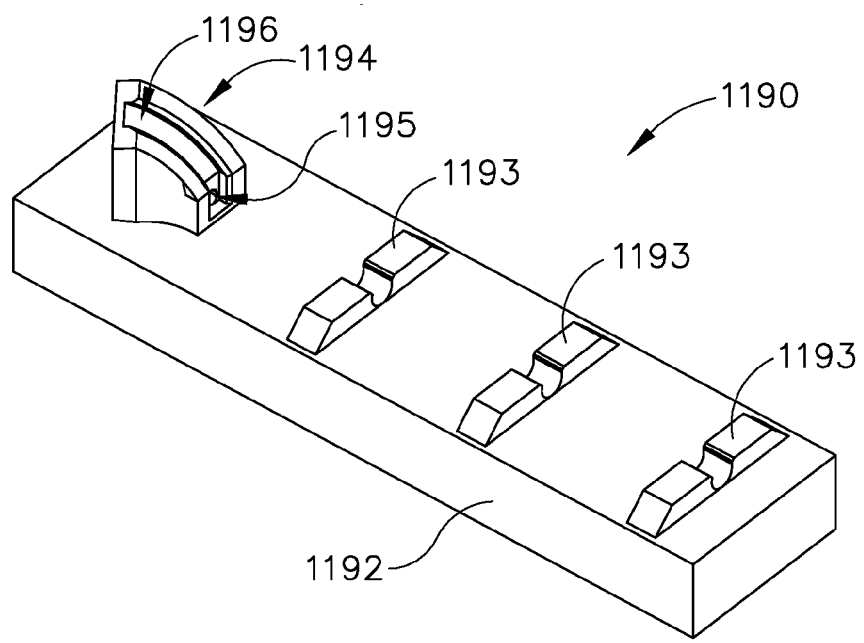
FIG. 97 depicts a perspective view of an exemplary fixture for use with the clamp arm of FIG. 94.
Figure 98:
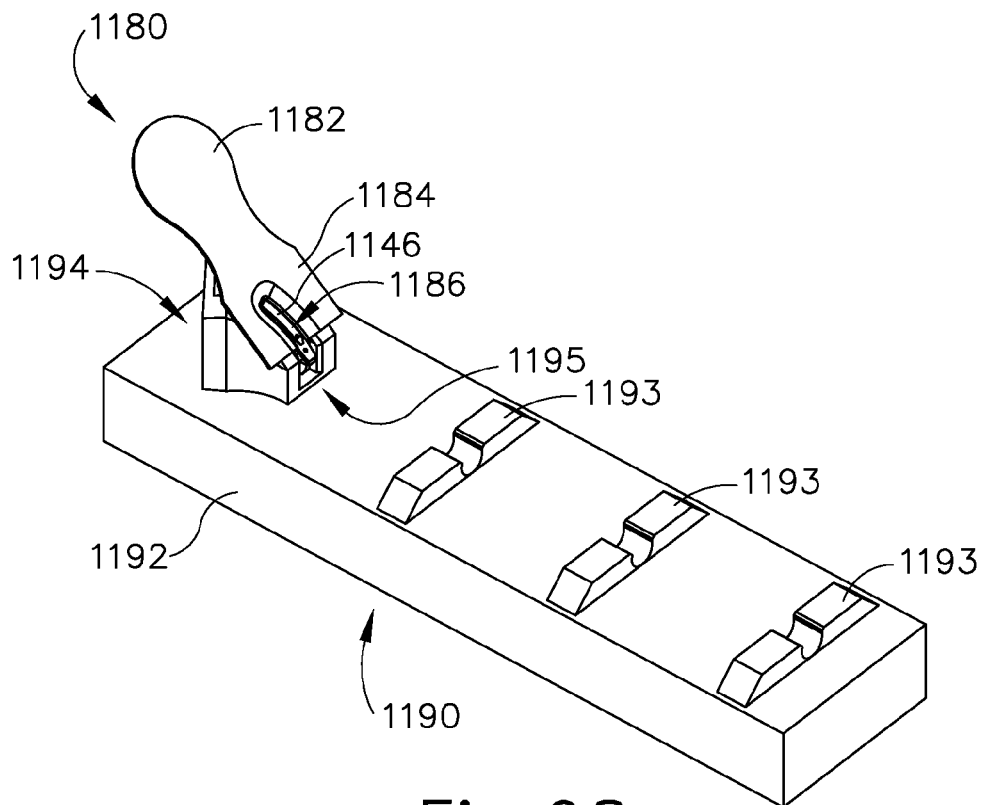
FIG. 98 depicts a perspective view of the attachment tool of FIG. 96 inserted onto the fixture of FIG. 97.

FIG. 97 shows an exemplary fixture (1190) that may be used with clamp pad (1146) and attachment tool (1180) to aid an operator in attaching clamp pad (1146) to clamp arm (1110). Fixture (1190) comprises a support block (1192), and an alignment block (1194). Support block (1192) comprises a plurality of cradle members (1193) that are configured to retain and locate instrument relative to alignment block (1194).

Alignment block (1194) comprises a blade opening (1195) and an attachment channel (1196). Blade opening (1195) receives blade (160) of instrument. Channel (1196) is angled to be adjacent to clamp arm (1110) when instrument (100) is positioned in fixture (1190) with clamp arm (1110) in an open position. Channel (1196) is further configured to receive attachment tool (1180) such that attachment tool (1180) is slidable from the distal end of channel (1196) to the proximal end of channel (1196). As will be described in greater detail below, channel (1196) is configured to permit slidability of attachment tool (1180) even when clamp arm (1110) is disposed adjacently to channel (1196).

While fixture (1190) and attachment tool (1180) are described herein in the context of being usable with clamp pad (1146) and clamp arm (1110), it should be understood that fixture (1190) and attachment tool (1180) may be readily usable with clamp pad (1046) and clamp arm (1010) described above. Indeed, as described above, clamp pad (1146) and clamp arm (1110) are substantially similar to clamp pad (1046) and clamp arm (1010). Thus, minimal, if any changes to fixture (1190) and attachment (1180) are needed in order to use clamp pad (1046) and clamp arm (1010) in conjunction with fixture (1190) and attachment (1180).

FIGS. 98-101 show an exemplary use of fixture (1190) to insert clamp pad (1146) into clamp arm (1110). As can be seen, attachment tool (1180) is initially inserted onto alignment block (1194) such that clamp pad (1146) is disposed adjacent to attachment channel (1196).

Figure 99:
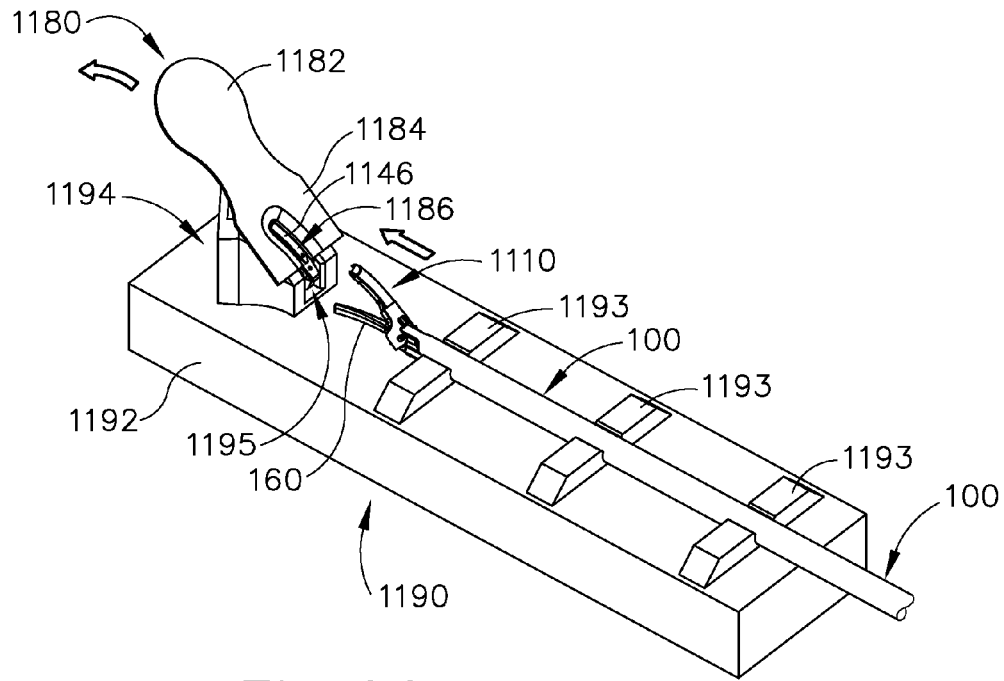
FIG. 99 depicts a perspective view of the fixture of FIG. 97 receiving the instrument of FIG. 2.
Figure 100:
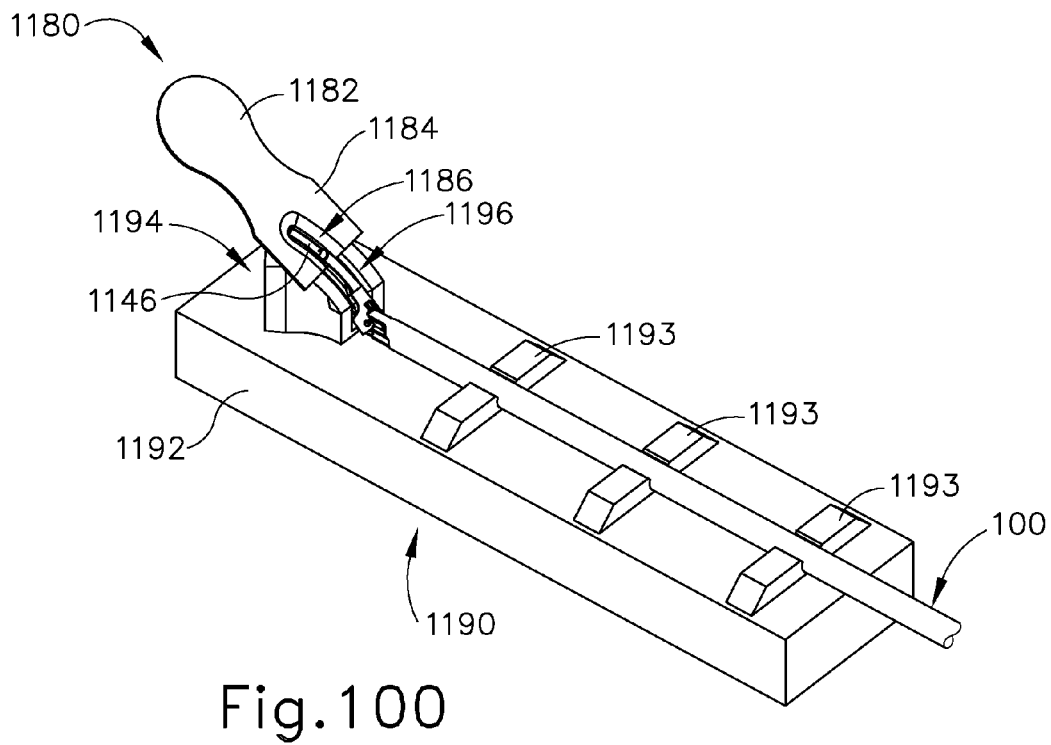
FIG. 100 depicts a perspective view of the fixture of FIG. 97, with the instrument of FIG. 2 fully inserted into the fixture.
Figure 101:
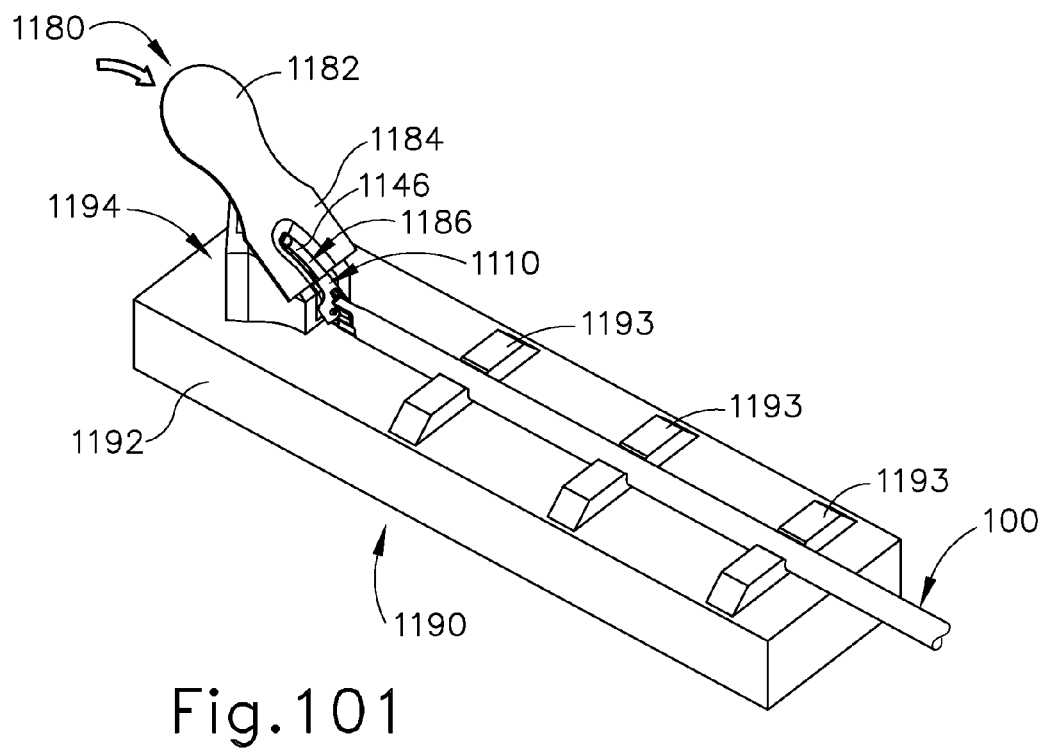
FIG. 101 depicts a perspective view of the fixture of FIG. 97, with the fixture being used to insert the clamp pad of FIG. 95 into the clamp arm of FIG. 94.

Next, as shown in FIG. 99, instrument (100) and clamp arm (1110) are inserted into fixture (1190) through cradle members (1193) of support block (1192). Prior to insertion of blade (160) into blade opening (1195) and insertion of clamp arm (1110) into a position adjacent to channel (1196), attachment tool (1180) is pulled distally to the position shown in FIG. 100 to provide space for clamp arm (1110).

Once clamp arm (1110) and instrument (100) are fully inserted into fixture (1190), an operator may begin to attach clamp pad (1146) to clamp arm (1110). To attach clamp pad (1146), an operator merely pushes attachment tool (1180) proximally in channel (1196). This guides attachment tool (1180) along the path defined by channel (1196). This path corresponds to the shape of clamp arm (1110) such that clamp pad (1146) will be inserted into channel (1140) of clamp arm (1110) as attachment tool (1180) is pushed proximally. Eventually, detent features (1150, 1152) of clamp pad (1146) will engage detent features (1122, 1124) of clamp arm (1110) and clamp pad (1146) will thereby be fastened to clamp arm (1110). Once clamp pad (1146) is attached, an operator may remove clamp pad (1146) using the procedure described above with respect to clamp pad (1046).

Figure 102:
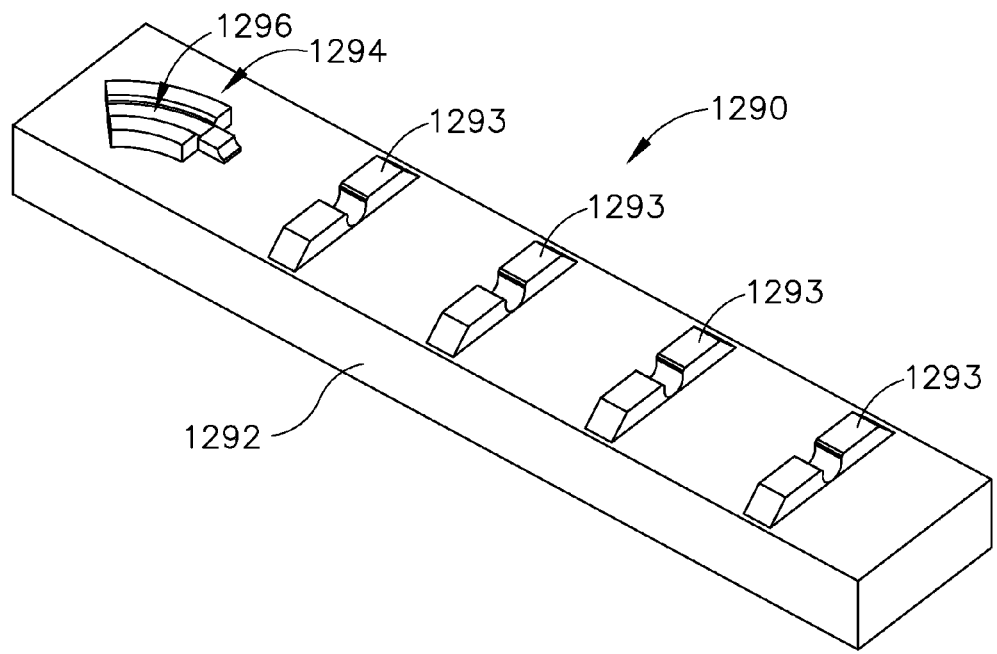
FIG. 102 depicts a perspective view of an exemplary alternative fixture for use with the clamp arm of FIG. 94.

In some instances it may be desirable to load clamp pad (1146) into clamp arm (1110) while clamp arm (1110) is in a closed state. FIG. 102 shows an exemplary alternative fixture (1290) that may be used with clamp pad (1146) and attachment tool (1180) to aid an operator in attaching clamp pad (1146) to clamp arm (1110). Fixture (1290) comprises a support block (1292), and an alignment block (1294). Support block (1292) comprises a plurality of cradle members (1293) that are configured to retain and locate instrument relative to alignment block (1294).

Alignment block (1294) comprises an attachment channel (1296). Unlike channel (1196) described above, channel (1296) is angled to be adjacent to clamp arm (1110) when instrument (100) is positioned in fixture (1190) with clamp arm (1110) in a closed position. Channel (1296) is further configured to receive attachment tool (1180) such that attachment tool (1180) is slidable from the distal end of channel (1296) to the proximal end of channel (1296). As will be described in greater detail below, channel (1296) is configured to permit slidability of attachment tool (1180) even when clamp arm (1110) is disposed adjacently to channel (1296).

Figure 103:
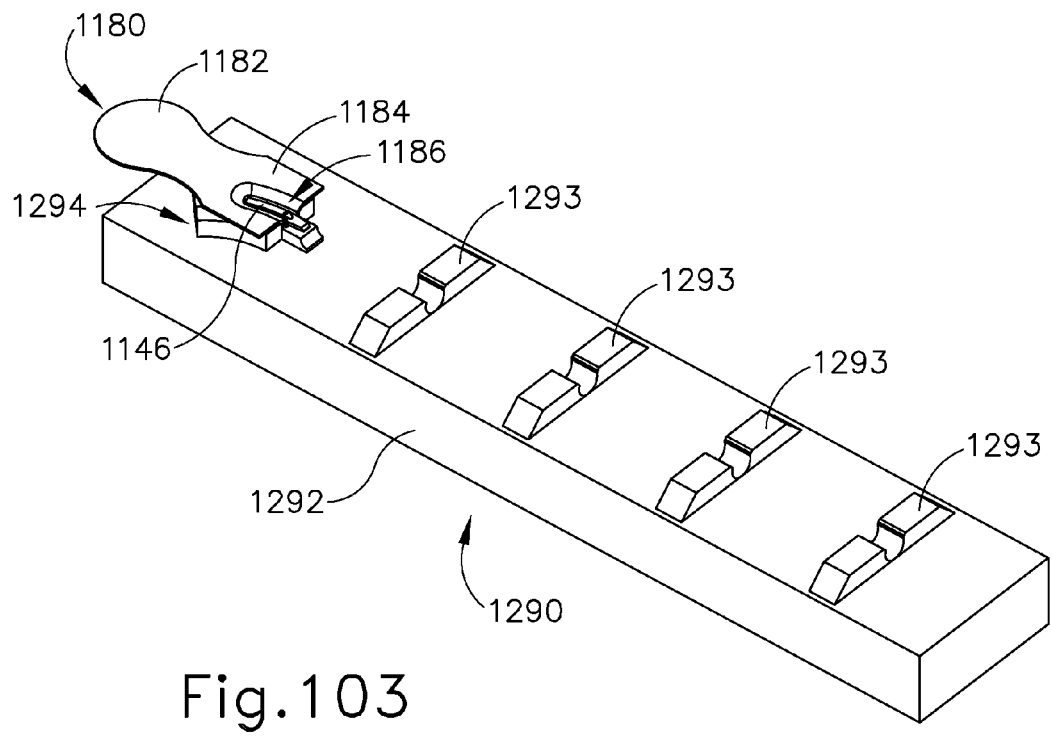
FIG. 103 depicts a perspective view of the attachment tool of FIG. 96 inserted onto the fixture of FIG. 102.
Figure 104:
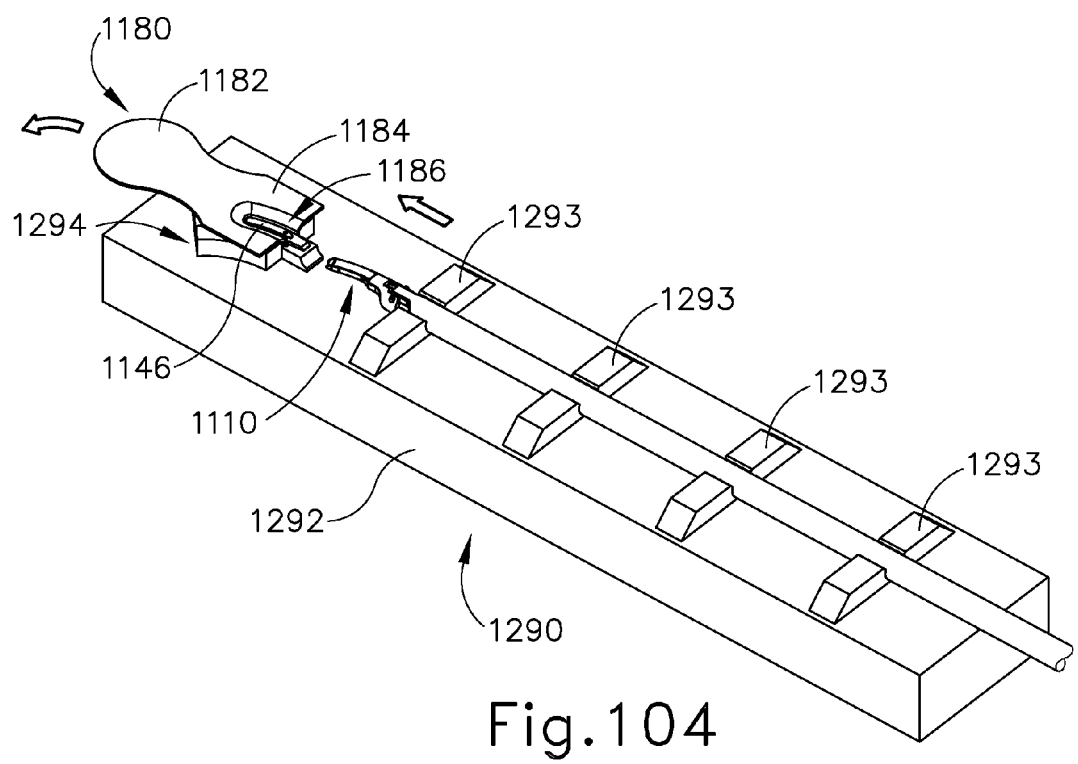
FIG. 104 depicts a perspective view of the fixture of FIG. 102 receiving the instrument of FIG. 2.
Figure 105:
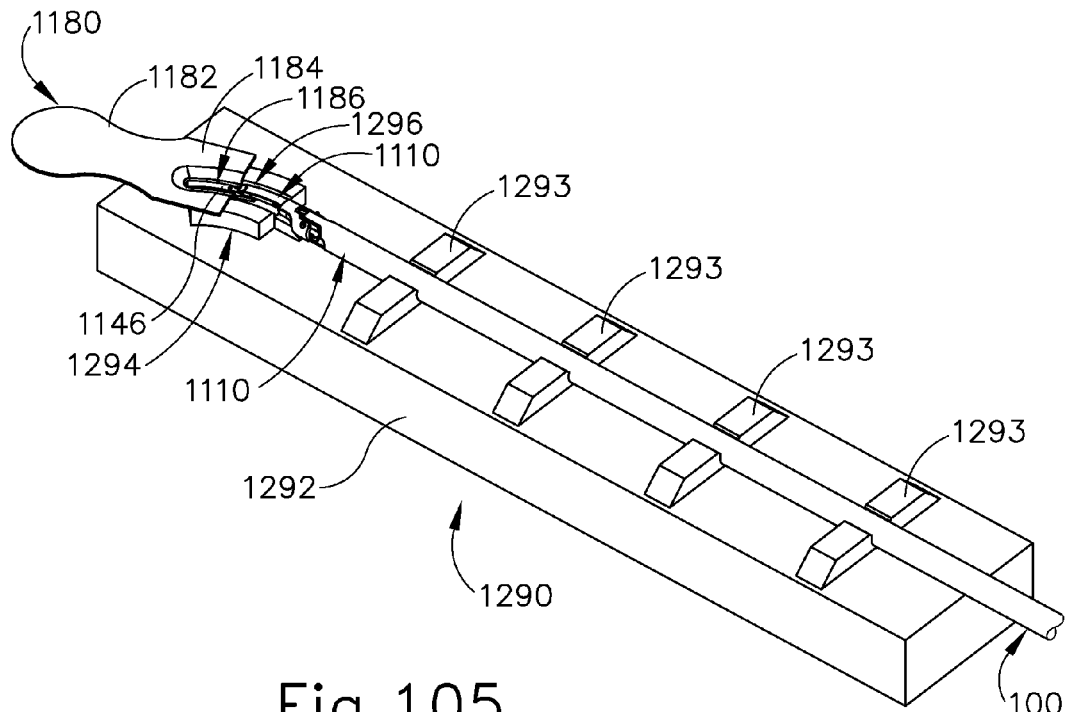
FIG. 105 depicts a perspective view of the fixture of FIG. 102, with the instrument of FIG. 2 fully inserted into the fixture.
Figure 106:
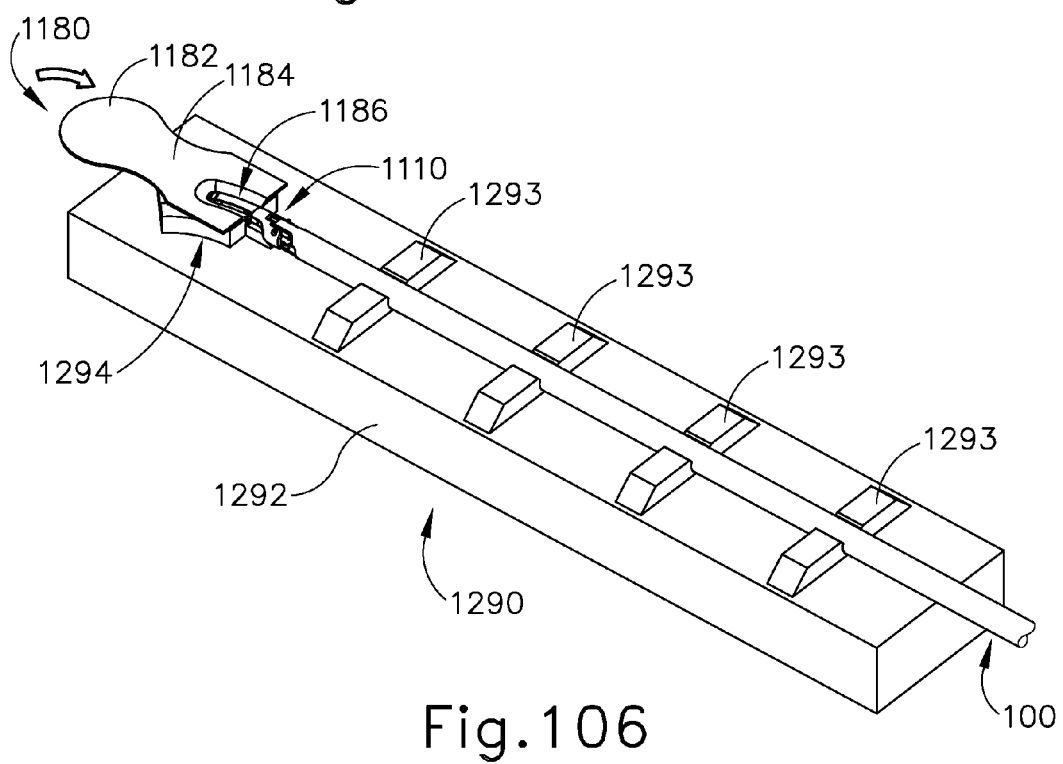
FIG. 106 depicts a perspective view of the fixture of FIG. 102, with the fixture being used to insert the clamp pad of FIG. 95 into the clamp arm of FIG. 94.

FIGS. 102-106 show an exemplary use of fixture (1290) to insert clamp pad (1146) into clamp arm (1110). As can be seen in FIG. 103, attachment tool (1180) is initially inserted onto alignment block (1294) such that clamp pad (1146) is disposed adjacent to attachment channel (1296).

Next, as shown in FIG. 103, instrument (100) and clamp arm (1110) are inserted into fixture (1290) through cradle members (1293) of support block (1292). Prior to insertion of clamp arm (1110) into a position adjacent to channel (1296), attachment tool (1180) is pulled distally to the position shown in FIG. 105 to provide space for clamp arm (1110).

Once clamp arm (1110) and instrument (100) are fully inserted into fixture (1290), an operator may begin to attach clamp pad (1146) to clamp arm (1110). To attach clamp pad (1146), an operator merely pushes attachment tool (1180) proximally in channel (1296). This guides attachment tool (1180) along the path defined by channel (1296). This path corresponds to the shape of clamp arm (1110) such that clamp pad (1146) will be inserted into channel (1140) of clamp arm (1110) as attachment tool (1180) is pushed proximally. Eventually, detent features (1150, 1152) of clamp pad (1146) will engage detent features (1122, 1124) of clamp arm (1110) and clamp pad (1146) will thereby be fastened to clamp arm (1110). Once clamp pad (1146) is attached, an operator may remove clamp pad (1146) using the procedure described above with respect to clamp pad (1046).

VII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus for operating on tissue, the apparatus comprising: (a) a body; (b) a shaft assembly, wherein the shaft assembly extends distally from the body, wherein the shaft assembly comprises an acoustic waveguide, wherein the waveguide is configured to acoustically couple with an ultrasonic transducer; and (c) an end effector, wherein the end effector comprises: (i) an ultrasonic blade in acoustic communication with the waveguide, (ii) a clamp arm, wherein the clamp arm is configured to pivot about a first pivot point toward and away from the ultrasonic blade, wherein the clamp arm comprises a coupling feature, and (iii) a clamp pad, wherein the clamp pad is selectively attachable to the clamp arm to acoustically isolate the clamp arm from the ultrasonic blade, wherein the coupling feature of the clamp arm is configured to provide a snap fit between the clamp pad and the clamp arm and thereby permit manipulation of the clamp pad for removal of the clamp pad from the clamp arm.

Example 2

The apparatus of Example 1, wherein the clam arm further comprises a proximal coupling member configured to selectively detach the clamp arm from the end effector.

Example 3

The apparatus of Example 2, wherein the proximal coupling member is responsive to rotation of the clamp arm, wherein the proximal coupling member is further configured to detach the clamp arm from the end effector in response to rotation of the clamp arm.

Example 4

The apparatus of Example 1, wherein the clamp arm further comprises a body and a distal tip, wherein the distal tip is selectively removable from the body.

Example 5

The apparatus of Example 4, wherein the distal tip is fixedly secured to at least a portion of the clamp pad.

Example 6

The apparatus of Example 5, wherein the coupling feature of the clamp arm is associated with the distal tip, wherein the coupling feature comprises at least one resilient tab, wherein the resilient tab is configured to selectively release the distal tip from the body of the clamp arm.

Example 7

The apparatus of Example 6, wherein the clamp arm further comprises a translatable engagement member, wherein the translatable engagement member is configured to translate relative to the body of the clamp arm to selectively actuate the resilient tabs.

Example 8

The apparatus of Example 5, wherein the coupling feature of the clamp arm is associated with the body, wherein the coupling feature comprises a bore and a pin, wherein the bore extends transversely through the body, wherein the pin is insertable through the bore to engage selectively engage at least a portion of the clamp pad.

Example 9

The apparatus of Example 9, wherein the pin is configured to be removed from the bore to selectively release translation of the clamp pad relative to the body.

Example 10

The apparatus of Example 1, wherein the clamp pad further comprises at least one resilient feature, wherein the resilient feature comprises at least one tooth, wherein the at least one tooth is configured to engage the coupling feature of the clamp arm.

Example 11

The apparatus of Example 10, wherein the at least one resilient member comprises a plurality of resilient members, wherein each resilient member is positioned around an outer perimeter of the clamp pad.

Example 12

The apparatus of Example 10, wherein the at least one resilient member comprises a plurality of resilient members, wherein at least two resilient members of the plurality of resilient members are configured to operate as a snap assembly.

Example 13

The apparatus of claim 12, wherein the coupling feature of the clamp arm comprises a plurality of coupling features, wherein the snap assembly comprises a plurality of snap assemblies, wherein each coupling feature of the clamp arm corresponds to a snap assembly of the clamp pad.

Example 14

The apparatus of Example 12, wherein the snap assembly is configured to form a mushroom shape.

Example 15

The apparatus of Example 1, wherein the clamp pad comprises a detent feature, wherein the detent feature is configured to engage with the coupling feature of the clamp arm to selectively secure the clamp pad to the clamp arm.

Example 16

The apparatus of Example 1, wherein the clamp arm comprises a channel, wherein the clamp pad comprises a key, wherein the key is slidable within the channel, wherein the channel is open to a distal end of the clamp pad.

Example 17

An apparatus for operating on tissue, the apparatus comprising: (a) a body; (b) a shaft assembly, wherein the shaft assembly extends distally from the body, wherein the shaft assembly comprises an acoustic waveguide, wherein the waveguide is configured to acoustically couple with an ultrasonic transducer; (c) an end effector, wherein the end effector comprises: (i) an ultrasonic blade in acoustic communication with the waveguide, and (ii) a clamp arm, wherein the clamp arm is configured to pivot about a first pivot point toward and away from the ultrasonic blade along a first angular path from a first position to a second position, (iii) a clamp pad, wherein the clamp pad comprises an attachment feature, wherein the attachment feature is configured to selectively couple the clamp pad to the clamp arm; and (d) a key, wherein the key is configured to engage at least a portion of the clamp pad to maintain lateral stability of the clamp pad relative to the clamp arm.

Example 18

The apparatus of Example 17, further comprising a decoupling tool, wherein the decoupling tool includes an engagement member, wherein the engagement member is configured to manipulate the attachment feature of the clamp pad to decouple the clamp pad from the clamp arm.

Example 19

A method for preparing an apparatus for operating on tissue, wherein the apparatus comprises a shaft assembly and an end effector, wherein the shaft assembly defines a longitudinal axis, wherein the end effector comprises a clamp arm, a clamp pad, and an ultrasonic blade, the method comprising: (a) positioning the shaft assembly in a fixture; (b) positioning the end effector adjacent to a channel disposed within the fixture; (c) loading a clamp pad into a pad receiving portion of an attachment tool, wherein the attachment tool provides a grip surface; (d) positioning at least a portion of the attachment tool in the channel of the fixture adjacent to the end effector; (e) driving the attachment tool in the channel of the fixture towards the end effector; and (d) directing the clamp pad into a channel opening in the distal end of the clamp arm using the attachment tool such that the clamp pad is attached to the clamp arm.

Example 20

The method of Example 19, wherein the act of driving the attachment tool in the channel of the fixture towards the end effector further comprises directing the attachment tool along a path corresponding to a shape of the clamp arm.

VIII. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
   (a) a shaft assembly, wherein the shaft assembly comprises an acoustic waveguide, wherein the waveguide is configured to acoustically couple with an ultrasonic transducer; and
   (b) an end effector, wherein the end effector comprises:
      (i) an ultrasonic blade in acoustic communication with the waveguide,
      (ii) a clamp arm, wherein the clamp arm is configured to pivot about a first pivot point toward and away from the ultrasonic blade, wherein the clamp arm comprises a proximal coupling member, a clamp portion, a resilient fastening member selectively detachable from both the proximal coupling member and the clamp portion, and a coupling feature, wherein the resilient fastening member comprises a first resiliently biased leaf and a second resiliently biased leaf of unitary construction, wherein the first resiliently biased leaf and the second resiliently biased leaf are configured to actuate relative to each other, wherein the proximal coupling member and the clamp portion are configured to selectively engage each other, wherein the resilient fastening member is configured to interpose between the proximal coupling member and the clamp portion to fix the proximal coupling member and the clamp portion together, and
      (iii) a clamp pad, wherein the clamp pad is selectively attachable to the clamp arm to acoustically isolate the clamp arm from the ultrasonic blade, wherein the coupling feature of the clamp arm is configured to provide a snap fit between the clamp pad and the clamp arm and thereby permit manipulation of the clamp pad for removal of the clamp pad from the clamp arm.

2. The apparatus of claim 1, wherein the proximal coupling member is responsive to rotation of the clamp arm, wherein the proximal coupling member is further configured to detach the clamp arm from the end effector in response to rotation of the clamp arm.

3. An apparatus for operating on tissue, the apparatus comprising:
   (a) a shaft assembly, wherein the shaft assembly comprises an acoustic waveguide, wherein the waveguide is configured to acoustically couple with an ultrasonic transducer;
   (b) an end effector, wherein the end effector comprises:
      (i) an ultrasonic blade in acoustic communication with the waveguide,
      (ii) a clamp arm comprising a first portion, a second portion, and a resilient locking member comprising a first resiliently biased leaf and a second resiliently biased leaf of unitary construction, wherein the first resiliently biased leaf and the second resiliently biased leaf are configured to actuate relative to each other, wherein the clamp arm is configured to pivot about a first pivot point toward and away from the ultrasonic blade along a first angular path from a first position to a second position, wherein the resilient locking member is configured to selectively fix the first portion with the second portion, and
      (iii) a clamp pad, wherein the clamp pad comprises an attachment feature, wherein the attachment feature is configured to selectively couple the clamp pad to the clamp arm; and
   (c) a key, wherein the key is configured to engage at least a portion of the clamp pad to maintain lateral stability of the clamp pad relative to the clamp arm.

4. An apparatus for operating on tissue, the apparatus comprising:
   (a) a shaft assembly, wherein the shaft assembly comprises an acoustic waveguide, wherein the waveguide is configured to acoustically couple with an ultrasonic transducer; and
   (b) an end effector, wherein the end effector comprises:
      (i) an ultrasonic blade in acoustic communication with the waveguide,
      (ii) a clamp pad, and
      (iii) a clamp arm assembly comprising:
         (A) a proximal mating portion configured to pivotably coupled with the shaft assembly, wherein the proximal mating portion defines a first pathway and a second pathway,
         (B) a clamp portion configured to receive the clamp pad, wherein the clamp portion is configured to selectively couple with the proximal mating portion, wherein the clamp portion comprises a first mating portion configured to fit within the first pathway, and
         (C) a resilient mating feature of unitary construction comprising a first resilient leaf and a second resilient leaf configured to flex relative to the first resilient leaf, where the resilient mating feature is configured to fit within the second pathway to fix the clamp portion with the proximal mating portion such that the first resilient leaf abuts against the clamp portion and the second resilient leaf abuts against the proximal mating portion.

5. The apparatus of claim 4, wherein the resilient mating feature comprises a V-shaped spring.

6. The apparatus of claim 5, wherein the V-shaped spring comprises two pins.

* * * * *